(12) United States Patent
Gravel et al.

(10) Patent No.: US 7,045,612 B2
(45) Date of Patent: May 16, 2006

(54) HUMAN METHIONINE SYNTHASE REDUCTASE: CLONING, AND METHODS FOR EVALUATING RISK OF NEURAL TUBE DEFECTS, CARDIOVASCULAR DISEASE, AND CANCER

(75) Inventors: Roy A. Gravel, Calgary (CA); Rima Rozen, Montreal West (CA); Daniel Leclerc, Montreal (CA); Aaron Wilson, Montreal (CA); David Rosenblatt, Montreal (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/371,347

(22) Filed: Aug. 10, 1999

(65) Prior Publication Data

US 2003/0082676 A1 May 1, 2003

Related U.S. Application Data

(63) Continuation-in-part of application No. 09/232,028, filed on Jan. 15, 1999, now abandoned.

(60) Provisional application No. 60/071,622, filed on Jan. 16, 1998.

(51) Int. Cl.
| | |
|---|---|
| C12N 15/53 | (2006.01) |
| C12N 9/02 | (2006.01) |
| C12N 15/00 | (2006.01) |
| C12N 5/00 | (2006.01) |
| C12N 1/20 | (2006.01) |
| C12Q 1/26 | (2006.01) |
| C12P 21/06 | (2006.01) |
| C07H 21/04 | (2006.01) |

(52) U.S. Cl. .................. 536/23.2; 435/320.1; 435/25; 435/325; 435/252.3; 435/69.1; 435/189; 536/23.1; 536/24.31; 536/23.5

(58) Field of Classification Search .............. 435/189, 435/25, 320.1, 69.1, 252.3, 325; 536/23.2, 536/23.1, 23.5, 24.31
See application file for complete search history.

(56) References Cited

FOREIGN PATENT DOCUMENTS

| WO | WO 97/25440 | 7/1997 |
| WO | WO 99/06552 | 2/1999 |

OTHER PUBLICATIONS

Strausberg "*Homo sapiens* cDNA clone IMAGE:704126 5', mRNA sequence", GenBank direct Submission Accession No. AA279276, 1997.*

Hillier et al. "Generation and Analysis of 280,000 Human Expressed Sequence Tas" (1996) Genome Res 6:807-828.*
Bork, Genome Research, 10:398-400, 2000.*
Broun et al., Science 282:1315-1317, 1998.*
Seffernick et al., J. Bacteriol. 183(8):2405-2410, 2001.*
Van de Loo et al., Proc. Natl. Acad. Sci. 92:6743-6747, 1995.*
Witkowski et al., Biochemistry 38:11643-11650, 1999.*
Wilson et al., "Molecular basis for methionine synthase reductase deficiency in patients belonging to the cbIE complementation group of disorders in folate/cobalamin metabolist," Human Molecuar Genetics 8(11):2009-2016, (1999).
Brasch et al., "Neonatal Megaloblastic Anemia Associated with Reduced Cellular Uptake of Folate and Low Methyl-B12 Levels: A New Mutation," Aust. N. Z. J. Med. 18 Supp.434 (1988).
Frosst et al., "A Candidate genetic Risk Factor for Vascular Disease: a Common Mutation in Methylenetetrahydrofolate Reductase," Nat. Genet. 10:111-113 (1995).
Goyette et al., "Human methylenetetrahydrofolate reductase: isolation of cDNA, mapping and mutation identification" Nature Genetics 7:195-200 (1994).
Gulati et al., "Defects in Auxillary Redox Proteins Lead to Functional Methionine Synthase Deficienty," J. Biol. Chem. 272:19171-19175 (1997).
Hudson et al., "An STS-Based Map of the Human Genome," Science 270:1945-1954 (1995).
Leclerc et al., "Molecular Cloning, Expression and Physical Mapping of the Human Methionine Synthase Reductase Gene," Gene 12140:1-14 (1999).
Leclerc et al., "Cloning and mapping of a cDNA for methionine synthase reductase, a flavoprotein defective in patients with homocystinuria" Proc. Natl. Acad. Sci. USA 95:3059-3064 (1998).

(Continued)

Primary Examiner—Rebecca E. Prouty
Assistant Examiner—Delia M. Ramirez
(74) Attorney, Agent, or Firm—Kristina Bieker-Brady; Clark & Elbing LLP

(57) ABSTRACT

The invention features a novel gene encoding methionine synthase reductase. The invention also features a method for detecting an increased likelihood of hyperhomocysteinemia and, in turn, an increased or decreased likelihood of neural tube defects, cardiovascular disease, or cancer. The invention also features therapeutic methods for treating and/or reducing the risk of cardiovascular disease, cancer, or neural tube defects. Also provided are the sequences of the human methionine synthase reductase gene and protein and compounds and kits for performing the methods of the invention.

15 Claims, 14 Drawing Sheets

OTHER PUBLICATIONS

Rosenblatt et al., "Altered Vitamin $B_{12}$ Metabolism in Fibroblasts from a Patient with Megaloblastic Anemia and Homocystinuria Due to a New Defect in Methionine Biosynthesis," J. Clin. Invest. 74:2149-2156 (1984).

Rosenblatt et al., "Prenatal Vitamin $B_{12}$ Therapy of a Fetus with Methylcobalamin Deficiency (Cobatamin E Disease)," Lancet 1:1127-1129 (1985).

Rozen, "Molecular Genetic Aspects of Hyperthomocysteinemia and its Relation to Folic Acid," Clin. Invest. Med. 19;171-178 (1996).

Schuh et al., "Homocystinuria and Megaloblastic Anemia Responsive to Vitamin $B_{12}$ Therapy," N. Engl. J. Med. 310:686-690 (1984).

Tauro et al., "Dihydrofolate Reductase Deficiency Causing Megaloblastic Anemia in two Families," N. Engl. J. Med., case one 294:466 (1976).

van der Put et al., "Mutated Methylenetetrahydrofolate Reductase as a Risk Factor for Spina Bifida," The Lancet 346:1070-1071 (1995).

Watkins et al., "Functional Methionine Synthase Deficiency (cbIE and CblG): Clinical and Biochemical Heterogeneity," Am. J. Med. Genet. 34:427-434 (1989).

Wilson et al., "A Common Variant in Methionine Synthase Reductase Combined with Low Cobalamin (Vitamin $B_{12}$) Increase Risk for Spina Bifida," Molecular Genetics and Metabolism 67:317-323 (1999).

* cited by examiner

```
                                CAAGGTTGGTGAAGTCGCGTTGTGCAGTTCTGCGCCGGCTGGTTCACTGTTACATGCCTTGAAGTG
  1 ATGAGGAGGTTTCTGTTACTATATGCTACACAGCAGGACAGGCAAAGGCCATCGCAGAAGAAATGTGTGAGCAGGCTGTTGTACATGGATTTTCTGCAGATCTTCACTGTATTAGTGAA   40
    M  R  R  F  L  L  L  Y  A  T  Q  Q  G  Q  A  K  A  I  A  E  E  M  C  E  Q  A  V  V  H  G  F  S  A  D  L  H  C  I  S  E
121 TCCGATAAGTATGACCTAAAAACCGAAACAGCTCCTCTTGTTGTTGTTGTTTCTACCACCGGGACCCACCGGAGACCCGACAGTTGTTAAGGAAATACAGAACCAAACA                       80
    S  D  K  Y  D  L  K  T  E  T  A  P  L  V  V  V  S  T  T  G  T  G  D  P  P  D  T  A  R  K  F  V  K  E  I  Q  N  Q  T
241 CTGCCGGTTGATTTCTTTGCTCACCTGCGGTATGGGTTACTGGGTCTCGGTGATTCAGAATCAGAGATACACCTACTTTTGCAATGGGGGAAGATAATTGATAAACGACTTCAAGAGCTTGGAGCC     120
    L  P  V  D  F  F  A  H  L  R  Y  G  L  L  G  L  G  D  S  E  Y  T  Y  F  C  N  G  G  K  I  I  D  K  R  L  Q  E  L  G  A
361 CGGCATTTCTATGACACTGGACATGCCAGATGCGTGGGACTGTGTAGGTTTAGAACTGCTGGTTGAGCCGTGGATTGCTGGCCTGGACTCTGGATTCGATGATCAAGAGGACAA                160
    R  H  F  Y  D  T  G  H  A  D  D  C  V  G  L  B  L  V  V  E  P  W  I  A  G  L  W  P  A  L  R  K  H  F  R  S  S  R  G  Q
481 GAGGAGATAAGTGGGCCACTCCCGGTGGCCATCACCCTGAAGACAGAACCTTGTGAAGTCAGAGACCTTGAGTCGAGCTGCTACACAGCTGCTTCTGAGTCGAGCTTCTGAGATCGAGATTCAGGA      200
    E  E  I  S  G  A  L  P  V  A  S  P  A  S  L  R  T  D  L  V  K  S  E  L  L  H  I  E  S  Q  V  E  L  L  R  F  D  D  S  G
601 AGAAGGATTCTGAGTTTACCCCCAGAATATTACAGTGAACAGCAAAATGCAGTACATCTGCAGGAGGAAAAGCCAGTATCTGACTTGACTCAGCAGATCCAGTTTTCAAGTGCCAATTTCAAAG      240
    R  K  D  S  E  V  L  K  Q  N  A  V  N  S  N  Q  S  N  V  I  E  D  F  E  S  S  L  T  R  S  V  P  P  L  S  Q  A  S  L
721 AATATTCCTGGTTTACCCCCAGAATATCTGCAGGTCCATGTCCATAAAATGATGATGCCATAAAAACCACTCTGCTGTAGAATTGGACACATTTCAAATACAGACTTTTCCTATCAGCCTGGAGATGCCTTCAGCGTGATCTGCCCTAACAGT   280
    N  I  P  G  L  P  P  E  Y  L  Q  V  H  L  Q  E  S  L  G  Q  E  E  S  Q  V  S  V  T  S  A  D  P  V  F  Q  V  P  I  S  K
841 GCAGTTCAACTTACTACGAATGATGCCATAAAAACCACTCTGCTGGTAGAATTGGACATTTCAAATACAGACTTTTCCTATCAGCCTGGAGATGCCTTCAGCGTGATCTGCCCTAACAGT       320
    A  V  Q  L  T  T  N  D  A  I  K  T  T  L  L  V  E  L  D  I  S  N  T  D  F  S  Y  Q  P  G  D  A  F  S  V  I  C  P  N  S
961 GATTCTGAGGTACAAAGCCTACTCCAAAGACTGCAGCTTGAAGATAAAAGAGAGCACTGCTGTCCTTTTGAAGATAAAGGCAGACAAAGAAATAAAGGCAGACTACCTTACCCCAGCATA          360
    D  S  E  V  Q  S  L  L  Q  R  L  Q  L  E  D  K  R  R  E  H  C  V  L  L  K  I  K  A  D  T  K  K  G  A  T  L  P  Q  H  I
1081 CCTGCGGGATGTTCTCCAGTTCATTTTTACCTGGTGTCTTGAAATCCGAGCCATTCCTAAAAAGGCATTTTGCGAGCCCTTGACTGACTATACCAGTGACTGACAGTGCTGAAAAGCCGCAGG      400
    P  A  G  C  S  L  Q  F  I  F  T  W  C  L  E  I  R  A  I  P  K  K  A  F  L  R  A  L  V  D  Y  T  S  D  S  A  E  K  R  R
1201 CTACAGGAGCTGTGCAGTAAACAAGGGGCAGCCGATTATAGCCGCTTTGTACGAGATGCCTGTGCCTGCCTTCTTGATCTCCTCGCTTTCCCTTCCTGCCAGCCAGTGTGCTCCCACTCAGTCTC     440
    L  Q  E  L  C  S  K  Q  G  A  A  D  Y  S  R  F  V  R  D  A  C  L  L  D  L  L  A  F  P  S  C  Q  P  P  L  S  L
```

```
                                                                                                                                40
                          CAAGGTTGGTGTGGAAGTCGCGTTGTGTCAGGTTCGTGCCCGGCTGGTCGCGGCGTGGTTCACTGTTACATGCCTTGAAGTG
    1 ATGAGGAGGTTTCTGTTACTATATGCTACACAGCAGGGACAAGGCCATCGCAGAAGAAATGTGTGAGCAAGCTGTGGTACAAGCTGTGGTACATGGATCTTCACTGTATTAGTGAA
      M  R  R  F  L  L  L  Y  A  T  Q  Q  G  Q  A  K  A  I  A  E  E  M  C  E  Q  A  V  V  H  G  F  S  A  D  L  H  C  I  S  E
                                                                                                                                80
  121 TCCGATAAGTATGACCTAAAAACCGAAACAGCTCCTCTTGTTGTGGTTTCTACCACGGGCACCGGAGACCCGACAGCCCGACACAGCCCGACACAGCCCGACAACGTTGTTAAGGAAATACAACCAAACA
      S  D  K  Y  D  L  K  T  E  T  A  P  L  V  V  V  S  T  T  G  D  P  P  D  T  A  R  K  F  V  K  E  I  Q  N  Q  T
                                                                                                                                120
  241 CTGCCGGTTGATTTCTTTGCTCACCTGCGGTATGGGTCTCGGTTACTGGGTCTGATTCAGAATACACCTACTTTGCAATGGGGAAGATAATGATAAACGACTTCAAGAGCTTGGAGCC
      L  P  V  D  F  F  A  H  L  R  Y  G  L  L  G  L  D  S  E  Y  T  Y  F  C  N  G  G  K  I  I  D  K  R  L  Q  E  L  G  A
                                                                                                                                160
  361 CGGCCATTTCTATGACACTGGACATGGCAGATGACTGTGTAGGTTTAGAACTTGTGGTTGAGCCGGTTGAGCCGGATTGCTGGAGTCAGAGCTGAGCCTCGGCCAGCCCTCAGAAAGCATTTAGTCAAGCAGAGGACAA
      R  H  F  Y  D  T  G  H  A  D  D  C  V  G  L  E  L  V  V  E  P  W  I  A  G  L  W  P  A  L  R  K  H  F  R  S  S  R  G  Q
                                                                                                                                200
  481 GAGGAGATAAGTGGCGACACTCCCGGTGGCATCGCGTCCTGAGGACAGACCTTGTGAAGTCAGAGCTGCTACACATTGAATCTCAAGTCGAGCTTCTGAGATTCGATGATTCAGGA
      E  E  I  S  G  A  L  P  V  A  S  P  A  S  L  R  T  D  L  V  K  S  E  L  L  H  I  E  S  Q  V  E  L  L  R  F  D  D  S  G
                                                                                                                                240
  601 AGAAAGGATTCTGAGGTTTTGAAGCAAAATGCAGTGAACATCGAGTGTAATTGTAATTGTGTAATTGAAGACTTTGAGTCCTCACTTACCCGTTCGGTACCCCACTCTCACAAGCCTCTCTG
      R  K  D  S  E  V  L  K  Q  N  A  V  N  S  N  Q  S  N  V  V  I  E  D  F  E  S  S  L  T  R  S  V  P  P  L  S  Q  A  S  L
                                                                                                                                280
  721 AATATTCCTGGTTTACCCCCAGAATATTTACAGGTACATCTGCAGGAGTCTCTTGGCCAGGAGGAAAGCCAAGTATCTGTGACTTCAGCAGATCCAGTTTTCAAGTGCCAATTTCAAAG
      N  I  P  G  L  P  P  P  E  Y  L  Q  V  H  L  Q  E  S  L  G  Q  E  E  S  Q  V  S  V  T  S  A  D  P  V  F  Q  V  P  I  S  K
                                                                                                                                320
  841 GCAGTTCAACTTACTACGAATGATGCCATAAAGACTTCAAATGACTTCTCTGCTGGTAGAATGGACATTTCAAATACAGACTTTCAAAATAAAGGCACACAAAGACACTACCCCAGCATATA
      A  V  Q  L  T  T  N  D  A  I  K  T  T  L  L  V  E  L  D  I  S  N  T  D  F  S  Y  Q  P  G  D  A  F  S  V  I  C  P  N  S
                                                                                                                                360
  961 GATTCTGAGGTACAAAGCTTACTCCAAAGACTGCAGCTTGACTTCATTTTACCTGTCTTGAAATCCTGAAATCCGAGCAATTCCTAAAAAGGCATTTTTGCGAGCCCTTGTGGACTACAGCCTGACACTGCTGAAAAGCGCAGG
      D  S  E  V  Q  S  L  L  Q  R  L  Q  L  E  D  K  R  E  H  C  V  L  L  K  I  K  A  D  T  K  K  K  G  A  T  L  P  Q  H  I
                                                                                                                                400
 1081 CCTGCGGGATGTCTTCTCCAGTTGCATTTGTCTGTCTGTAATCCGAGCAATTCCTAAAAAGGCATTTTGCGAGCCCTTGTGGACTACAGCCTGACACTGCTGAAAAGCGCAGG
      P  A  G  C  S  L  Q  F  I  F  T  W  C  L  E  I  R  A  I  P  K  K  A  F  L  R  A  L  V  D  Y  T  S  D  S  A  E  K  R  R
                                                                                                                                440
 1201 CTACAGGAGCTGTGCAGTAAACAAGGGGCAGCCGATTATAGCCGCTTTGTACGAGATGCCTGTTGGATCTCCTCCTTCTGCCAGCCACCACTCAGTCTC
      L  Q  E  L  C  S  K  Q  G  A  A  D  Y  S  R  F  V  R  D  A  C  L  L  D  L  L  A  F  P  S  C  Q  P  P  L  S  L

Fig. 3-3
```

```
1321 CTGCTCGAACATCTTCCTAAACTTCTCAACCCAGACCATATTCGTGTCAAGCTCAAGTTTATTCACCCAGGAAAGCTCCATTTGTCTTCAACATTGTGAATTTCTGTACTGCCACA 480
      L  L  E  H  L  P  K  L  Q  P  R  P  Y  S  C  A  S  S  S  L  F  H  P  G  K  L  H  F  V  F  N  I  V  E  F  L  S  T  A  T

1441 ACAGAGGTTCTGCGGAAGGGAGTATGTACAGGCTGGCTGCTGTTGGTGCTGCCTTGTGGTTGCTTCAGTTCTTCAGCCAATCATACATGATCATCCATGAAGACAGCGGGAAGCCCTGGCTCCTAAGATA 520
      T  E  V  L  R  K  G  V  C  T  G  W  L  A  L  L  V  A  S  V  L  Q  P  N  I  H  A  S  H  E  D  S  G  K  A  L  A  P  K  I

1561 TCCATCTCTCCTGAACAACAAATTCTTCCTGACTTACCAGATGACCCCTCAATCCCATCATAATGTGGGTCCAGGAACCGGCATAGCCCCGTTTATTGGTTCCTACAACATAGAGAG 560
      S  I  S  P  R  T  T  N  S  F  H  L  P  D  D  D  P  S  I  P  I  I  M  V  G  P  G  T  G  I  A  P  F  I  G  F  L  Q  H  R  E

1681 AAACTCCAAGAACAACACCCAGATGAAATTTGGAGCAATGTGGTTGTTTTTTGGCTGCAGGCATAAGGATAGGGATTATCTATTCAGAAAAGAGCTCAGACATTCCTTAAGCATGGG 600
      K  L  Q  E  Q  H  P  D  G  N  F  G  A  M  W  L  F  F  G  C  R  H  K  D  R  D  Y  L  F  R  K  E  L  R  H  F  F  L  K  H  G

1801 ATCTTAACTCATCTAAAGGTTTCCTTCTCAAGAGATGCTCCTGTTGGGGAGGAGGAAGCCCCAGCCAAGTATGTACAAGACAACATCCAGCTTCATGGCCAGCAGTGGCAGGTGGCCGAGAATCCTC 640
      I  L  T  H  L  K  V  S  F  S  R  D  A  P  V  G  E  E  E  A  P  A  K  Y  V  Q  D  N  I  Q  L  H  G  Q  Q  V  A  R  I  L

1921 CTCCAGGAGAACGGCCATATTTATGTGTGTGGAGATGCAAAGAATATGGCCAAGGATGTACATGATGCCCTTGTCCAAATAATAAGCAAAGAGGTTGGAGTTGAAAACTAGAAGCAATG 680
      L  Q  E  N  G  H  I  Y  V  C  G  D  A  K  N  M  A  K  D  V  H  D  A  L  V  Q  I  I  S  K  E  V  G  V  E  K  L  E  A  M

2041 AAAACCCTGGCCACTTTAAAAGAAGAAAACGCTACCTTCAGGATATTTGGTCATAAAACCAGAAATTAAAGAAGAGGATTAAGCTTTTTGACTGAAAGTACTAAAAGTCAGCTTTAC
      K  T  L  A  T  L  K  E  E  K  R  Y  L  Q  D  I  W  S  ***

2161 TAGTGCCAAACCTTTAAATTTCAAAAGAAAATTTCTTTCAACATTTCTTGAAGGACATGGAGTGGAGATTGGATCATTAACAATATAACAAAACTTCCTGATTTGATTTACGTATC
2281 TTCTATCTACGCCCCTTCCTGTGCCTCTGACTCTGACTCCTCCCAAATTGCCTCTGTCCTTGTGCCTTGTCAGCAGCCTTCAGTCCTCCTCAGTGCGCCTCCTTACTTCCCAGAGAACT
2401 TCACAGAGACTCTGTCCTTCCATGCAAAGGCTTCCTGAAATAGGGAGACTGACTAGCTCATTCTTGTGACTTATGTTTATATGTTAATTACACATGTGGGAAATATCGTTATATGTTAACATCAAATGGTATTGTTACTAAAGCTATATTCTG
2521 TATGTGTATACCATAAAGAATGCTTCATAAGCTCATATTAATGTACTAAATTAATTTTTATGATGTCGGGAAATATGAAGCTACCAGTAGTATTTTAAATTTCACTCTGGCATATGGATTTATCATCCATTACCATTACTTTT
2641 ATAAAAATATTTTTAGGATAATTTCAGAATTTGCATTCATTCAGTTGGGACATTTGTCTCCATGATGAATTTGTCAAAATCCAACTTTTATCCTTTTATTTCTGCTCTT
2761 TTTTAAGTCACATTTGAGTTCCCACATTATTTCGTTGCACACAAAAAACAAAATGTATGATATAATCTTTCTCCACTGTTCTAATATGTAATACTGACTTTAGTACTCCTTGGATTTTTAGATTCCCCAGTGCTAAT
2881 GGCACATTTGAGTTCCCACATTATTTGCACACAAAAAACAAAATGTATGATATAATCTTTCTCCACTGTTCTAATATGTATTTTATTGATAGCTTGGATTTAAAAACATCTCTGTTGAAGGCTTT
3001 TCCCTGTTATAATTTGCACACAAAAAACAAAATGTATGATATAATCTTTCTCCACTGTTCTAATATGTATTTTATTGATAGCTTGGATTTAAAAACATCTCTGTTGAAGGCTTT
3121 TGATCCTTTTGAGAAATAAAGATCTGAAAGAATAAGGCATAATCTTAAAAAAAAAAAAAAAA
```

Fig. 3-4

```
HsMTRR   ------------------------------------------------
CeMTRR   ------------------------------------------------
HsCPR    MGDSHVDTSSTVSEAVAEEVSLFSMTDMILFSLIVGLLTYWFLFRKKKEE    50
                                        FMN
HsMTRR   ------------------------MRRFLLLYATQQGQAKAIAEEMCE     24
CeMTRR   ------------------------MTDFLIAFGSQTGQAETIAKSLKE     24
HsCPR    VPEFTKIQTLTSSVRESSFVEKMKKTGRNIIVFYGSQTGTAEEFANRLSK   100
                           .. ...* *   *..
                                             FMN
HsMTRR   QAVVHGFSADLHCISESDK-YDLKT-------ETAPLVVVVSTTGTGDPP    66
CeMTRR   KAELIGLTPRLHALDENEKKFNLNE-------EKLC-AIVVSSTGDGDAP    66
HsCPR    DAHRYG----MRGMSADPEEYDLADLSSLPEIDNALVVFCMATYGEGDPT   146
         *    *    .  . ...*.        .          ... * **
                            FMN
HsMTRR   DTARKFVKEIQNQTLPVDFFAHLRYGLLGLGDSEYTYFCNGGKIIDKRLQ   116
CeMTRR   DNCARFVRRINRNSLENEYLKNLDYVLLGLGDSNYSSYQTIPRKIDQLT    116
HsCPR    DNAQDFYDWLQETDVD---LSGVKFAVFGLGNKTYEHFNAMGKYVDKRLE   193
         *`  *   ..  .         . . .***. *  .    ..** *

HsMTRR   ELGARHFYDTGHADDCVGLELVVEPWIAGLWPALRKHFRSSRGQEEISGA   166
CeMTRR   ALGANRLFDRAEADDQVGLELEVEPWIEKFFATLASRFDISADKMN----   162
HsCPR    QLGAQRIFELGLGDDDGNLEEDFITWREQFWPAVCEHF----------GV   233
            ***    ...  .**  **   *    . .  *

HsMTRR   LPVASPASLRTDLVKSELLHIESQVELL--RFDDSGRKDSEVLKQNAVNS   214
CeMTRR   -AITESSNLKLNQVKTE----EEKKALLQKRIEDEESDDEGRGRVIGID-   206
HsCPR    EATGEESSIRQYEL-----------VVHTDIDAAKVYMGEMGRLKSYEN    271
            . ..                    ..  .          . ..

HsMTRR   NQSNVVIEDF---ESSLTRSVPPLS-QASLNIPGLPPEYLQVHLQESLGQ   260
CeMTRR   ---MLIPEHYDYPEISLLKGSQTLSNDENLRVPIAPQPFIVSSVSNRKLP   253
HsCPR    QKP-----PFD---------------------AKNPFLAAVTTNRKLN    293
                .                                    .. .

HsMTRR   EESQVS-------VTSADPVFQVPISKAVQLTT--NDAIKTTLLVELDIS   301
CeMTRR   EDTKLEWQNLCKMPGVVTKPFEVLVVSAEFVTDPFSKKIKTKRMITVDFG   303
HsCPR    QGTE---------------------------------RHLMHLELD     306
         . .                                    .. ..

HsMTRR   N--TDFSYQPGDAFSVICPNSDSEVQSLLQR-LQLEDKREHCVLLKIKAD   348
CeMTRR   DHAAELQYEPGDAIYFCVPNPALEVNFILKRCGVLDIADQQCEL-SINPK   352
HsCPR    ISDSKIRYESGDHVAVYPANDSALVNQLGK---ILGADLD--VVMSLNNL   351
            .*. **    *   *. .     *      .  ..

HsMTRR   TKKKGATLPQHIPAGCSLQFIFTWCLEIRAIPKKAFLRALVDYTSDSAEK   398
CeMTRR   TEKINAQIPGHVHKITTLRHMFTTCLDIRRAPGRPLIRVLAESTSDPNEK   402
HsCPR    DEESNKKHP--FPCPTSYRTALTYYLDITNPPRTNVLYELAQYASEPSEQ   399
                 *     .. *  *.*  *   . *..*. *
```

Fig. 4-1

```
HsMTRR    RRLQEL--CSKQGAADYSRFVRDACACLLDLLLAFPSCQPPLSLLLEHLP    446
CeMTRR    RRLLEL--CSAQGMKDFTDFVRTPGLSLADMLFAFPNVKPPVDRLIELLP    450
HsCPR     ELLRKMASSSGEGKELYLSWVVEARRHILAILQDCPSLRPPIDHLCELLP    449
            *   .  *.*    .*     .*   *   **.  *  * **
                    FAD            FAD         FAD
HsMTRR    KLQPRPYSCASSSLFHPGKLHFVFNIVEFLSTATTEVLRKGVCTGWLALL    496
CeMTRR    RLIPRPYSMSS---YENRKARLIYSEMEFPATDGRRHSRKGLATDWLNSL    497
HsCPR     RLQARYYSIASSSKVHPNSVHICAVVVEYETKAGR--INKGVATNWL---    494
           .*  *  **  *              .*. .       **. *  **

HsMTRR    VASVLQPNIHASHEDSGKALAPKISISPRTTNSFHLP-------DDPSIP    539
CeMTRR    R----------------IGDKVQVLGKEPARFRLPPLGMTKNSAGKLP    529
HsCPR     RAKE------PVGENGGRALVPMFVRKSQFRLPFK----------ATTP    527
                                .                *          *
             NADPH
HsMTRR    IIMVGPGTGIAPFIGFLQHREKLQEQHPDGNFGAMW-LFFGCRHKDRDYL    588
CeMTRR    LLMVGPGTGVSVFLSFLHFLRKLKQDSPSDFVDVPRVLFFGCRDSSVDAI    579
HsCPR     VIMVGPGTGVAPFIGFIQERAWLRQQGKE---VGETLLYYGCRRSDEDYL    574
          ..*******.. *. *.     *   ..           *..***    * .
                          NADPH      NADPH
HsMTRR    FRKELRHFLKHGILTHLKVSFSRDAPVGEEEAPAKYVQDNIQLHGQQVAR    638
CeMTRR    YMSELEMFVSEGILTDLIICESEQ--------KGERVQDGLRKYLDKVLP    621
HsCPR     YREELAQFHRDGALTQLNVAFSRE------QSHKVYVQHLLKQDREHLWK    618
           .  **  *   * ** *   . * *          **   .   ..
                  NADPH
HsMTRR    ILLQE-NGHIYVCGDAKNMAKDVHDALVQIISKEVGVEKLEAMKTLATLK    687
CeMTRR    FLTASTESKIFICGDAKGMSKDVWQCFSDIVASDQGIPDLEAKKKLMDLK    671
HsCPR     LI--EGGAHIYVCGDARNMARDVQNTFYDIVAELGAMEHAQAVDYIKKLM    666
              .  *..****. *..**   .*..    ..  .*    . *
             NADPH/FAD
HsMTRR    EEKRYLQDIWS    698
CeMTRR    KSDQYIEDVWG    682
HsCPR     TKGRYSLDVWS    677
            *  *.*
```

Fig. 4-2

```
HsMTRR    ---------------------------------------------------
CeMTRR    ---------------------------------------------------
HsCPR     MGDSHVDTSSTVSEAVAEEVSLFSMTDMILFSLIVGLLTYWFLFRKKKEE       50
                                                   FMN
HsMTRR    ------------------------MRRFLLLYATQQGQAKAIAEEMCE         24
CeMTRR    ------------------------MTDFLIAFGSQTGQAETIAKSLKE         24
HsCPR     VPEFTKIQTLTSSVRESSFVEKMKKTGRNIIVFYGSQTGTAEEFANRLSK       100
                                    .. ...* * *    *  ..
                                                FMN
HsMTRR    QAVVHGFSADLHCISESDK-YDLKT-------ETAPLVVVVSTTGTDPP        66
CeMTRR    KAELIGLTPRLHALDENEKKFNLNE-------EKLC-AIVVSSTGDGAP        66
HsCPR     DAHRYG----MRGMSADPEEYDLADLSSLPEIDNALVVFCMATYGEGDPT      146
           *    *         .  .....*..      .     ... * **
                                        FMN
HsMTRR    DTARKFVKEIQNQTLPVDFFAHLRYGLLGLGDSEYTYFCNGGKIIDKRLQ      116
CeMTRR    DNCARFVRRINRNSLENEYLKNLDYVLLGLGDSNYSSYQTIPRKIDKQLT      116
HsCPR     DNAQDFYDWLQETDVD---LSGVKFAVFGLGNKTYEHFNAMGKYVDKRLE      193
          *  * *   ..  .       ... ***. *   .   . .** *

HsMTRR    ELGARHFYDTGHADDCVGLELVVEPWIAGLWPALRKHFRSSRGQEEISGA      166
CeMTRR    ALGANRLFDRAEADDQVGLELEVEPWIEKFFATLASRFDISADKMN----      162
HsCPR     QLGAQRIFELGLGDDDGNLEEDFITWREQFWPAVCEHF---------GV       233
           ***    ...  .** **     *   . .        *

HsMTRR    LPVASPASLRTDLVKSELLHIESQVELL--RFDDSGRKDSEVLKQNAVNS      214
CeMTRR    -AITESSNLKLNQVKTE----EEKKALLQKRIEDEESDDEGRGRVIGID-      206
HsCPR     EATGEESSIRQYEL------------VVHTDIDAAKVYMGEMGRLKSYEN      271
              . ..   .         ..         .

HsMTRR    NQSNVVIEDF---ESSLTRSVPPLS-QASLNIPGLPPEYLQVHLQESLGQ      260
CeMTRR    ---MLIPEHYDYPEISLLKGSQTLSNDENLRVPIAPQPFIVSSVSNRKLP      253
HsCPR     QKP-----PFD----------------------AKNPFLAAVTTNRKLN      293
              .                                .. .

HsMTRR    EESQVS-------VTSADPVFQVPISKAVQLTT--NDAIKTTLLVELDIS      301
CeMTRR    EDTKLEWQNLCKMPGVVTKPFEVLVVSAEFVTDPFSKKIKTKRMITVDFG      303
HsCPR     QGTE-----------------------------------RHLMHLELD       306
           . .                                       .. ..

HsMTRR    N--TDFSYQPGDAFSVICPNSDSEVQSLLQR-LQLEDKREHCVLLKIKAD      348
CeMTRR    DHAAELQYEPGDAIYFCVPNPALEVNFILKRCGVLDIADQQCEL-SINPK      352
HsCPR     ISDSKIRYESGDHVAVYPANDSALVNQLGK---ILGADLD--VVMSLNNL      351
                 . *. **     *   *..    *         .   . .

HsMTRR    TKKKGATLPQHIPAGCSLQFIFTWCLEIRAIPKKAFLRALVDYTSDSAEK      398
CeMTRR    TEKINAQIPGHVHKITTLRHMFTTCLDIRRAPGRPLIRVLAESTSDPNEK      402
HsCPR     DEESNKKHP--FPCPTSYRTALTYYLDITNPPRTNVLYELAQYASEPSEQ      399
                     *  . ** *   *.. .  *     . *..*. *
```

Fig. 4-3

```
HsMTRR    RRLQEL--CSKQGAADYSRFVRDACACLLDLLLAFPSCQPPLSLLLEHLP          446
CeMTRR    RRLLEL--CSAQGMKDFTDFVRTPGLSLADMLFAFPNVKPPVDRLIELLP          450
HsCPR     ELLRKMASSSGEGKELYLSWVVEARRHILAILQDCPSLRPPIDHLCELLP          449
            *  .   * .*   . .*    . .*    *    **.   *  * **
                       FAD              FAD              FAD
HsMTRR    KLQPRPYSCASSSLFHPGKLHFVFNIVEFLSTATTEVLRKGVCTGWLALL          496
CeMTRR    RLIPRPYSMSS---YENRKARLIYSEMEFPATDGRRHSRKGLATDWLNSL          497
HsCPR     RLQARYYSIASSSKVHPNSVHICAVVVEYETKAGR--INKGVATNWL---          494
           .*  * **  *                   .*. .       **. *  **

HsMTRR    VASVLQPNIHASHEDSGKALAPKISISPRTTNSFHLP-------DDPSIP          539
CeMTRR    R-----------------IGDKVQVLGKEPARFRLPPLGMTKNSAGKLP          529
HsCPR     RAKE------PVGENGGRALVPMFVRKSQFRLPFK----------ATTP          527
                                          *                   *
                  NADPH
HsMTRR    IIMVGPGTGIAPFIGFLQHREKLQEQHPDGNFGAMW-LFFGCRHKDRDYL          588
CeMTRR    LLMVGPGTGVSVFLSFLHFLRKLKQDSPSDFVDVPRVLFFGCRDSSVDAI          579
HsCPR     VIMVGPGTGVAPFIGFIQERAWLRQQGKE---VGETLLYYGCRRSDEDYL          574
          ..*******.. *.*.          *  ..        *..***    * .
                       NADPH               NADPH
HsMTRR    FRKELRHFLKHGILTHLKVSFSRDAPVGEEEAPAKYVQDNIQLHGQQVAR          638
CeMTRR    YMSELEMFVSEGILTDLIICESEQ--------KGERVQDGLRKYLDKVLP          621
HsCPR     YREELAQFHRDGALTQLNVAFSRE------QSHKVYVQHLLKQDREHLWK          618
           .  **  *   *  ** *. * *           **        ..   ..
                  NADPH
HsMTRR    ILLQE-NGHIYVCGDAKNMAKDVHDALVQIISKEVGVEKLEAMKTLATLK          687
CeMTRR    FLTASTESKIFICGDAKGMSKDVWQCFSDIVASDQGIPDLEAKKKLMDLK          671
HsCPR     LI--EGGAHIYVCGDARNMARDVQNTFYDIVAELGAMEHAQAVDYIKKLM          666
           .     . *..****.*..**  .   .*..   ..    .*   .  *
                NADPH/FAD
HsMTRR    EEKRYLQDIWS       698
CeMTRR    KSDQYIEDVWG       682
HsCPR     TKGRYSLDVWS       677
               *  *.*
```

Fig. 4-4

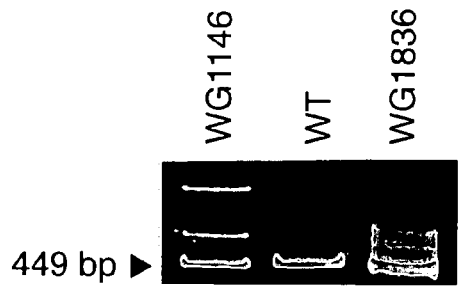

Fig. 7A

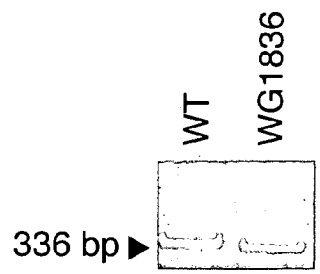

Fig. 7B

| Position | Sequence | Accession# | Protein | | Organism |
|---|---|---|---|---|---|
| 572 | GAMWLFFGCRHKDRDYLF | (AF025794) | MTRR | | (H sapiens) |
| 558 | GETLLYYGCRRSDEDYLY | (A60557) | CPR | | (H sapiens) |
| 559 | GETLLYYGCRRAAEDYLY | (D00101) | CPR | | (O cuniculus) |
| 560 | GESILYFGCRKSEDYIY | (X93090) | CPR | | (D melanogaster) |
| 572 | GPALLFFGCRNRQMDFIY | (P37116) | CPR | | (V radiata) |
| 573 | GPTVLFFGCRKSDEDFLY | (Z26938) | CPR | | (A niger) |
| 1281 | CPMVLVFGCRQSKIDHIY | (D16408) | NOS | I | (H sapiens) |
| 1009 | GRMTLVFGCRRPDEDHIY | (U05810) | NOS | II | (H sapiens) |
| 1040 | TPMTLVFGCRCSQLDHLY | (L26914) | NOS | III | (H sapiens) |
| 380 | GRMTLVFGCRHPEEDHLY | (U85094) | NOS | | (O cuniculus) |
| 1005 | GDMILLFGCRHPDMDHIY | (U46504) | NOS | | (G gallus) |
| 481 | GKNWLFFGNPHFTEDFLY | (M23008) | SR | | (E coli) |
| 915 | GEVFLYLGSRHKREEYLY | (L26503) | SR | | (S cerevisiae) |
| 407 | GRNWLIFGNRHFHRDFLY | (Z23169) | SR | | (T roseopersicina) |
| 261 | GLAWLFLGVANVDSLLYD | (X99419) | FNR | | (P sativum) |
| 251 | GLAWLFLGVPTSSSLLYK | (P00455) | FNR | | (S oleracea) |

Fig. 7C

HUMAN METHIONINE SYNTHASE REDUCTASE: CLONING, AND METHODS FOR EVALUATING RISK OF NEURAL TUBE DEFECTS, CARDIOVASCULAR DISEASE, AND CANCER

CROSS-REFERENCE TO RELATED APPLICATIONS

This application is a continuation-in-part of U.S. application Ser. No. 09/232,028 entitled "Methods for Evaluating Risk of Neural Tube Defects, Cardiovascular Disease, and Cancer" filed by Gravel et al. on Jan. 15, 1999, now abandoned, which claims priority from U.S. Provisional Application No. 60/071,622, filed Jan. 16, 1998.

FIELD OF THE INVENTION

This invention relates to the diagnosis and treatment of patients at risk for disorders associated with altered methionine synthase activity.

BACKGROUND OF THE INVENTION

Methionine is an essential amino acid in mammals that is required for protein synthesis. Methionine also plays a central role in metabolic reactions involving transfer of single-carbon moieties: in its activated form, S-adenosylmethionine, methionine is the methyl donor in hundreds of biological transmethylation reactions. Moreover, methionine is the propylamine donor in polyamine synthesis. The ultimate product resulting from the demethylation of methionine is homocysteine, the remethylation of which is catalyzed by a cobalamin-dependent enzyme, methionine synthase (5-methyltetrahydrofolate:homocysteine methyltransferase, EC 2.1.1.13).

The enzyme-bound cobalamin cofactor of methionine synthase plays an essential role in the methyl transfer reaction by acting as an intermediate methyl carrier between methyltetrahydrofolate and homocysteine. The upper portion of FIG. 1 illustrates the transfer of the methyl group of methyltetrahydrofolate ($CH_3$—THF) to homocysteine via methionine synthase-methylcobalamin [MetSyn-$CH_3$—Co(III)] as an intermediate methyl carrier. Cleavage of the methyl-cobalt bond of the methylcob(III)alamin intermediate occurs heterolytically so as to leave the cobalamin in the highly reactive cob(I)alamin oxidation state. The occasional oxidation of the enzyme-cobalamin to the cob(II)alamin state [MetSyn-Co(II)] renders the enzyme inactive.

Severe deficiency of methionine synthase activity leads to megaloblastic anemia, developmental delay, hyperhomocysteinemia, and hypomethioninemia. Moreover, elevated plasma homocysteine is a risk factor in cardiovascular disease and neural tube defects (Rozen, *Clin. Invest. Med.* 19:171–178, 1996).

Two forms of methionine synthase deficiency are known (Watkins et al., *Am. J. Med. Genet.* 34:427–434, 1989; Gulati et al., *J. Biol. Chem.* 272:19171–19175, 1997). The first is a primary defect of the amino acid sequence of the methionine synthase enzyme. We recently cloned cDNAs encoding human methionine synthase and showed that patients from the cblG complementation group of folate/cobalamin metabolism have mutations in the methionine synthase gene. A second class of patients, belonging to a distinct complementation group, cblE, is also deficient in methionine synthase enzymatic activity. The genetic basis of this deficiency has not been determined.

An analogous methylcobalamin-dependent methionine synthase has been well characterized in *E. coli* and the structures comprising its C-terminal half have been elucidated by X-ray crystallography. The reductive activation system required for its maintenance is a two-component flavoprotein system consisting of flavodoxin (a small FMN-containing electron transfer protein), and NADPH-ferredoxin (flavodoxin) oxidoreductase, a member of a family of electron transferases termed the "FNR family." However, flavodoxins are not found in mammalian cells.

It would be desirable to identify the enzyme that catalyzes the reductive activation of methionine synthase, i.e., the methionine synthase reductase. Knowledge of the reductase wild-type nucleotide and amino acid sequences would allow the identification of mutations and polymorphisms associated with diseases involving methionine metabolism. Moreover, an understanding of the reductase structure and function will facilitate the identification of compounds that modulate its activity. Such compounds will be useful in treating and preventing disease and developmental defects.

BRIEF DESCRIPTION OF THE DRAWINGS

FIG. 3 is a diagram showing the nucleotide and deduced amino acid sequence of human methionine synthase reductase.

FIG. 4 is a diagram showing an amino acid sequence comparison among human methionine synthase reductase (HsMTRR; SEQ ID NO: 21), *C. elegans* putative methionine synthase reductase (CeMTRR; SEQ ID NO: 22) and human cytochrome P450 reductase (HsCPR; SEQ ID NO: 23).

FIGS. 7A and 7B are representations of gels showing a mutation analysis of cblE patient cell lines.

FIG. 7C is a diagram showing a sequence comparison of the NADPH binding region of FNR family members (SEQ ID NOs: 25–40)

SUMMARY OF THE INVENTION

Figure 1:
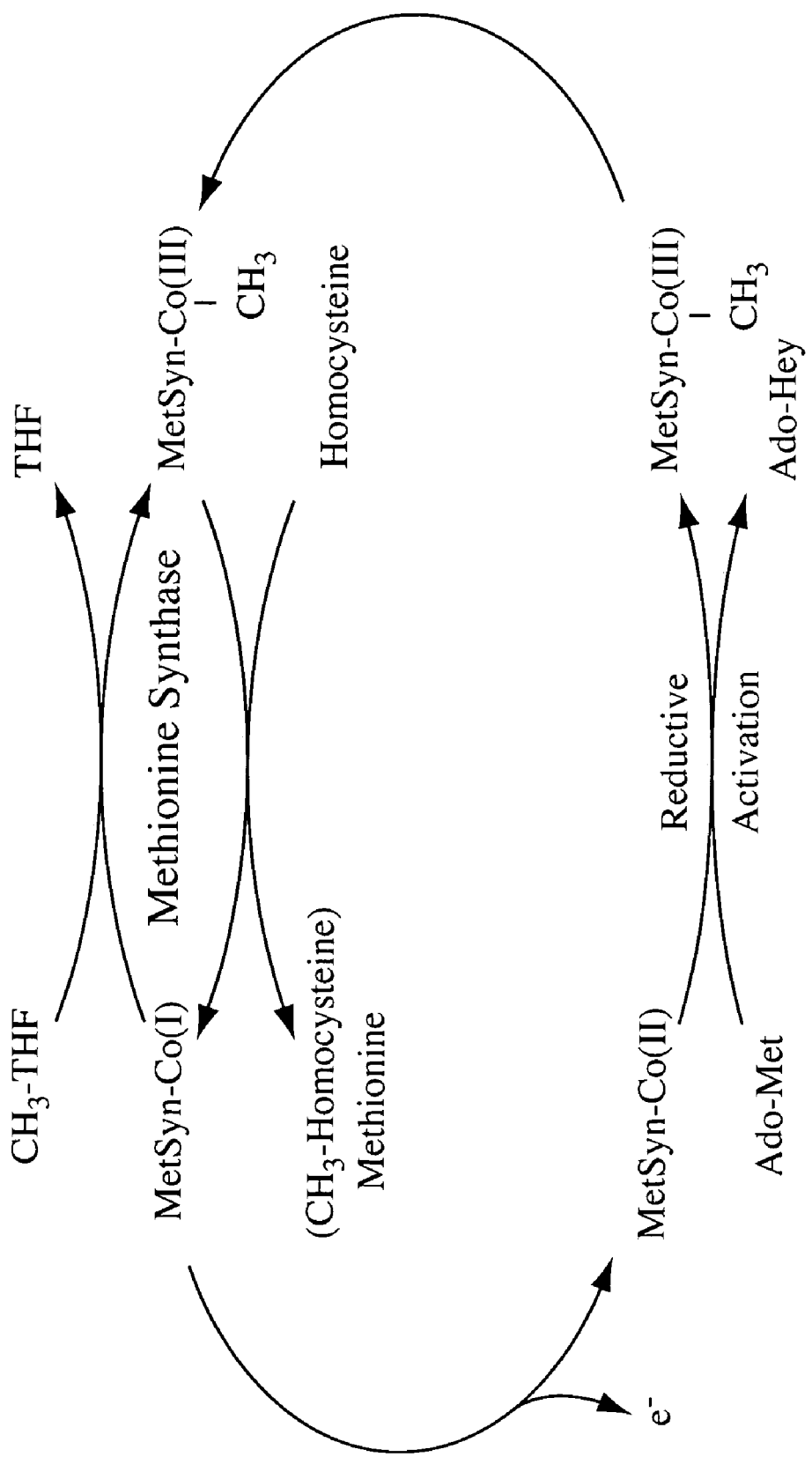
FIG. 1 is a diagram showing the enzymatic reaction that is catalyzed by methionine synthase, and the reductive reactivation of methionine synthase.

We have cloned the gene encoding human methionine synthase reductase. This enzyme maintains methionine synthase in its reduced, activated state, and hence is an essential component of the methionine synthetic pathway. Deficiency of methionine synthase reductase results in hyperhomocysteinemia, a condition that has been implicated in cardiovascular disease and neural tube defects. The presence of mutations in the methionine synthase reductase gene that decrease methionine synthase reductase enzymatic activity are likely to be associated with altered risk for cardiovascular disease, neural tube defects, and cancer. The invention features methods for risk detection and treatment of patients with hyperhomocysteinemia, cardiovascular disease, neural tube defects, and cancer. The invention also features compounds and kits which may be used to practice the methods of the invention, methods and compounds for treating or preventing these conditions and methods of identifying therapeutics for the treatment or prevention of these conditions.

In a first aspect, the invention features substantially pure nucleic acid encoding a mammalian methionine synthase reductase polypeptide. In various embodiments, the nucleic acid may encode a human polypeptide, and the nucleic acid may be DNA, particularly genomic DNA or cDNA. In another embodiment, the nucleic acid has the sequence of SEQ ID NO: 1 or SEQ ID NO: 41, or degenerate variants thereof, and the nucleic acid encodes the amino acid sequence of SEQ ID NO: 2 or SEQ ID NO: 42. In yet another embodiment, the nucleic acid is operably linked to regulatory sequences for expression of methionine synthase reductase. The regulatory sequences comprise a promoter, and the promoter may be inducible.

In a second, related aspect, the invention features a substantially pure nucleic acid that hybridizes at high stringency to the nucleic acid of SEQ ID NO: 1 or SEQ ID NO: 41. In a preferred embodiment, the nucleic acid is a naturally occurring variant of the mammalian methionine synthase reductase gene. In another embodiment, the nucleic acid has a sequence complementary to at least 50% of at least 60 nucleotides of the nucleic acid encoding the methionine synthase reductase polypeptide, and the sequence is sufficient to allow nucleic acid hybridization under high stringency conditions. In further embodiments, the nucleic acid may be a probe or an antisense nucleic acid, and the sequence may be complementary to at least 90% of at least 18 nucleotides of the nucleic acid encoding the methionine synthase reductase polypeptide.

In a third aspect, the invention features a nucleic acid encoding a mutant or polymorphic mammalian methionine synthase reductase polypeptide. In one embodiment, the nucleic acid may be from a human. In another embodiment, the mutation is a deletion mutation, for example, a deletion of 4 bases starting from base 1675 (bases 1675–1678) of SEQ ID NO:1 (SEQ ID NO: 47), or a deletion of 3 bases starting from base 1726 (bases 1726–1728) of SEQ ID NO:1 (SEQ ID NO: 45). In still another embodiment the polymorphism is a nucleotide transition from G to A at nucleotide position 66 (SEQ ID NO: 41), or from G to A at nucleotide position 110 (SEQ ID NO: 43). Other naturally-occurring variants associated with altered risk for hyperhomocysteinemia are also a feature of this aspect of the invention.

In a fourth, related aspect, the invention features a cell containing the nucleic acid of the third aspect of the invention. In various embodiments, the cell may be a prokaryotic cell, a eukaryotic cell, a yeast cell, or a mammalian cell.

In a fifth, related aspect, the invention features a non-human transgenic animal containing the nucleic acid of the third aspect of the invention. In one embodiment, the nucleic acid contains a mutation associated with hyperhomocysteinemia.

In a sixth, related aspect, the invention features a non-human animal wherein one or both genetic alleles encoding a methionine synthase reductase polypeptide are mutated. In one embodiment of this sixth aspect, one or both genetic alleles encoding a methionine synthase reductase polypeptide are disrupted, deleted, or otherwise rendered nonfunctional. In further embodiments of the fifth and sixth aspects, the animal may be a rodent (e.g., a mouse), or a nematode (e.g., *C. elegans*).

In a seventh, related aspect, the invention features a cell from the animal of the fifth and sixth aspects.

In an eighth aspect, the invention features a substantially pure mammalian methionine synthase reductase polypeptide. In various embodiments, the polypeptide may be recombinant, or may be a human polypeptide, or may be the polypeptide set forth in SEQ ID NO: 2 or SEQ ID NO: 42.

In a ninth, related aspect, the invention features a polypeptide having conservative amino acid substitutions relative to SEQ ID NO: 2 or SEQ ID NO: 42, and having methionine synthase reductase biological activity.

In a tenth, related aspect, the invention features a mutant or polymorphic polypeptide which has less methionine synthase reductase biological activity than the polypeptide of SEQ ID NO: 2. In preferred embodiments, the polypeptide has a frameshift resulting in a premature stop codon (e.g., SEQ ID NO: 48), or a deletion mutation, such as a deletion of Leu576 (SEQ ID NO: 46). In other preferred embodiments, the polypeptide may have an amino acid substitution, such as isoleucine instead of methionine at amino acid position 22 (SEQ ID NO: 42), or tyrosine instead of cysteine at amino acid position 37 (SEQ ID NO: 44).

In an eleventh, related aspect, the invention features a mutant or polymorphic polypeptide which has higher methionine synthase reductase biological activity than the polypeptide set forth in SEQ ID NO: 2.

In a twelfth aspect, the invention features an antibody that specifically binds a methionine synthase reductase polypeptide. In one embodiment, the polypeptide is a mutant or polymorphic polypeptide.

In a thirteenth, related aspect, the invention features a method of generating an antibody that specifically binds a methionine synthase reductase polypeptide. The method comprises administering a methionine synthase reductase polypeptide, or fragment thereof, to an animal capable of generating an immune response, and isolating the antibody from the animal. Preferred antibodies specifically bind mutant methionine synthase reductase polypeptides.

In a fourteenth, related aspect, the invention features a method of detecting the presence of a methionine synthase reductase polypeptide. The method comprises contacting a sample with the antibody that specifically binds a methionine synthase reductase polypeptide and assaying for binding of the antibody to the polypeptide.

In a fifteenth aspect, the invention features a method for detecting sequence variants for methionine synthase reductase in a mammal. The method comprises analyzing the nucleic acid of a test subject to determine whether the test subject contains a mutation or polymorphism in a methionine synthase reductase gene. The presence of the mutation or polymorphism is an indication that the animal has an increased or decreased likelihood of developing hyperhomocysteinemia, cardiovascular disease, neural tube defects, or cancer.

In one embodiment of the fifteenth aspect, primers used for detecting a mutation are selected from: 5'-CTCCT-GCTCGAACATCTTCCTAAA (SEQ ID NO: 3); 5'-AATA-GATAAT CCCTATCCTTATGCC (SEQ ID NO: 4); 5'-CCCTGGCTCCTAAGATATCCATC (SEQ ID NO: 5); 5'-CGAACAACAAA TTCTTTCCACTTACC (SEQ ID NO: 6); 5'-CAAGGTTGGTGGAA GTCGCGTTG (SEQ ID NO: 7); 5'-ATGCCTTGAAGTGAT GAGGAGGTTT (SEQ ID NO: 8); 5'-TTCCTACAACATAGAGAGAAACTC (SEQ ID NO: 9); 5'-TTGCACAAGGGCATCATGTACATC (SEQ ID NO: 10); 5'-AAACCTCC TCATCACTTCAAG-GCAT (SEQ ID NO: 11); 5'-CTTGCACACGAATATG GTCTGGG (SEQ ID NO: 12); 5'-TGGCATCACCTG-CATCCTTGAGG (SEQ ID NO: 13); 5'-GATGTACCTG-TAAATATTCTGGGGG (SEQ ID NO: 14); 5'-AATC-CACGGCTCAA CCACAAGTTC (SEQ ID NO: 15); 5'-CTCGAAATT AACCCTCACTAAAGGG (SEQ ID NO: 16); 5'-AACCCATACCGCAG GTGAGCAAA (SEQ ID NO: 17); 5'-TTTAGTACTTTCAGTCAAAAAA GCT-TAAT (SEQ ID NO: 18); 5'-ATAAACGACTTCAAGA GCTTGGAGC (SEQ ID NO: 19); or 5'-AGGTTTGGCAC-TAGTAAAGCTGACT (SEQ ID NO: 20).

In another embodiment of the fifteenth aspect of the invention, the method further comprises the step of using nucleic acid primers specific for the methionine synthase reductase gene. The primers are used for DNA amplification by the polymerase chain reaction. In yet another embodiment, the step further comprises the step of sequencing nucleic acid encoding methionine synthase reductase from the test subject. In still other embodiments, the analyzing includes single strand conformational polymorphism (SSCP) analysis, or the method is carried out by restriction fragment length (RFLP) polymorphism analysis. In further embodiments, the method is for the diagnosis of an altered risk for cardiovascular disease, neural tube defects, or cancer, such as colon cancer.

In a sixteenth aspect, the invention features a kit for the analysis of mammalian methionine synthase reductase nucleic acid. The kit comprises nucleic acid probes for analyzing the nucleic acid of a mammal, and the analyzing is sufficient to determine whether the mammal contains a mutation in the methionine synthase reductase nucleic acid. In a preferred embodiment the nucleic acid probes allow detection of mutations associated with hyperhomocysteinemia.

In a seventeenth aspect, the invention features a kit for the analysis of mammalian methionine synthase reductase polypeptides. The kit comprises antibodies for analyzing the methionine synthase reductase polypeptide of a mammal, and the analyzing is sufficient to determine whether the mammal contains a mutation in the methionine synthase reductase nucleic acid.

In an eighteenth aspect, the invention features a method of treating or preventing cancer, cardiovascular disease, or neural tube defects. The method comprises inhibiting methionine synthase reductase biological activity. In one embodiment, the mammal is pregnant. In other embodiments, the method comprises administering a therapeutically effective dose of a methionine synthase reductase inhibitor to a mammal. The inhibitor may be a methionine synthase reductase anti-sense nucleic acid, a peptide comprising a portion of a mammalian methionine synthase reductase polypeptide, or a small molecule.

In a nineteenth aspect, the invention features a method of treating or preventing cardiovascular disease. The method comprises administering to the subject a therapeutically effective dose of a metabolite or cofactor selected from the group: folate, cobalamin, S-adenosyl methionine, betaine, or methionine.

In a twentieth aspect, the invention features a method of preventing neural tube defects, cancer, or cardiovascular disease. The method comprises: a) detecting an increased risk of neural tube defects, cancer, or cardiovascular disease, wherein the detecting is performed by analyzing methionine synthase reductase nucleic acid from one or more test subjects selected from: a mammal; a potential parent, either male or female; a pregnant mammal; or a developing embryo or fetus, wherein the analyzing is done by the method of the fifteenth aspect of the invention; and b) exposing the mammal, potential parent, pregnant mammal, and/or developing embryo or fetus to a therapeutically effective dose of a metabolite or cofactor selected from the group: cobalamin; S-adenosyl methionine; betaine; or methionine, wherein the exposing is via the administration of the dose to the mammal, the potential parent, the pregnant mammal, and/or the developing embryo or fetus.

In a preferred embodiment of the eighteenth and twentieth aspects of the invention, the subject has been diagnosed as having a mutation or polymorphism in methionine synthase reductase.

In a twenty-first aspect, the invention features a method of screening for a compound that modulates methionine synthase reductase biological activity. The method comprises the steps of: a) contacting a sample containing wild-type, mutated, or polymorphic methionine synthase reductase with the compound, and b) assaying for methionine synthase reductase enzymatic activity, wherein increased enzymatic activity indicates an inducer of methionine synthase reductase biological activity, and decreased enzymatic activity indicates an inhibitor of methionine synthase reductase biological activity.

In a twenty-second aspect, the invention features a method for screening for a compound that modulates methionine synthase reductase biological activity. The method comprises the steps of: a) contacting a sample with the compound, and b) assaying for methionine synthase reductase expression, wherein increased expression indicates an inducer of methionine synthase reductase biological activity, and decreased expression indicates an inhibitor of methionine synthase reductase biological activity. The sample is selected from: purified or partially purified methionine synthase reductase, a cell lysate, a cell, a nematode, or a mammal. In preferred embodiments, the sample may be the animal or cell described by the fifth and sixth aspects of the invention. In other preferred embodiments, the screening may be for compounds useful for the treatment or prevention of cardiovascular disease or cancer, or for the prevention of neural tube defects.

In a twenty-third aspect, the invention features a method for detecting an increased risk of developing a neural tube defect in a mammalian embryo or fetus. The method includes detecting the presence of a polymorphic methionine synthase reductase (MTRR) in a test subject, wherein the polymorphic MTRR contains a methionine instead of an isoleucine at amino acid position 22, wherein the test subject is a future parent of the embryo or fetus, and wherein detection of a homozygous MTRR polymorphism in the future parent, embryo, or fetus, or detection of either a homozygous or heterozygous MTRR polymorphism in both future parents, indicates an increased risk of developing a neural tube defect in the embryo or fetus.

In various embodiments of the twenty-third aspect of the invention, the polymorphic MTRR may be detected by analyzing nucleic acid from the test subject. The nucleic acid may be genomic DNA or cDNA. The nucleic acid may contain a G instead of an A at the third position of the twenty-second codon (nucleotide position 66, relative to the first nucleotide of the start codon) of MTRR.

In another embodiment of the twenty-third aspect of the invention, the method may further include: a) PCR-amplifying a segment of MTRR nucleic acid using primers MSG108S (SEQ ID NO: 49) and AD292 (SEQ ID NO: 50), and b) digesting the product of the PCR amplification reaction with the restriction enzyme Nde I, wherein a PCR product that is digested by Nde I indicates an increased risk of developing a neural tube defect in a mammalian embryo or fetus.

In still other embodiments of the twenty-third aspect of the invention, the polymorphic MTRR may be detected by analyzing MTRR polypeptide from the test subject, and the test subject may be a future female parent of the embryo or fetus, or the test subject may be the embryo or fetus itself.

In yet further embodiments of the twenty-third aspect of the invention, the method may further include detecting the presence of a polymorphic methylenetetrahydrofolate reductase (MTHFR) in a test subject, the polymorphic MTHFR having a T instead of a C at a nucleotide position equivalent to position 677 of SEQ ID NO: 51, wherein detection of the polymorphic MTHFR indicates an increased risk of developing a neural tube defect in the embryo or fetus. The polymorphic MTHFR may be detected by analyzing nucleic acid or polypeptide from the test subject.

In still another embodiment of the twenty-third aspect of the invention, the method may further include measuring the level of cobalamin in the test subject, wherein a low cobalamin level indicates an increased risk of developing a neural tube defect in the embryo or fetus.

By "methionine synthase reductase," "methionine synthase reductase protein," or "methionine synthase reductase polypeptide" is meant a polypeptide, or fragment thereof, which has at least 43% amino acid sequence identity, or at least 53% sequence similarity, preferably at least 47% identity (or at least 57% similarity), more preferably at least 55% identity (or at least 65% similarity), yet more preferably at least 65% sequence identity (or at least 75% similarity), still more preferably at least 75% sequence identity (or at least 85% similarity) and most preferably at least 85% sequence identity (or at least 95% similarity) to the human methionine synthase reductase polypeptide of SEQ ID NO: 2 (see FIG. 4), over the length of the polypeptide or fragment thereof, or over the length of the human methionine synthase reductase polypeptide of SEQ ID NO: 2, whichever is shorter in length. It is understood that polypeptide products from splice variants of methionine synthase reductase gene sequences are also included in this definition. Preferably, the methionine synthase reductase protein is encoded by nucleic acid having a sequence which hybridizes to a nucleic acid sequence present in SEQ ID NO: 1 (human methionine synthase reductase cDNA) under stringent conditions. Even more preferably the encoded polypeptide also has methionine synthase reductase biological activity, or is a mutant or polymorphic form of methionine synthase reductase that is associated with an increased risk of disease.

By "methionine synthase reductase nucleic acid" or "methionine synthase reductase gene" is meant a nucleic acid, such as genomic DNA, cDNA, or mRNA, that encodes methionine synthase reductase, a methionine synthase reductase protein, methionine synthase reductase polypeptide, or portion thereof, as defined above.

By "mutant methionine synthase reductase," "methionine synthase reductase mutation(s)," "mutations in methionine synthase reductase," "polymorphic methionine synthase reductase," "methionine synthase reductase polymorphism(s)," "polymorphisms in methionine synthase reductase," is meant a methionine synthase reductase (MTTR) polypeptide or nucleic acid having a sequence that confers an increased risk of a disease phenotype or enhanced protection against a disease in at least some genetic and/or environmental backgrounds. An example of a disease-associated methionine synthase reductase polymorphism is the 22M polymorphism (SEQ ID NO: 2), which is associated with an increased risk for neural tube defects.

Any given methionine synthase reductase polymorphism may be associated with an increased risk for some diseases and a decreased risk for other dieseases. Increased or decreased disease risks associated with specific methionine synthase reductase mutations and polymorphisms are determined by methods known to those skilled in the art.

Such mutations may be naturally occurring, or artificially induced. They may be, without limitation, transition, transversion, insertion, deletion, frameshift, or missense mutations. A mutant methionine synthase reductase protein may have one or more mutations, and such mutations may affect different aspects of methionine synthase reductase biological activity (protein function), to various degrees. Alternatively, a methionine synthase reductase mutation may indirectly affect methionine synthase reductase biological activity by influencing, for example, the transcriptional activity of a gene encoding methionine synthase reductase, or the stability of methionine synthase reductase mRNA. For example, a mutant methionine synthase reductase gene may be a gene that expresses a mutant methionine synthase reductase protein or may be a gene which alters the level of methionine synthase reductase protein in a manner sufficient to confer a disease phenotype in at least some genetic and/or environmental backgrounds. The presence of polymorphic or mutant methionine synthase reductase may be determined by detecting polymorphic or mutant methionine synthase reductase nucleic acid or polypeptide, using methods that are known in the art.

By "biologically active" methionine synthase reductase is meant a methionine synthase reductase protein or methionine synthase reductase gene that provides at least one biological function equivalent to that of the wild-type methionine synthase reductase polypeptide or the methionine synthase reductase gene. Biological activity of a methionine synthase reductase polypeptide includes, but is not limited to, the ability to catalyze the reductive methylation of enzymatically inactive methionine synthase-cob(II) alamin to generate enzymatically active methionine synthase-cob(III)alamin-CH3. Preferably, a biologically active methionine synthase reductase will display activity equivalent to at least 20–30% of wild-type activity, more preferably, at least 35–50% of wild-type activity, still more preferably, 55–75% of wild-type activity, and most preferably, a biologically active methionine synthase reductase will display at least 80–90% of wild-type activity. A biologically active methionine synthase reductase also may display more than 100% of wild-type activity. Preferably, the biological activity of the wild-type methionine synthase reductase is determined using the methionine synthase reductase nucleic acid of SEQ ID NO: 1 or SEQ ID NO: 41 or methionine synthase reductase polypeptide of SEQ ID NO: 2 or SEQ ID NO: 42. The degree of methionine synthase reductase biological activity may be intrinsic to the methionine synthase reductase polypeptide itself, or may be modulated by increasing or decreasing the number of methionine synthase reductase polypeptide molecules present intracellularly.

By "high stringency conditions" is meant hybridization in 2×SSC at 40° C. with a DNA probe length of at least 40 nucleotides. For other definitions of high stringency conditions, see Ausubel et al., Current Protocols in Molecular Biology, pp. 6.3.1–6.3.6, John Wiley & Sons, New York, N.Y., 1998, hereby incorporated by reference.

By "analyzing" or "analysis" is meant subjecting a methionine synthase reductase nucleic acid or methionine synthase reductase polypeptide to a test procedure that allows the determination of whether a methionine synthase reductase gene is wild-type or mutant. For example, one could analyze the methionine synthase reductase genes of an animal by amplifying genomic DNA using the polymerase chain reaction, and then determining the DNA sequence of the amplified DNA.

By "probe" or "primer" is meant a single-stranded DNA or RNA molecule of defined sequence that can base pair to a second DNA or RNA molecule that contains a complementary sequence (the "target"). The stability of the resulting hybrid depends upon the extent of the base pairing that occurs. The extent of base-pairing is affected by parameters such as the degree of complementarity between the probe and target molecules, and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for methionine synthase reductase nucleic acid preferably will have at least 35% sequence identity, more preferably at least 45–55% sequence identity, still more preferably at least 60–75% sequence identity, still more preferably at least 80–90% sequence identity, and most preferably 100% sequence identity. Probes may be detectably-labelled, either radioactively, or non-radioactively, by methods well-known to those skilled in the art. Probes are used for methods involving nucleic acid hybridization, such as: nucleic acid sequencing, nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

By "pharmaceutically acceptable carrier" means a carrier which is physiologically acceptable to the treated mammal while retaining the therapeutic properties of the compound with which it is administered. One exemplary pharmaceutically acceptable carrier is physiological saline. Other physiologically acceptable carriers and their formulations are known to one skilled in the art and described, for example, in Remington's Pharmaceutical Sciences, (18$^{th}$ edition), ed. A. Gennaro, 1990, Mack Publishing Company, Easton, Pa.

By "substantially identical" is meant a polypeptide or nucleic acid exhibiting, over its entire length, at least 50%, preferably 85%, more preferably 90%, and most preferably 95% identity to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

By "identity" is meant that a polypeptide or nucleic acid sequence possesses the same amino acid or nucleotide residue at a given position, compared to a reference polypeptide or nucleic acid sequence to which the first sequence is aligned.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid; asparagine, glutamine; serine, threonine; lysine, arginine; and phenylalanine, tyrosine.

By "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is a methionine synthase reductase polypeptide that is at least 75%, more preferably at least 90%, and most preferably at least 99%, by weight, pure. A substantially pure methionine synthase reductase polypeptide may be obtained, for example, by extraction from a natural source (e.g., a fibroblast) by expression of a recombinant nucleic acid encoding a methionine synthase reductase polypeptide, or by chemically synthesizing the protein. Purity can be measured by any appropriate method, e.g., by column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides not only includes those derived from eukaryotic organisms but also those synthesized in *E. coli* or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transgene" is meant any piece of DNA that is inserted by artifice into a cell, and becomes part of the genome of the organism that develops from that cell. Preferably the coding region of the transgene is operably linked to one or more transcriptional regulatory elements, including a promoter (as defined below) that direct transgene expression. Such a transgene may comprise a gene which is partly or entirely heterologous (i.e., foreign) to the transgenic organism, or may represent a gene homologous to an endogenous gene of the organism.

By "transgenic" is meant any cell that includes a DNA sequence that is inserted by artifice into a cell and becomes part of the genome of the organism which develops from that cell. As used herein, the transgenic organisms are generally transgenic mammals (e.g., rodents such as rats or mice) and the DNA (transgene) is inserted by artifice into the genome. Transgenic organisms also may include transgenic nematodes, such as transgenic *Caenorhabditis elegans,* which are generated by methods known to those skilled in the art.

By "knockout mutation" is meant an alteration in the nucleic acid sequence that reduces the biological activity of the polypeptide normally encoded therefrom by at least 80% relative to the unmutated gene. The mutation may, without limitation, be an insertion, deletion, frameshift mutation, or a missense mutation. Preferably, the mutation is an insertion or deletion, or is a frameshift mutation that creates a stop codon.

By "transformation" is meant any method for introducing foreign molecules into a cell (e.g., a bacterial, yeast, fungal, algal, plant, insect, or animal cell). Lipofection, DEAE-dextran-mediated transfection, microinjection, protoplast fusion, calcium phosphate precipitation, retroviral delivery, electroporation, and biolistic transformation are just a few of the methods known to those skilled in the art which may be used.

By "transformed cell" is meant a cell (or a descendant of a cell) into which a DNA molecule encoding a methionine synthase reductase polypeptide has been introduced, by means of recombinant DNA techniques.

By "positioned for expression" is meant that the DNA molecule is positioned adjacent to a DNA sequence which directs transcription and translation of the sequence (i.e., facilitates the production of, e.g., a methionine synthase reductase polypeptide, a recombinant protein or a RNA molecule).

By "promoter" is meant a minimal sequence sufficient to direct transcription. Also included in the invention are those promoter elements which are sufficient to render promoter-dependent gene expression controllable for cell type-specific, tissue-specific, temporal-specific, or inducible by external signals or agents; such elements may be located in the 5' or 3' or intron sequence regions of the native gene.

By "operably linked" is meant that a gene and one or more regulatory sequences are connected in such a way as to permit gene expression when the appropriate molecules (e.g., transcriptional activator proteins) are bound to the regulatory sequences.

By "conserved region" is meant any stretch of six or more contiguous amino acids exhibiting at least 30%, preferably at least 50%, and most preferably at least 70% amino acid sequence identity between two or more reductase family members, (e.g., between human methionine synthase reductase and human cytochrome p450 reductase). An example of a conserved region within these two reductases is the NADPH binding region (FIG. 4).

By "detectably-labeled" is meant any means for marking and identifying the presence of a molecule, e.g., an oligo-nucleotide probe or primer, a gene or fragment thereof, or a cDNA molecule. Methods for detectably-labeling a molecule are well known in the art and include, without limitation, radioactive labeling (e.g., with an isotope such as $^{32}P$ or $^{35}S$) and nonradioactive labeling (e.g., chemiluminescent or fluorescent labeling, e.g., fluorescein labeling).

By "antisense" as used herein in reference to nucleic acids, is meant a nucleic acid sequence that is complementary to the coding strand of a gene, preferably, a methionine synthase reductase gene. An antisense nucleic acid is capable of preferentially decreasing the activity of a mutant methionine synthase reductase polypeptide encoded by a mutant methionine synthase reductase gene.

By "specifically binds" is meant that an antibody recognizes and binds a human methionine synthase reductase polypeptide, but does not substantially recognize and bind other non-methionine synthase reductase molecules in a sample, e.g., a biological sample, that naturally includes protein. A preferred antibody binds to the methionine synthase reductase polypeptide sequence of SEQ ID NO: 2 (FIG. 3).

By "neutralizing antibodies" is meant antibodies that interfere with any of the biological activities of a wild-type or mutant methionine synthase reductase polypeptide, for example, the ability of methionine synthase reductase to catalyze the transfer of a methyl group to methionine synthase-cobal(II)amin. The neutralizing antibody may reduce the ability of a methionine synthase reductase polypeptide to catalyze the transfer preferably by 10% or more, more preferably by 25% or more, still more preferably by 50% or more, yet preferably by 70% or more, and most preferably by 90% or more. Any standard assay for the biological activity of methionine synthase reductase may be used to assess potentially neutralizing antibodies that are specific for methionine synthase reductase.

By "expose" is meant to allow contact between an animal, cell, lysate or extract derived from a cell, or molecule derived from a cell, and a test compound.

By "treat" is meant to submit or subject an animal (e.g. a human), cell, lysate or extract derived from a cell, or molecule derived from a cell to a test compound.

By "test compound" is meant a chemical, be it naturally-occurring or artificially-derived, that is surveyed for its ability to modulate an alteration in reporter gene activity or protein levels, by employing one of the assay methods described herein. Test compounds may include, for example, peptides, polypeptides, synthesized organic molecules, naturally occurring organic molecules, nucleic acid molecules, and components thereof.

By "assaying" is meant analyzing the effect of a treatment, be it chemical or physical, administered to whole animals, cells, or lysates, extracts, or molecules derived therefrom. The material being analyzed may be an animal, a cell, a lysate or extract derived from a cell, or a molecule derived from a cell. The analysis may be for the purpose of detecting altered protein biological activity, altered protein stability, altered protein levels, altered gene expression, or altered RNA stability. The means for analyzing may include, for example, the detection of the product of an enzymatic reaction, (e.g., the formation of active methionine synthase or methionine as a result of methionine synthase reductase activity), antibody labeling, immunoprecipitation, and methods known to those skilled in the art for detecting nucleic acids.

By "modulating" is meant changing, either by decrease or increase, in biological activity.

By "a decrease" is meant a lowering in the level of biological activity, as measured by inhibition of: a) the formation of enzymatically active methionine synthase-cob (III)alamin-CH3 or methionine as a result of methionine synthase reductase activity; b) protein, as measured by ELISA; c) reporter gene activity, as measured by reporter gene assay, for example, lacZ/β-galactosidase, green fluorescent protein, luciferase, etc.; or d) mRNA, as measured by PCR relative to an internal control, for example, a "housekeeping" gene product such as β-actin or glyceraldehyde 3-phosphate dehydrogenase (GAPDH). In all cases, the decrease is preferably by at least 10% more preferably by at least 25%, still more preferably by at least 50%, and even more preferably by at least 70%.

By "an increase" is meant a rise in the level of biological activity, as measured by a stimulation of: a) the formation of methionine synthase-cob(III)alamin-CH3 or methionine as a result of methionine synthase reductase activity; b) protein, as measured by ELISA; c) reporter gene activity, as measured by reporter gene assay, for example, lacZ/β-galactosidase, green fluorescent protein, luciferase, etc.; or d) mRNA, as measured by PCR relative to an internal control, for example, a "housekeeping" gene product such as β-actin or glyceraldehyde 3-phosphate dehydrogenase (GAPDH). Preferably, the increase is by at least 10%, more preferably by at least 25%, still more preferably by at least 75%, even more preferably by 2-fold, and most preferably by at least 3-fold.

By "alteration in the level of gene expression" is meant a change in gene activity such that the amount of a product of the gene, i.e., mRNA or polypeptide, is increased or decreased, or that the stability of the mRNA or the polypeptide is increased or decreased.

By "reporter gene" is meant any gene that encodes a product whose expression is detectable and/or quantitatable by immunological, chemical, biochemical or biological assays. A reporter gene product may, for example, have one of the following attributes, without restriction: fluorescence (e.g., green fluorescent protein), enzymatic activity (e.g., lacZ/β-galactosidase, luciferase, chloramphenicol acetyltransferase), toxicity (e.g., ricin A), or an ability to be specifically bound by a second molecule (e.g., biotin or a detectably-labelled antibody). It is understood that any engineered variants of reporter genes, which are readily available to one skilled in the art, are also included, without restriction, in the forgoing definition.

By "protein" or "polypeptide" or "polypeptide fragment" is meant any chain of more than two amino acids, regardless of post-translational modification (e.g., glycosylation or phosphorylation), constituting all or part of a naturally-occurring polypeptide or peptide, or constituting a non-naturally occurring polypeptide or peptide.

By "missense mutation" is meant the substitution of one purine or pyrimidine base (i.e. A, T, G, or C) by another within a nucleic acid sequence, such that the resulting new codon may encode an amino acid distinct from the amino acid originally encoded by the reference (e.g. wild-type) codon.

By "deletion mutation" is meant the deletion of at least one nucleotide within a polynucleotide coding sequence. A deletion mutation alters the reading frame of a coding region unless the deletion consists of one or more contiguous 3-nucleotide stretches (i.e. "codons"). Deletion of a codon from a nucleotide coding region results in the deletion of an amino acid from the resulting polypeptide.

By "frameshift mutation" is meant the insertion or deletion of at least one nucleotide within a polynucleotide coding sequence. A frameshift mutation alters the codon reading frame at and/or downstream from the mutation site. Such a mutation results either in the substitution of the encoded wild-type amino acid sequence by a novel amino acid sequence, or a premature termination of the encoded polypeptide due to the creation of a stop codon, or both.

By "low serum cobalamin level" is meant a serum cobalamin concentration of less than 328 pmol/L in a child, fetus, or embryo that has a neural tube defect or is at risk for developing a neural tube defect, or a serum cobalamin concentration of less than 259 pmol/L in the mother or future parent of a child having a neural tube defect.

By "polymorphic methylenetetrahydrofolate reductase" or "mutant methylenetetrahydrofolate reductase" is meant methylenetetrahydrofolate reductase (MTHFR) polypeptide or nucleic acid having a sequence that confers an increased risk of a disease phenotype in at least some genetic and/or environmental backgrounds, for example, in combination with an MMTR polymorphism or mutation.

By "677→T polymorphism in MTHFR" is meant a substitution of cytosine in place of thymine in nucleic acid encoding MTHFR at a nucleotide position equivalent to MTHFR nucleotide position 677 as disclosed in Frosst et al. (*Nat. Genet.* 10:111–113, 1995) and in Genbank Accession No. U09806 (SEQ ID NO: 51).

By "future parent" is meant a male or female who has contributed or may potentially contribute genetic material (e.g., a sperm or an egg) to form a zygote. A future parent is also a female who gestates or may potentially gestate an embryo or fetus in her uterus, irrespective of whether she has contributed or may potentially contribute genetic material to the embryo or fetus; an example of such a future parent is a surrogate mother).

By "test subject" is meant a future parent as defined above, an embryo, or a fetus.

By "sample from a test subject" is meant a specimen, for example, and not limited to, blood, serum, cells, or amniotic fluid, that would allow one of skill in the art to determine whether the test subject has a mutant or polymorphic methionine synthase reductase.

DETAILED DESCRIPTION OF THE INVENTION

Methionine synthase catalyzes the remethylation of homocysteine to methionine in a reaction in which methylcobalamin serves as an intermediate methyl carrier.

Over time, the cob(I)alamin cofactor of methionine synthase may become oxidized to cob(II)alamin, thus rendering the enzyme inactive. Regeneration of the functional enzyme occurs through the reductive methylation of the cob(II) alamin in a reaction in which S-adenosylmethionine is utilized as methyl donor (FIG. 1). The reductive activation system in the lower part of the scheme shown in FIG. 1 is the mechanism by which S-adenosylmethionine (Ado-Met) together with an electron reactivates the enzyme to the functional, methionine synthase-CH3-Co(III) state, resulting in the formation of S-adenosylhomocysteine (Ado-Hcy) as a reaction by-product.

Patients of the cblE complementation group of disorders of folate/cobalamin metabolism, who are defective in the reductive activation of methionine synthase, have megaloblastic anemia, developmental delay, hyperhomocysteinemia, and hypomethioninemia. We have cloned a cDNA corresponding to the "methionine synthase reductase" reducing system required for maintenance of the methionine synthase in a functional state. Using primers comprising sequences of consensus binding sites for FAD, FMN and NADPH, we performed RT-PCR and inverse PCR to clone a methionine synthase reductase cDNA. The cDNA hybridizes to an mRNA of 3.6 kb (as detected by Northern blot). The deduced protein is a novel member of the FNR family of electron transferases, containing 698 amino acids with a predicted Mr of 77,700. It shares 38% identity with human cytochrome P450 reductase and 43% with the *C. elegans* putative methionine synthase reductase (see below). Methionine synthase reductase was localized to human chromosome 5p15.2-15.3 by fluorescence in situ hybridization (FISH).

A survey of the NCBI databases for homology to the human methionine synthase reductase using BLASTP or TBLASTN yielded the putative methionine synthase reductase of *C. elegans* (P value=9×10-92). Proteins of the FNR family were also found using the BLAST programs. The strongest homology was found with cytochrome P450 reductase (P values>3×10-68), followed by nitric oxide synthase (three isoforms, P values>4×10-52), and sulfite reductase (P values> 6×10-39). Lower, but still significant homology was found with *E. coli* NADPH-ferredoxin(flavodoxin) reductase (P values>2×10-9) and flavodoxin (P values>3×10-2). Our finding suggests a convergent evolution of the two-gene flavodoxin/NADPH-ferredoxin(flavodoxin) reductase system to a single gene encoding a fused version of the two proteins in human cells. Alignment of the proteins provides for a large linker region bridging the two components.

The identity of our cloned cDNA sequence as that encoding methionine synthase reductase was confirmed by the identification of mutations in the corresponding gene in cblE patients having a functional deficiency of methionine synthase. Our key finding confirming the identification of the cDNA was a 4 bp frameshift mutation in two affected siblings. The occurrence of a functionally null mutation in a candidate gene provides compelling evidence that the mutation is causative of disease in the affected patients. Furthermore, a 3 bp deletion detected in a third patient is also highly likely to cause an enzyme defect, and the direct sequencing of PCR products suggested that the patient's second allele contains a mutation that renders the mRNA very unstable or poorly transcribed. In all, seven of ten tested cblE cell lines showed evidence of mutation although the sequence changes have yet to be determined in the remaining four.

The two mutations we have identified associated with cblE disease are located in the vicinity of the NADPH binding domain by comparison with proteins of the FNR family. The 4 bp deletion yields a truncated protein that is expected to be deficient in NADPH binding and possibly in FAD binding, since the C-terminus of the enzyme may be involved in both. The 3 bp deletion results in the deletion of Leu576, which is located between two sequences that may be involved in NADPH binding. Leu576 is well conserved among reductases that are similar to the methionine synthase reductase (FIG. 6C). This supports the idea that deletion of the Leu576 codon (1726delTTG) results in an enzymatic defect, although confirmation will require expression of the mutant protein. This residue is also conserved in the NADPH-ferredoxin (flavodoxin) reductase enzymes of several organisms, although the homology with this portion of the protein is low or absent in some cases. It is possible that the deletion affects the relationship between the two NADPH-binding sequences that are in its vicinity.

The cloning of human methionine synthase reductase cDNA enables the determination of the enzymatic mechanism involved in the reductive activation of methionine synthase. Furthermore, it is now possible to identify additional mutations in patients with severe deficiency of the enzyme activity, and to determine whether there exist common amino acid polymorphisms which lead to mildly elevated homocysteine levels. Such elevations may be a risk factor in cardiovascular disease, neural tube defects, and cancer.

Mutations in the human methionine synthase reductase gene that result in altered homocysteine and/or folate levels may be risk factors for the diseases listed above. The methods of the invention therefore provide diagnostic assays for such risk factors, as well as methods of treating or preventing cardiovascular disease, neural defects, cancer, megaloblastic anemia, and hypomethioninemia. In addition, the invention provides methods for screening assays for the isolation of potential therapeutic compounds that modulate methionine synthase reductase activity.

The assays described herein can be used to test for compounds that modulate methionine synthase activity and hence may have therapeutic value in the prevention of neural tube defects, prevention and/or treatment of cancer, cardiovascular disease, homocysteinemia, and megaloblastic anemia.

Test Compounds

In general, novel drugs for prevention of neural tube defects, or prevention and/or treatment of cancer, cardiovascular disease, and megaloblastic anemia are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their therapeutic activities for homocysteinemia, megaloblastic anemia, cardiovascular disease, cancer, and neural tube defects should be employed whenever possible.

When a crude extract is found to modulate methionine synthase reductase biological activity, further fractionation of the positive lead extract is necessary to isolate chemical constituents responsible for the observed effect. Thus, the goal of the extraction, fractionation, and purification process is the careful characterization and identification of a chemical entity within the crude extract that modulates methionine synthase reductase biological activity. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using mammalian models of homocysteinemia, megaloblastic anemia, cardiovascular disease, cancer, and neural tube defects.

Methionine Synthase Reductase Assays for the Detection of Compounds that Modulate Methionine Synthase Reductase Activity and Expression Potentially useful therapeutic compounds that modulate (e.g. increase or decrease) methionine synthase reductase activity or expression may be isolated by various screens that are well-known to those skilled in the art. Such compounds may modulate methionine synthase reductase expression at the pre- or post-transcriptional level, or at the pre- or post-translational level.

A. Screens for Compounds that Modulate Methionine Synthase Reductase Enzymatic Activity Screens for potentially useful therapeutic compounds that modulate methionine synthase reductase activity may be readily performed. For example, the effect of a test compound on methionine synthase reductase activity may be determined by measuring formation of $^{14}CH_3$-cob(III)alamin, which results from the transfer of $^{14}CH_3$ from S-adenosylmethionine to methionine synthase-cob(II)alamin. A test compound that increases the enzymatic activity of a methionine synthase reductase would result in increased levels of methionine synthase-$^{14}CH_3$-cob(III)alamin, and a compound that decreases the enzymatic activity of a methionine synthase reductase would result in decreased levels of methionine synthase-$^{14}CH_3$-cob(III)alamin.

The effect of a test compound on methionine synthase reductase activity also may be determined by measuring the resulting activity of methionine synthase. The amount of reaction product (i.e., methionine) formation reflects the relative activity of methionine synthase, which in turn reflects the relative activity of methionine synthase reductase, which in turn indicates the effect of the test compound on methionine synthase reductase activity. For example, a sample containing methionine synthase and homocysteine may contain a mutant, inactive methionine synthase reductase which does not reduce oxidized methionine synthase, and hence, no methionine is formed. However, a test compound that increases the enzymatic activity of the mutant methionine synthase reductase will result in increased levels of methionine formation, relative to control samples not containing the test compound. Analogously, a compound that decreases methionine synthase reductase activity will result in the formation of decreased levels of methionine formation in reactions containing active methionine synthase reductase. That a test compound directly modulates methionine synthase reductase enzymatic activity, as opposed to methionine synthase enzymatic activity, can be confirmed by including control reactions that lack methionine synthase reductase. Such control reactions should not show altered levels of methionine production if the test compound directly modulates methionine synthase reductase activity.

Examples of methionine synthase activity assays, in vitro and in whole cells, are well-known to those skilled in the art (see, for example, Gulati et al., 1997, *J. Biol. Chem.* 272: 19171–19175; see also Rosenblatt et al., 1984, *J. Clin. Invest.* 74:2149–2156).

B. ELISA for the Detection of Compounds that Modulate Methionine Synthase Reductase Expression Enzyme-linked immunosorbant assays (ELISAs) are easily incorporated into high-throughput screens designed to test large numbers of compounds for their ability to modulate levels of a given protein. When used in the methods of the invention, changes in a given protein level of a sample, relative to a control, reflect changes in the methionine synthase reductase expression status of the cells within the sample. Protocols for ELISA may be found, for example, in Ausubel et al., *Current Protocols in Molecular Biology*, John Wiley & Sons, New York, N.Y., 1997. Lysates from cells treated with potential modulators of methionine synthase reductase expression are prepared (see, for example, Ausubel et al., supra), and are loaded onto the wells of microtiter plates coated with "capture" antibodies specific for methionine synthase reductase. Unbound antigen is washed out, and a methionine synthase reductase-specific antibody, coupled to an agent to allow for detection, is added. Agents allowing detection include alkaline phosphatase (which can be detected following addition of calorimetric substrates such as p-nitrophenolphosphate), horseradish peroxidase (which can be detected by chemiluminescent substrates such as ECL, commercially available from Amersham) or fluorescent compounds, such as FITC (which can be detected by fluorescence polarization or time-resolved fluorescence). The amount of antibody binding, and hence the level of a methionine synthase reductase polypeptide within a lysate sample, is easily quantitated on a microtiter plate reader.

As a baseline control for methionine synthase reductase expression, a sample that is not exposed to test compound is included. Housekeeping proteins are used as internal standards for absolute protein levels. A positive assay result, for example, identification of a compound that increases or decreases methionine synthase reductase expression, is indicated by an increase or decrease in methionine synthase reductase polypeptide within a sample, relative to the methionine synthase reductase level observed in cells which are not treated with a test compound.

C. Reporter Gene Assays for Compounds that Modulate Methionine Synthase Reductase Expression Assays employing the detection of reporter gene products are extremely sensitive and readily amenable to automation, hence making them ideal for the design of high-throughput screens. Assays for reporter genes may employ, for example, calorimetric, chemiluminescent, or fluorometric detection of reporter gene products. Many varieties of plasmid and viral vectors containing reporter gene cassettes are easily obtained. Such vectors contain cassettes encoding reporter genes such as lacZ/β-galactosidase, green fluorescent protein, and luciferase, among others. Cloned DNA fragments encoding transcriptional control regions of interest (e.g. that of the mammalian methionine synthase reductase gene) are easily inserted, by DNA subcloning, into such reporter vectors, thereby placing a vector-encoded reporter gene under the transcriptional control of any gene promoter of interest. The transcriptional activity of a promoter operatively linked to a reporter gene can then be directly observed and quantitated as a function of reporter gene activity in a reporter gene assay.

Cells are transiently- or stably-transfected with methionine synthase reductase control region/reporter gene constructs by methods that are well known to those skilled in the art. Transgenic mice containing methionine synthase reductase control region/reporter gene constructs are used for late-stage screens in vivo. Cells containing methionine synthase reductase/reporter gene constructs are exposed to compounds to be tested for their potential ability to modulate methionine synthase reductase expression. At appropriate timepoints, cells are lysed and subjected to the appropriate reporter assays, for example, a calorimetric or chemiluminescent enzymatic assay for lacZ/β-galactosidase activity, or fluorescent detection of GFP. Changes in reporter gene activity of samples treated with test compounds, relative to reporter gene activity of appropriate control samples, indicate the presence of a compound that modulates methionine synthase reductase expression.

D. Quantitative PCR of Methionine Synthase Reductase mRNA as an Assay for Compounds that Modulate Methionine Synthase Reductase Expression The polymerase chain reaction (PCR), when coupled to a preceding reverse transcription step (rtPCR), is a commonly used method for detecting vanishingly small quantities of a target mRNA. When performed within the linear range, with an appropriate internal control target (employing, for example, a housekeeping gene such as actin), such quantitative PCR provides an extremely precise and sensitive means of detecting slight modulations in mRNA levels. Moreover, this assay is easily performed in a 96-well format, and hence is easily incorporated into a high-throughput screening assay. Cells are treated with test compounds for the appropriate time course, lysed, the mRNA is reverse-transcribed, and the PCR is performed according to commonly used methods, (such as those described in Ausubel et al., *Current Protocols in Molecular Biology*, John Wiley & Sons, New York, N.Y., 1997), using oligonucleotide primers that specifically hybridize with methionine synthase reductase nucleic acid. Changes in product levels of samples exposed to test compounds, relative to control samples, indicate test compounds that modulate methionine synthase reductase expression.

Secondary Screens of Test Compounds that Appear to Modulate Methionine Synthase Reductase Activity After test compounds that appear to have methionine synthase reductase-modulating activity are identified, it may be necessary or desirable to subject these compounds to further testing. At late stages testing will be performed in vivo to confirm that the compounds initially identified to affect methionine synthase reductase activity will have the predicted effect in vivo. Such tests may be performed using cells or animals that have wild-type, mutated, or deleted methionine synthase reductase genes, or wild-type or mutated methionine synthase reductase transgenes.

Therapy

Compounds identified using any of the methods disclosed herein, may be administered to patients or experimental animals with a pharmaceutically-acceptable diluent, carrier, or excipient, in unit dosage form. Conventional pharmaceutical practice may be employed to provide suitable formulations or compositions to administer such compositions to patients or experimental animals. Although intravenous administration is preferred, any appropriate route of administration may be employed, for example, parenteral, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds.

Other potentially useful parenteral delivery systems for antagonists or agonists of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The following examples are to illustrate, not limit the invention.

EXAMPLE 1

General Methods

Materials

Radiolabeled compounds were from DuPont (Wilmington, Del.). A human multiple tissue Northern blot and β-actin probe were from Clontech (Palo Alto, Calif.). The random-primed DNA labelling kit was from Boehringer Mannheim (Indianapolis, Ind.). The T/A cloning kit was from Invitrogen (Carlsbad, Calif.), the Geneclean III kit was obtained from Bio 101 Inc. (Vista, Calif.), and the Wizard Mini-Preps were from Promega (Madison, Wis.). Taq polymerase, AMV reverse transcriptase, Trizol reagent, and were purchased from Gibco BRL (Gaithersburg, Md.), and restriction enzymes were purchased from GibCo BRL and New England Biolabs (Beverly, Mass.). The Sequenase kits for manual sequencing of crude PCR products or plasmids were from United States Biochemicals (Cleveland, Ohio). The oligonucleotides (SEQ ID NOs: 3–20 and 49–50) were synthesized by ACGT Corporation (Toronto, Canada) or by the Sheldon Biotechnology Centre, McGill University. The sequences of oligonucleotides are shown in Table 1 and in FIG. 2. A human cDNA library, made in Lambda-ZAP from RNA derived from the human colon carcinoma line Caco-2, was used as template in some PCR reactions to obtain 5' extensions of the cDNA.

Homology Matches

Comparisons were made between putative FMN, FAD and NADPH binding sites and sequences in the NCBI databases (dbEST and nr) using the BLAST programs (Altschul et al., *Nat. Genet.* 6:119–129, 1994). The cytochrome P450 reductase and nitric oxide synthase full sequences were also used for homology searching.

PCR Cloning and DNA Sequencing

Total cellular RNA was isolated by the method of Chirgwin et al. (*Biochemistry*, 18:5294–5299, 1979) and reverse-transcribed using oligo-dT15 as primer. PCR was conducted as described previously (Triggs et al., *Am. J. Hum. Genet.* 49:1041–1054, 1991). The PCR products were purified using Geneclean, subcloned in the pCR2.1 vector and transformed into *E. coli* according to the supplier's protocol (TA cloning kit). The resulting clones were sequenced manually to confirm the specificity of PCR products. Automated sequencing was done by Bio S&T Inc. (Montreal, Canada) or by the DNA Sequencing Core Facility of the Canadian Genetic Diseases Network.

Northern Blot

The multiple tissue Northern blot, prepared from poly (A)+ RNA (2 μg/lane) of the indicated human tissues, was probed with an EcoRI segment of a subclone in pCRII containing an insert spanning positions 335–2148 of the methionine synthase reductase cDNA. Hybridization with human β-actin cDNA served as a control for the quantity and integrity of the RNA in the blot.

Chromosomal Localization

We performed PCR analysis of DNA from the NIGMS human/rodent somatic cells hybrid mapping panel (#2). The oligonucleotide primers, which were specific for the 3'-UTR region of the gene, amplified a 111 nucleotide product (accession #G19837 in dbSTS). A P1-derived artificial chromosome (PAC) clone (104K2) was identified from a total human genomic library (Ioannou, P. A. et al., *Nat. Genet.* 6:84–89, 1994) by hybridization screening with a methionine synthase reductase cDNA probe (clone 704947, accession #AA279726 in dbEST) and this genomic clone was then used for FISH mapping (Heng, H. H. et al., *Proc. Natl. Acad. Sci. USA* 89:9509–9513, 1992; Heng, H. H and Tsui, L. C., *Chromosoma* 102:325–332, 1993).

Cell Lines

Ten fibroblast cell lines from patients with homocystinuria (cblE complementation group) were used to identify mutations and polymorphisms in the MTRR gene using reverse transcription-PCR of total cellular RNA. Three of the cell lines displayed mutations: WG788 from the original cblE patient (Schuh et al., *N. Engl. J. Med.* 310:686–690, 1984); WG1146 from his younger brother, who had been diagnosed before birth, and whose mother was treated with hydroxocobalamin during pregnancy (Rosenblatt et al., *Lancet* 1: 1127–1129, 1985); and WG1836 from a patient who had previously been described as having dihydrofolate reductase deficiency (case 1 in Tauro et al., *N. Engl. J Med.* 294:466, 1976) and subsequently as having a "new mutation" associated with low methylcobalamin levels and reduced cellular folate uptake (Brasch et al, Aust. *N. Z. J. Med.* 18 Supp.434, 1988). In our laboratory, we have shown that the fibroblast line from this last patient falls into the cblE complementation group.

The fibroblast cell line WG1401 was the first to show the polymorphism, an A to G substitution at bp 66. WG1401 is from patient B.S.S. 17, with megaloblastic anemia, hyperhomocysteinemia, and mild methylmalonic aciduria. The polymorphism was also found in a control cell line, MCH64.

Twenty-two other cell lines were used as normal controls for mutation analysis.

Mutation Analysis by RT-PCR of Fibroblast RNA

Total cellular RNA was isolated from fibroblast pellets (Chirgwin et al., *Biochemistry*, 18:5294–5299, 1979). It was reverse transcribed using 25 µg total RNA in reactions containing 2.5 U of AMV reverse transcriptase and 500 ng of methionine synthase reductase-specific terminal oligonucleotide 2101C (SEQ ID NO: 20; Table 1) in a total reaction volume of 54 µl. The resultant cDNA was used as template for PCR. PCR for nine overlapping cDNA segments was performed in reactions containing 3 µl of template, 1 µl each of dTTP, dGTP, dATP and dCTP (10 mM), and 3 U Taq polymerase in a 46 µl volume. PCR products were verified by agarose gel electrophoresis before testing for heteroduplex formation. Heteroduplex analysis was carried out by mixing mutant and control PCR products 1:1, heating the mixture to 95° C. for 3 min, cooling to room temperature, and subjecting the samples to electrophoresis on an 8% polyacrylamide gel. Fragments displaying shifts were subcloned and sequenced, or sequenced directly.

MMTR Polymorphism Analysis in Genomic DNA Samples

For the screening of genomic DNA samples, restriction digestion analysis was performed with an artificially-created NdeI restriction site using the sense primer MSG108S 5'GCAAAGGCCATCGCAGAAGACAT (SEQ ID NO: 49) and antisense primer AD292 5'GTGAAGATCTGCAGAAAATCCATGTA (SEQ ID NO: 50), where the underlined C replaces the A to generate an NdeI restriction site in the normal sequence. To test for the mutation, 10 µl of PCR product was digested by adding 6 µl H2O, 2 µl New England Biolab's (NEB) buffer 4 and 2 µl NdeI. The PCR fragment of 66 bp remains uncut in the presence of the G (methionine) allele, but is digested into fragments of 44 bp and 22 bp in the presence of the A (isoleucine) allele.

Subjects

Patients with spina bifida (n=56) and mothers of children with spina bifida (n=58) were recruited from the Montreal Children's Hospital after approval of the protocol by the Institutional Review Board. The controls (n=97) were other outpatients who were having a venipuncture at the Pediatric Test Center, Montreal Children's Hospital, and who were with their mothers (n=89). Blood samples were obtained from mothers and children after appropriate consent. Exclusion criteria were syndromic neural tube disorder (NTD) cases, severe anemia, neoplastic disease, renal insufficiency and immunosuppressive therapy. Individuals who were taking vitamin supplements were also excluded. The methylenetetrahydrofolate reductase (MTHFR) genotypes and the levels of plasma homocysteine and serum cobalamin were previously determined in these subjects. The concentration of serum cobolamin was quantitated by routine methods, using an automated system and reagents from Ciba (Ciba Corning Diagnostics Corp., Medfield, Mass.).

To determine total homocysteine (tHcy) levels in plasma, blood samples were drawn to Becton-Dickinson vacutainers containing sodium EDTA and kept on ice until plasma was separated. Plasma was separated by centrifugation for 5 min., removed, and cetrifuged again; the supernatant was collected and frozen at −20° C. until analysis. tHcy in plasma was determined by high pressure liquid chromatography as reported (Gilfix et al., *Clin. Chem.* 43:687–688, 1997). The tHcy adduct was detected by fluorescence after precolumn derivitization with the thiol-specific reagent 7-fluoro-benzo-2-oxa-1,3-diazole-4-sulphonate (SBD-F) (Wako, USA).

To detect the MTHFR polymorphism, DNA was isolated from peripheral leukocytes by extraction with phenol-chloroform after cell lysis in a buffer containing Nonidet-P40 (Boehringer Mannheim, Mannheim, Germany) and stored at −20° C. The presence of the 677C→T polymorphism in MTHFR (SEQ ID NO: 51) was determined by PCR followed by restriction digestion with HinfI, as described (Frosst et al., *Nat. Genet.* 10:111–113, 1995).

Statistics

Computer-assisted statistical analyses were carried out using SAS for Windows (Version 6.12). Standard summary statistics, analysis of variance, t-tests, calculation of odds ratios with associated confidence limits, and logistic regression models were used where appropriate. Statistical significance was interpreted as p-values of $p<0.05$.

EXAMPLE II

Cloning of the Human Methionine Synthase Reductase cDNA

Figure 2:
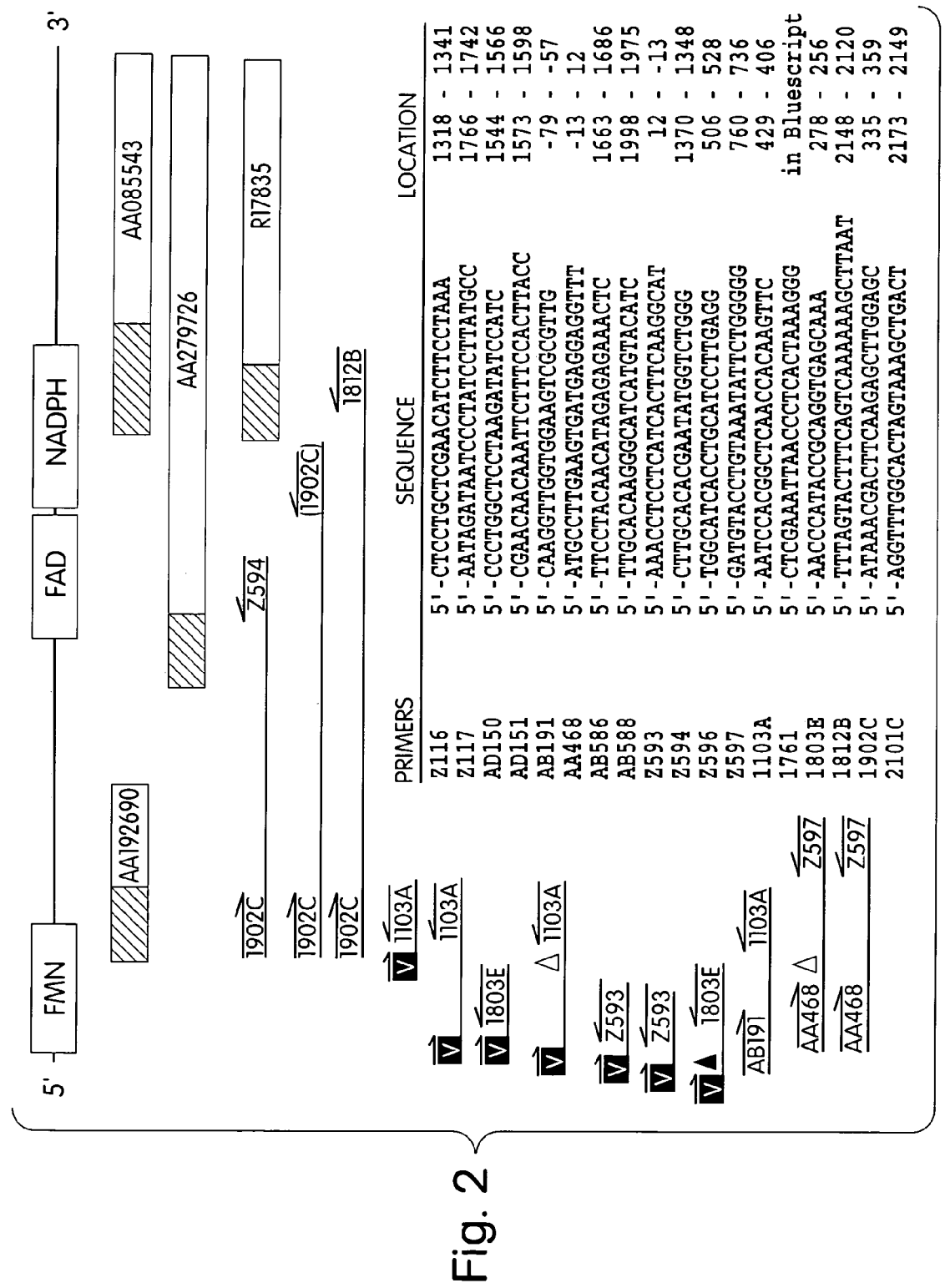
FIG. 2 is a diagram showing the overlapping clones and PCR fragments used to clone and sequence human methionine synthase reductase.

More than 20 overlapping sequences homologous to the FAD and NADPH-binding domains of cytochrome P450 reductase were identified in an initial survey of the NCBI dbEST database using TblastN. We sequenced clones 550341 (accession #AA085543), 704947 (accession #AA279726) and 31776 (accession #R17835) to confirm the sequence of this part of the cDNA. Reprobing the NCBI databases with this sequence yielded a *C. elegans* sequence (accession #Z35595) containing binding sites for FMN, FAD and NADPH. We then used the *C. elegans* sequence to reprobe the dbEST database using TblastN and identified a human sequence (accession #AA192690, clone 628497) containing a putative FMN binding site similar to the one encoded by Z35595. We designed a sense primer based on the FMN binding region of AA192690 and antisense primers corresponding to the FAD/NADPH binding regions of the methionine synthase reductase candidate and amplified a sequence by RT-PCR using human fibroblasts as the source of RNA. FIG. 2 shows the overlapping clones and PCR fragments used to clone and sequence human methionine synthase reductase. The EST clones are shown as rectangles, the subsequences that were available from the dbEST database are shown as hatched boxes, and the PCR fragments are represented as lines. The oligonucleotide names are indicated below the arrows in FIG. 2 and are described in Table 1 below. The primer in parentheses designates a mispriming outcome that generated valid internal sequence. The letter "V" in black boxes indicates primers annealing to the vector of the cDNA library used as a template for PCR. The presence of a triangle above a segment indicates that it contained a deletion of 154 bp (open triangle) or 26 bp (black triangle), likely caused by alternative splicing.

The predicted MW of human methionine synthase reductase is 77,700. It shares 38% sequence identity (49% similarity) with human cytochrome P450 reductase (accession #A60557) and 43% identity (53% similarity) with the C. elegans putative methionine synthase reductase (accession #Z35595). FIG. 4 shows amino acid sequence comparisons among human methionine synthase reductase (HsMTRR), C. elegans putative methionine synthase reductase (CeMTRR) and human cytochrome P450 reductase (HsCPR). The amino acids residues are numbered on the right margin, and conserved residues are shown by stars under the sequence. Alignments of similar amino acids are dotted (A,G,S,T,; D,E,N,Q; V,L,I,M; K,R; and F,W,Y), and regions proposed to be involved in binding of FMN, FAD or NADPH are shown above the sequences.

The first in-frame methionine residue is a candidate for the initiation codon. It is perfectly aligned with the first methionine of the C. elegans sequence, and the presence of a G at positions −3 and −6 places the sequence in good context for initiation of translation (Kozak, J. Biol. Chem. 266:19867–19870, 1991). A polyadenylation signal is present at positions 3135–3140. The poly(A) tail is added after position 3165, although we observed some clones with polyadenylation after residue 3157.

RT-PCR involving various pairs of primers allowed us to detect alternatively processed methionine synthase reductase mRNA, including one form with a deletion of 154 bp (nucleotides 129–282) and another lacking a 26 bp segment (−52 to −27), accounting for less than 20% and 40% of the mRNA, respectively.

TABLE 1

Oligonucleotides used for cDNA cloning, mapping, and mutation detection.

| Primers | Sequence | | Location |
|---|---|---|---|
| Z116 | 5'-CTCCTGCTCGAACATCTTCCTAAA | (SEQ ID NO:3) | 1318–1341 |
| Z117 | 5'-AATAGATAATCCCTATCCTTATGCC | (SEQ ID NO:4) | 1766–1742 |
| AD150 | 5'-CCCTGGCTCCTAAGATATCCATC | (SEQ ID NO:5) | 1544–1566 |
| AD151 | 5'-CGAACAACAAATTCTTTCCACTTACC | (SEQ ID NO:6) | 1573–1598 |
| AB191 | 5'-CAAGGTTGGTGGAAGTCGCGTTG | (SEQ ID NO:7) | −79—57 |
| AA468 | 5'-ATGCCTTGAAGTGATGAGGAGGTTT | (SEQ ID NO:8) | −13—12 |
| AB586 | 5'-TTCCTACAACATAGAGAGAAACTC | (SEQ ID NO:9) | 1663–1686 |
| AB588 | 5'-TTGCACAAGGGCATCATGTACATC | (SEQ ID NO:10) | 1998–1975 |
| Z593 | 5'-AAACCTCCTCATCACTTCAAGGCAT | (SEQ ID NO:11) | 12—13 |
| Z594 | 5'-CTTGCACACGAATATGGTCTGGG | (SEQ ID NO:12) | 1370–1348 |
| Z596 | 5'-TGGCATCACCTGCATCCTTGAGG | (SEQ ID NO:13) | 506–528 |
| Z597 | 5'-GATGTACCTGTAAATATTCTGGGGG | (SEQ ID NO:14) | 760–736 |
| 1103A | 5'-AATCCACGGCTCAACCACAAGTTC | (SEQ ID NO:15) | 429–406 |
| 1761 | 5'-CTCGAAATTAACCCTCACTAAAGGG | (SEQ ID NO:16) | in Bluescript |
| 1803E | 5'-AACCCATACCGCAGGTGAGCAAA | (SEQ ID NO:17) | 278–256 |
| 1812B | 5'-TTTAGTACTTTCAGTCAAAAAAGCTTAAT | (SEQ ID NO:18) | 2148–2120 |
| 1902C | 5'-ATAAACGACTTCAAGAGCTTGGAGC | (SEQ ID NO:19) | 335–359 |
| 2101C | 5'-AGGTTTGGCACTAGTAAAGCTGACT | (SEQ ID NO:20) | 2173–2149 |
| MSG108S | 5'-GCAAAGGCCATCGCAGAAGACAT | (SEQ ID NO:49) | 43–65 |
| AD292 | 5'-GTGAAGATCTGCAGAAAATCCATGTA | (SEQ ID NO:50) | 83–108 |

The sequence of the PCR products confirmed that our cDNA contained the putative FMN, FAD and NADPH binding sites. The 5' end of the sequence was obtained by PCR using a cDNA library as template, with antisense primers specific for the cDNA and a sense primer that anneals to the vector used to construct the library. The sequences generated by PCR were taken as error-free by comparison of the sequence of at least two, and usually three, independent PCR reactions.

The coding sequence of human methionine synthase reductase contains 2094 bp (SEQ ID NO: 1 and SEQ ID NO: 41) encoding a polypeptide of 698 amino acids (SEQ ID NO: 2 and SEQ ID NO: 42) in length. FIG. 3 shows the cDNA sequence (SEQ ID NO: 24) and deduced amino acid sequence of human methionine synthase reductase. The nucleotide residues are numbered on the left margin, the amino acids residues are numbered on the right margin, and the stop codon is indicated by three stars. The sequence has been deposited in the GenBank database, accession #AF025794.

EXAMPLE III

Expression of Human Methionine Reductase mRNA

A PCR product generated with primers 1902C (SEQ ID NO: 19) and 1812B (SEQ ID NO: 18) was subcloned and used to probe a Northern blot prepared from several human tissues.

Figure 5A:
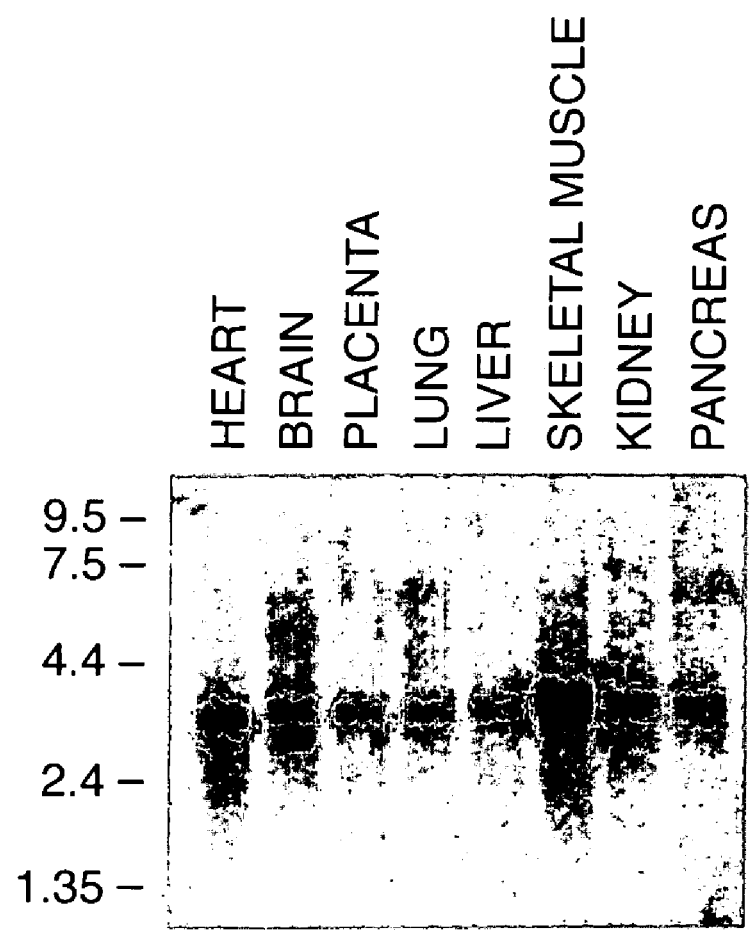
FIGS. 5A and 5B are representations of Northern blots showing an analysis of methionine synthase reductase expression in human tissues.
Figure 5B:

FIGS. 5A and 5B show a Northern blot analysis of methionine synthase reductase expression in human tissues, with the positions of the molecular size (kb) markers indicated at the left. The 1.8 kb probe hybridized to one predominant RNA species of 3.6 kb. Methionine synthase reductase appears to be expressed to some degree in all tissues tested and is particularly abundant in skeletal muscle. In addition to the 3.6 kb band, a 3.1 kb band and a faint 6 kb band were detected in brain mRNA.

EXAMPLE IV

Chromosomal Mapping of the Human Methionine Synthase Reductase Gene

Figure 6:
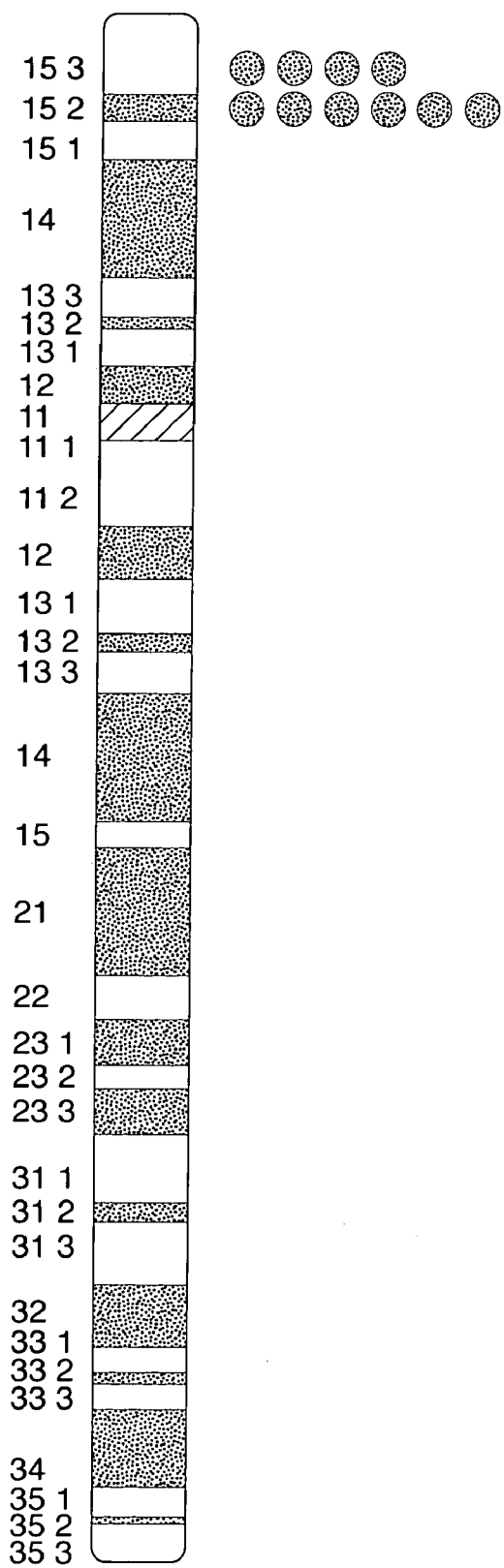
FIG. 6 is a diagram summarizing the FISH mapping of the methionine synthase reductase gene to human chromosome 5p15.2p15.3.

The methionine synthase reductase gene was localized to human chromosome 5, since the gene-specific primer pair amplified a PCR product of the expected size only from the GM10114 hybrid, which contains chromosome 5 as its only human material. Moreover, the DNA sequence we determined for the methionine synthase reductase gene matched markers AA002A03 and STSG444, which were also mapped by the NCBI consortium to chromosome 5 between markers D5S406–D5S478 and D5S406–D5S635, respectively (Hudson, T. J. et al., Science 270:1945–1954, 1995). To determine the cytogenetic position of the gene on chromosome 5, we mapped a genomic PAC clone encompassing the gene using fluorescence in situ hybridization (FISH). FIG. 6 shows a summary of the FISH mapping of the methionine synthase reductase gene to human chromosome 5p15.2-p15.3. Each dot represents a signal detected on human chromosome 5. The hybridization efficiency was 100%, and, among 100 mitotic figures examined, each result indicated that the gene was located on chromosome 5p15.2-p 15.3. We propose MTRR as the gene name for methionine synthase reductase, since the methionine synthase gene has been named MTR.

EXAMPLE V

Mutations of the Methionine Synthase Reductase Gene in Patients of the cblE Complementation Group To confirm the identity of the candidate cDNA as methionine synthase reductase, patient cell lines from the cblE complementation group were analyzed by RT-PCR-dependent heteroduplex analysis using nine RT-PCR reactions that yielded overlapping products, in order to cover the length of the candidate cDNA sequence. Patient samples were mixed with RT-PCR product from normal cells to ensure the availability of wild-type DNA, in order to enable the detection of heteroduplexes in samples in which the mutation might be homozygous. For samples yielding heteroduplexes, the analysis was repeated without prior mixing with wild-type DNA, in order to determine whether the relevant changes were heterozygous. Three cell lines showed typical heteroduplex patterns, one of them observed in overlapping RT-PCR fragments (FIGS. 7A and 7B).

FIGS. 7A and 7B show a mutation analysis of the methionine synthase reductase gene in cblE patient cell lines. FIG. 7A shows the PCR products obtained with primers Z116 (SEQ ID NO: 3) and Z117 (SEQ ID NO: 4) from RT reactions with control sample (WT) and two cblE cell lines, WG1146 and WG1836. The bands above the 449 bp amplification product result from heteroduplexes formed between DNA strands bearing different allelic sequences. The pattern observed for cell line WG1146 was also seen with cell line WG788 (the sibling of WG1146). FIG. 7B shows RT-PCR products amplified with primers AB586 (SEQ ID NO: 9) and AB588 (SEQ ID NO: 10) from a control sample and cell line WG1836. Heteroduplexes are observed above the 336 bp band for cell line WG1836.

The heteroduplex-containing samples were subcloned and sequenced and two mutations were identified. A heterozygous mutation present in fibroblast line WG788 is a 4 bp deletion, 1675del4, resulting in a frameshift that creates a nearby stop codon. The same mutation was observed in cell line WG1146 from the brother of patient WG788. Direct sequencing of the PCR product using primer AD150 showed overlapping sequences starting at position 1675, consistent with the heterozygous presence of the 4 bp deletion.

The second heterozygous mutation, detected in cell line WG1836, is an in-frame deletion of 3 bp, 1726delTTG. It results in the loss of a highly conserved leucine at position 576 of the amino acid sequence.

FIG. 7C shows a sequence comparison among proteins of the FNR family in a part of the NADPH binding region in the vicinity of the leucine residue that is deleted in a cblE patient (denoted by a triangle; MTRR is methionine synthase reductase; CPR is cytochrome P450 reductase; NOS is nitric oxide synthase; SR is sulfite reductase; and FNR is NADPH-ferredoxin(flavodoxin) reductase).

Primer AD151 (SEQ ID NO: 6) was used for direct sequencing of the WG1836 PCR product. In this case, the deletion of nucleotides 1726–1728 was clearly visible. There was only a very faint background contributed by the normal sequence, suggesting that a second, unidentified mutation in this cell line was associated with a very low level of steady-state mRNA.

EXAMPLE VI

Human Methionine Synthase Reductase Polymorphisms

We have identified two polymorphisms in methionine synthase reductase cDNAs. The first is a G/A polymorphism at nucleotide position 66, using the "A" of the initiator methionine as nucleotide position number 1 (see FIG. 3), which results in either an isoleucine or a methionine, respectively, at amino acid 22. The second polymorphism is a G/A polymorphism at nucleotide position 110, which results in either a tyrosine or a cysteine, respectively, at amino acid position 37. It is likely that additional methionine synthase reductase polymorphisms will be found, some of which will be associated with increased or decreased risks of disease.

EXAMPLE VII

Figure 8A:
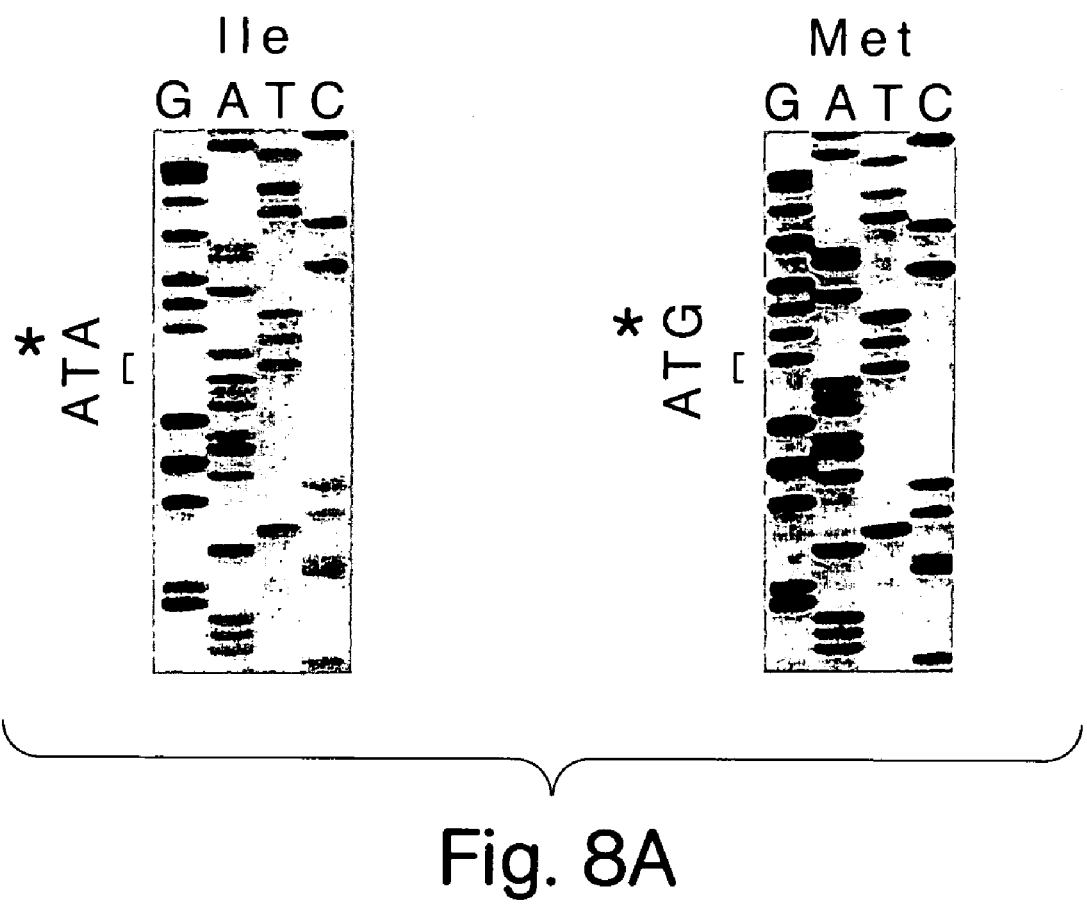
FIG. 8A is a representation of two autoradiograms showing the A to G polymorphism at MTRR coding position 66.
Figure 8B:
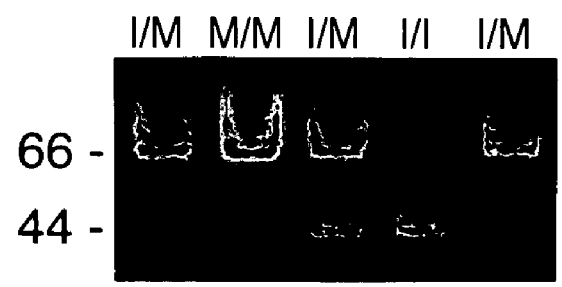
FIG. 8B is a representation of a gel showing a restriction digest assay for distinguishing between the adenine 66 and guanine 66 alleles.

A Common Polymorphism in Methionine Synthase Reductase as a Risk Factor for Spina Bifida During screening for methionine synthase reductase (MTRR) mutations in patients with homocystinuria, we identified an A/G polymorphism at bp 66, which yields an isoleucine (22I) or a methionine (22M), respectively, at amino acid position 22 (FIG. 8A). Since the presence of the methionine polymorphism at this position did not create or obliterate a naturally-occurring restriction site, a PCR-dependent diagnostic test was established that makes use of a modified sense primer to create a NdeI site in the isoleucine allele during the amplification reaction. The PCR product of 66 bp remains uncut in the presence of the methionine allele, but is digested into fragments of 44 and 22 bp in the presence of the isoleucine allele (FIG. 5B). The cDNA sequence reported in Leclerc, et al., *Proc. Natl. Acad. Sci. USA*, 95:3059–3064, 1998, contained the methionine codon.

The NdeI assay was used to assess allele frequencies in controls. The 22I/22M polymorphism was extremely common in our control adult population (mothers of control children, n=89). Forty-nine percent were heterozygous while 26% were homozygous for the methionine allele (Table 2). The allele frequency was 0.51 for the methionine variant. Similar frequencies were observed for control children. The controls in this study were white Caucasian individuals with French, British, and mixed European ancestry. Since the allele frequency is virtually identical for the two variants, the designation of a "wild type" allele could not be ascertained based on frequency. However, this gene has significant homology with related FMN-binding proteins from other organisms, including the putative methionine synthase reductase from *C. elegans*, as well as sulfite reductases, nitric oxide synthases, cytochrome P450 reductases, and flavodoxins. The equivalent codon in these genes is isoleucine, leucine, or valine in 123 out of 130 entries in GenBank. None of the entries contained a methionine codon. Consequently, the ancestral human MTRR sequence is likely to contain the isoleucine codon (22I), with a subsequent mutation to methionine (22M).

In this study, 34% (19/56) of case (spina bifida) children and 36% (21/58) of case mothers were homozygous for the 22M polymorphism in MTRR, compared to 30% (29/97) of control children and 26% (23/89) of control mothers (Table 2). An increased risk for being a case (odds ratio (OR) 1.7, 95% confidence interval (CI) 0.67–4.6)) or a case mother (O.R. 2.0, 95% CI 0.77–5.2) was observed when the homozygous mutant (M/M) genotype was present, but this increase was not statistically significant. Mother-child genotype pairs were also assessed for neural tube defect (NTD) risk to determine if the combination of mutant maternal and mutant child genotypes conferred a greater risk than either genotype alone; an increased risk was not observed. Homocysteine levels were not increased in individuals who were homozygous mutant for MTRR (Table 3).

Synergistic Interaction Between MTRR Genotype and Cobalamin Level Influences the Risk of NTD Case children had serum cobalamin levels (pmol/L) of 487±250 (n=55), whereas control children had serum cobalamin levels of 535±339 (n=95); case mothers had serum cobalamin levels of 298±186 (n=59), whereas control mothers had serum cobalamin levels of 350±135 (n=88; p=0.05). We therefore asked whether the mutant MTRR genotype may have a greater impact on NTD risk when cobalamin levels are low. Table 4 shows the results of multiple logistic regression analysis, adjusted for age, to test this hypothesis. Having a cobalamin level in the lowest quartile of the control distribution was associated with a nonsignificant two-fold increase in risk for the case mothers (O.R.=2.1; 95% CI=0.86–5.2). There was no increase in risk for low cobalamin in the children. However, the combination of homozygous mutant genotype and low cobalamin was associated with a significant 5-fold increase in risk for the mothers, compared to those without the M/M genotype and with cobalamin levels in the other 3 quartiles (O.R.=4.8, 95% CI=1.5–15.8). The risk for the children with this combination was also increased but statistical significance was not observed (O.R.=2.5, 95% CI=0.63–9.7). There was no increased risk for the mutant genotype combined with low folate. Because the MTRR genotype alone was associated with less risk, we speculate that genotype and cobalamin levels work in unison to produce increased risk for spina bifida in the case mothers and case children.

Synergistic Interaction Between MTRR and MTHFR Genotypes Influences the Risk of NTD The 677C→T polymorphism (SEQ ID NO: 51) in the methylenetetrahydrofolate reductase (MTHFR) gene converts an alanine to a valine residue in the enzyme (Frosst et al., *Nat. Genet.* 10:111–113, 1995). MTHFR catalyzes the synthesis of 5-methyltetrahydrofolate, the primary circulatory form of folate and the methyl donor in the remethylation of homocysteine to methionine by methionine synthase. Several studies have demonstrated an increased frequency of the homozygous mutant (V/V) MTHFR genotype in children with NTDs and in their mothers (van der Put et al., *Lancet* 346:1070–1071, 1995; Whitehead et al., *Quart. J. Med.* 88:763–766, 1995; Ou et al., *Am. J. Med. Genet.* 63:610–614, 1996).

Table 5 shows the interaction between the MTRR genotype and the MTHFR genotype in NTD risk, as determined by multiple logistic regression analysis, adjusted for age. Using a genotype of either homozygous wild type or heterozygous for MTRR and homozygous wild type for MTHFR as the reference, a risk nearly five times as great is conferred to case children (O.R.=4.9, 95% CI=1.1–21.8) and to case mothers (O.R.=5.0, 95% CI 0.8–31.3) when they are homozygous for both mutations. The risk for the combination of mutant genotypes is clearly higher than either mutant genotype alone, in both the cases and in their mothers.

TABLE 2

Frequency of MTRR genotypes in children with spina bifida (cases) and in case mothers.

|  | I/I | I/M | M/M |
|---|---|---|---|
| Cases | 9/56 (16%) | 28/56 (50%) | 19/56 (34%) |
| Controls | 24/97 (25%) | 44/97 (45%) | 29/97 (30%) |
| Case mothers | 10/58 (17%) | 27/58 (47%) | 21/58 (36%) |
| Control mothers | 22/89 (25%) | 44/89 (49%) | 23/89 (26%) |

O.R. for children, M/M vs. I/I = 1.7 (95% C.I. 0.67–4.6)
O.R. for mothers, M/M vs. I/I = 2.0 (95% C.I. 0.77–5.2)

TABLE 3

Homocysteine levels stratified by MTRR genotype. (tHcy (μmol/L))

|  | I/I n | I/M n | M/M n |
|---|---|---|---|
| Children | 7.7 ± 2.833 | 8.2 ± 3.372 | 8.2 ± 3.148 |
| Mothers | 9.7 ± 2.832 | 10.3 ± 4.771 | 9.4 ± 3.143 |

TABLE 4

Logistic regression analysis for NTD risk in children and mothers. Odds ratio > (95% C.I.)

| MTRR Genotype | Cobalamin level | Children | Mothers |
|---|---|---|---|
| I/I or I/M | normal | 1.0 (ref.) | 1.0 (ref.) |
| I/I or I/M | low | 0.92 (0.37–2.3) | 2.1 (0.86–5.2) |
| M/M | normal | 1.1 (0.46–2.5) | 1.5 (0.56–4.1) |
| M/M | low | 2.5 (0.63–9.7) | 4.8 (1.5–15.8) |

Odds ratios are adjusted by age of children and mothers respectively. Low cobalamin refers to the lowest quartile of the control distribution; normal refers to the other 3 quartiles.

TABLE 5

Logistic regression analysis for NTD risk in children and mothers. Odds ratio > (95% C.I.)

| MTRR Genotype | MTHFR Genotype | Children | Mothers |
|---|---|---|---|
| I/I or I/M | A/A | 1.0 (ref.) | 1.0 (ref.) |
| I/I or I/M | V/V | 0.82 (0.18–3.7) | 2.4 (0.69–8.3) |
| M/M | A/A | 1.2 (0.34–4.5) | 1.9 (0.61–5.7) |
| M/M | V/V | 4.9 (1.1–21.8) | 5.0 (0.80–31.3) |

Odds ratios are adjusted by age of children and mothers respectively.

EXAMPLE VIII

Human Methionine Synthase Reductase Mutations and Polymorphisms in Disease

Alterations in metabolism of folates, homocysteine, methionine, vitamin B12, and S-adenosylmethionine are associated with diseases such as megaloblastic anemia and conditions such as hyperhomocysteinemia. In turn, hyperhomocysteinemia may be associated with a higher than normal risk for cardiovascular disease and neural tube defects. In addition, decreased folate levels may be predictive of a lower than normal risk for cancer.

DNA samples from patients having a disease or developmental defect, such as those mentioned above, are analyzed for mutations within the methionine synthase reductase coding region and/or transcriptional control regions, and serum folate, red blood cell folate, plasma homocysteine, and serum cobalamin levels are measured. Patient samples are compared to control samples.

The cloning of the methionine synthase reductase gene makes possible the determination of whether discrete mutations and polymorphisms in methionine synthase reductase nucleic acid confer an increased risk for, or in contrast, protection against, diseases and conditions such as cardiovascular disease, cancer, and neural tube defects, (those of skill in the art will understand that polymorphisms and mutations may either increase or decrease the relative risk of any given disease or developmental defect). This collection of data in turn makes possible the development of diagnostic assays that predict whether a subject has a higher than normal risk of developing a disease or of having offspring with developmental defects. An understanding of disease-enhancing or -protective mutations allows the development of therapeutics that appropriately modulate methionine synthase reductase activity.

---

What is claimed is:

1. A substantially pure nucleic acid molecule having at least 95% sequence identity to SEQ ID NO: 1 and encoding a mammalian methionine synthase reductase polypeptide, wherein said polypeptide is capable of catalyzing the reductive methylation of methionine synthase-cob(II)alamin to generate methionine synthase-cob(III)alamin -CH3.

2. The nucleic acid of claim 1, wherein said nucleic acid molecule has the sequence of SEQ ID NO: 1.

3. The nucleic acid molecule of claim 1, wherein said nucleic acid molecule encodes a human methionine synthase reductase polypeptide.

4. The nucleic acid molecule of claim 1, wherein said nucleic acid molecule encodes a mammalian methionine synthase reductase polypeptide having at least 20% of the methionine synthase reductase activity of the methionine synthase reductase polypeptide of SEQ ID NO: 2.

5. The nucleic acid molecule of claim 4, wherein said nucleic acid molecule encodes a mammalian methionine synthase reductase polypeptide having at least 55% of the methionine synthase reductase activity of the methionine synthase reductase polypeptide of SEQ ID NO: 2.

6. The nucleic acid molecule of claim 1, wherein said nucleic acid molecule encodes a mammalian methionine synthase reductase polypeptide that comprises a consensus binding site for one or more cofactors selected from the group consisting of FAD, FMN, and NADPH, wherein said binding site comprises any one of SEQ ID NOs: 25 or 52–61.

7. The nucleic acid molecule of claim 1, wherein the polynucleotide sequence of said nucleic acid molecule comprises a mutation or polymorphism present in a naturally-occurring mammalian methionine synthase reductase gene.

8. A substantially pure nucleic acid molecule having at least 95% sequence identity to SEQ ID NO: 41, SEQ ID NO: 43, SEQ ID NO: 45, or SEQ ID NO: 47 and encoding a mammalian methionine synthase reductase polypeptide that has a reduced ability to catalyze the reductive methylation of methionine synthase-cob(II)alamin to generate methionine synthase-cob(III)alamin-CH3 relative to the methionine synthase reductase activity of a mammalian methionine synthase reductase polypeptide encoded by SEQ ID NO: 1.

9. The nucleic acid of claim 8, wherein said nucleic acid molecule has the sequence of SEQ ID NO: 41, SEQ ID NO: 43, SEQ ID NO: 45, or SEQ ID NO: 47.

10. The nucleic acid molecule of claim 8, wherein said nucleic acid molecule encodes a human methionine synthase reductase polypeptide.

11. The nucleic acid molecule of claim 8, wherein said nucleic acid molecule encodes a mammalian methionine synthase reductase polypeptide that comprises a consensus binding site for one or more cofactors selected from the group consisting of FAD, FMN, and NADPH, wherein said binding site comprises any one of SEQ ID NOs: 25 or 52–61.

12. The nucleic acid molecule of claim 8, wherein the polynucleotide sequence of said nucleic acid molecule comprises a mutation or polymorphism present in a naturally-occurring mammalian methionine synthase reductase gene.

13. A substantially pure antisense nucleic acid molecule consisting of a polynucleotide sequence that is completely complementary to at least 18 contiguous nucleotides of a mammalian methionine synthase reductase gene consisting of the polynucleotide sequence of SEQ ID NO: 1, SEQ ID NO: 41, SEQ ID NO: 43, SEQ ID NO: 45, or SEQ ID NO: 47.

14. The antisense nucleic acid molecule of claim 13, wherein said antisense nucleic acid molecule comprises a polynucleotide sequence the complete complement of which encodes a polypeptide consisting of the sequence set forth in any one of SEQ ID NOs: 52–61.

15. The antisense nucleic acid molecule of claim 13, wherein said antisense nucleic acid molecule comprises a polynucleotide sequence the complete complement of which comprises a mutation or polymorphism present in a naturally-occurring mammalian methionine synthase reductase gene.

* * * * *

UNITED STATES PATENT AND TRADEMARK OFFICE
CERTIFICATE OF CORRECTION

PATENT NO. : 7,045,612 B2
APPLICATION NO. : 09/371347
DATED : May 16, 2006
INVENTOR(S) : Gravel et al.

It is certified that error appears in the above-identified patent and that said Letters Patent is hereby corrected as shown below:

Column 5, Line 22ff., replace "length (RFLP) polymorphism" with
-- length polymorphism (RFLP) --.

Column 7, Line 63, replace "(MTTR)" with -- (MTRR) --.

Column 8, Line 6, replace "dieseases" with --diseases--.

Column 10, Line 64, replace "*Caenorrhabditis*" with
--*Caenorhabditis*--.

Column 12, Line 6, replace "cobal (II) amin" with
--cob (II) alamin--.

Column 17, Line 59, replace "immunosorbant" with
--immunosorbent--.

Column 22,
    Line 23, replace "cobolamin" with --cobalamin--;
    Line 26, replace "(tHey)" with -- (tHcy) --; and
    Line 30, replace "cetrifuged" with --centrifuged--.

Column 85, Line 67, replace "synthase-cob (II) alamin -CH3" with
--synthase-cob (II) alamin-CH3--.

Signed and Sealed this

Twelfth Day of December, 2006

JON W. DUDAS
*Director of the United States Patent and Trademark Office*

SEQUENCE LISTING

```
<160> NUMBER OF SEQ ID NOS: 61

<210> SEQ ID NO 1
<211> LENGTH: 2097
<212> TYPE: DNA
<213> ORGANISM: Homo sapiens

<400> SEQUENCE: 1
atgaggaggt ttctgttact atatgctaca cagcagggac aggcaaaggc catcgcagaa      60
gaaatgtgtg agcaagctgt ggtacatgga ttttctgcag atcttcactg tattagtgaa     120
tccgataagt atgacctaaa aaccgaaaca gctcctcttg ttgttgtggt ttctaccacg     180
ggcaccggag acccacccga cacagcccgc aagtttgtta aggaaataca gaaccaaaca     240
ctgccggttg atttctttgc tcacctgcgg tatgggttac tgggtctcgg tgattcagaa     300
tacacctact tttgcaatgg ggggaagata attgataaac gacttcaaga gcttggagcc     360
cggcatttct atgacactgg acatgcagat gactgtgtag gtttagaact tgtggttgag     420
ccgtggattg ctggactctg gccagccctc agaaagcatt ttaggtcaag cagaggacaa     480
gaggagataa gtggcgcact cccggtggca tcacctgcat ccttgaggac agaccttgtg     540
aagtcagagc tgctacacat tgaatctcaa gtcgagcttc tgagattcga tgattcagga     600
agaaaggatt ctgaggtttt gaagcaaaat gcagtgaaca gcaaccaatc caatgttgta     660
attgaagact ttgagtcctc acttacccgt tcggtacccc cactctcaca agcctctctg     720
aatattcctg gtttacccc agaatattta caggtacatc tgcaggagtc tcttggccag     780
gaggaaagcc aagtatctgt gacttcagca gatccagttt ttcaagtgcc aatttcaaag     840
gcagttcaac ttactacgaa tgatgccata aaaccactc tgctggtaga attggacatt     900
tcaaatacag acttttccta tcagcctgga gatgccttca gcgtgatctg ccctaacagt     960
gattctgagg tacaaagcct actccaaaga ctgcagcttg aagataaaag agagcactgc    1020
```

-continued

```
gtccttttga aaataaaggc agacacaaag aagaaggag ctaccttacc ccagcatata      1080
cctgcgggat gttctctcca gttcattttt acctggtgtc ttgaaatccg agcaattcct      1140
aaaaaggcat ttttgcgagc ccttgtggac tataccagtg acagtgctga aaagcgcagg      1200
ctacaggagc tgtgcagtaa acaaggggca gccgattata gccgctttgt acgagatgcc      1260
tgtgcctgct tgttggatct cctcctcgct ttcccttctt gccagccacc actcagtctc      1320
ctgctcgaac atcttcctaa acttcaaccc agaccatatt cgtgtgcaag ctcaagttta      1380
tttcacccag gaaagctcca tttgtcttc aacattgtgg aatttctgtc tactgccaca      1440
acagaggttc tgcggaaggg agtatgtaca ggctggctgg ccttgttggt tgcttcagtt      1500
cttcagccaa acatacatgc atcccatgaa gacagcggga aagccctggc tcctaagata      1560
tccatctctc ctcgaacaac aaattctttc cacttaccag atgacccctc aatccccatc      1620
ataatggtgg gtccaggaac cggcatagcc ccgtttattg ggttcctaca acatagagag      1680
aaactccaag aacaacaccc agatggaaat tttggagcaa tgtggttgtt ttttggctgc      1740
aggcataagg atagggatta tctattcaga aaagagctca gacatttcct taagcatggg      1800
atcttaactc atctaaaggt ttccttctca agagatgctc ctgttgggga ggaggaagcc      1860
ccagcaaagt atgtacaaga caacatccag cttcatggcc agcaggtggc gagaatcctc      1920
ctccaggaga acggccatat ttatgtgtgt ggagatgcaa agaatatggc caaggatgta      1980
catgatgccc ttgtgcaaat aataagcaaa gaggttggag ttgaaaaact agaagcaatg      2040 aaaccctgg ccactttaaa agaagaaaaa cgctaccttc aggatatttg gtcataa        2097
```

<210> SEQ ID NO 2
<211> LENGTH: 698
<212> TYPE: PRT
<213> ORGANISM: Homo sapiens

<400> SEQUENCE: 2

```
Met Arg Arg Phe Leu Leu Leu Tyr Ala Thr Gln Gln Gly Gln Ala Lys
 1               5                   10                  15

Ala Ile Ala Glu Glu Met Cys Glu Gln Ala Val Val His Gly Phe Ser
             20                  25                  30

Ala Asp Leu His Cys Ile Ser Glu Ser Asp Lys Tyr Asp Leu Lys Thr
         35                  40                  45

Glu Thr Ala Pro Leu Val Val Val Ser Thr Thr Gly Thr Gly Asp
     50                  55                  60

Pro Pro Asp Thr Ala Arg Lys Phe Val Lys Glu Ile Gln Asn Gln Thr
 65                  70                  75                  80

Leu Pro Val Asp Phe Phe Ala His Leu Arg Tyr Gly Leu Gly Leu
                 85                  90                  95

Gly Asp Ser Glu Tyr Thr Tyr Phe Cys Asn Gly Gly Lys Ile Ile Asp
            100                 105                 110

Lys Arg Leu Gln Glu Leu Gly Ala Arg His Phe Tyr Asp Thr Gly His
        115                 120                 125

Ala Asp Asp Cys Val Gly Leu Glu Leu Val Val Glu Pro Trp Ile Ala
    130                 135                 140

Gly Leu Trp Pro Ala Leu Arg Lys His Phe Arg Ser Ser Arg Gly Gln
145                 150                 155                 160

Glu Glu Ile Ser Gly Ala Leu Pro Val Ala Ser Pro Ala Ser Leu Arg
                165                 170                 175

Thr Asp Leu Val Lys Ser Glu Leu Leu His Ile Glu Ser Gln Val Glu
```

-continued

```
                180                 185                 190
Leu Leu Arg Phe Asp Asp Ser Gly Arg Lys Asp Ser Glu Val Leu Lys
            195                 200                 205
Gln Asn Ala Val Asn Ser Asn Gln Ser Asn Val Val Ile Glu Asp Phe
        210                 215                 220
Glu Ser Ser Leu Thr Arg Ser Val Pro Leu Ser Gln Ala Ser Leu
225                 230                 235                 240
Asn Ile Pro Gly Leu Pro Pro Glu Tyr Leu Gln Val His Leu Gln Glu
                245                 250                 255
Ser Leu Gly Gln Glu Glu Ser Gln Val Ser Val Thr Ser Ala Asp Pro
            260                 265                 270
Val Phe Gln Val Pro Ile Ser Lys Ala Val Gln Leu Thr Thr Asn Asp
        275                 280                 285
Ala Ile Lys Thr Thr Leu Leu Val Glu Leu Asp Ile Ser Asn Thr Asp
        290                 295                 300
Phe Ser Tyr Gln Pro Gly Asp Ala Phe Ser Val Ile Cys Pro Asn Ser
305                 310                 315                 320
Asp Ser Glu Val Gln Ser Leu Leu Gln Arg Leu Gln Leu Glu Asp Lys
                325                 330                 335
Arg Glu His Cys Val Leu Leu Lys Ile Lys Ala Asp Thr Lys Lys Lys
                340                 345                 350
Gly Ala Thr Leu Pro Gln His Ile Pro Ala Gly Cys Ser Leu Gln Phe
            355                 360                 365
Ile Phe Thr Trp Cys Leu Glu Ile Arg Ala Ile Pro Lys Lys Ala Phe
        370                 375                 380
Leu Arg Ala Leu Val Asp Tyr Thr Ser Asp Ser Ala Glu Lys Arg Arg
385                 390                 395                 400
Leu Gln Glu Leu Cys Ser Lys Gln Gly Ala Ala Asp Tyr Ser Arg Phe
                405                 410                 415
Val Arg Asp Ala Cys Ala Cys Leu Leu Asp Leu Leu Leu Ala Phe Pro
                420                 425                 430
Ser Cys Gln Pro Pro Leu Ser Leu Leu Leu Glu His Leu Pro Lys Leu
            435                 440                 445
Gln Pro Arg Pro Tyr Ser Cys Ala Ser Ser Ser Leu Phe His Pro Gly
        450                 455                 460
Lys Leu His Phe Val Phe Asn Ile Val Glu Phe Leu Ser Thr Ala Thr
465                 470                 475                 480
Thr Glu Val Leu Arg Lys Gly Val Cys Thr Gly Trp Leu Ala Leu Leu
                485                 490                 495
Val Ala Ser Val Leu Gln Pro Asn Ile His Ala Ser His Glu Asp Ser
            500                 505                 510
Gly Lys Ala Leu Ala Pro Lys Ile Ser Ile Ser Pro Arg Thr Thr Asn
        515                 520                 525
Ser Phe His Leu Pro Asp Asp Pro Ser Ile Pro Ile Ile Met Val Gly
        530                 535                 540
Pro Gly Thr Gly Ile Ala Pro Phe Ile Gly Phe Leu Gln His Arg Glu
545                 550                 555                 560
Lys Leu Gln Glu Gln His Pro Asp Gly Asn Phe Gly Ala Met Trp Leu
                565                 570                 575
Phe Phe Gly Cys Arg His Lys Asp Arg Asp Tyr Leu Phe Arg Lys Glu
                580                 585                 590
Leu Arg His Phe Leu Lys His Gly Ile Leu Thr His Leu Lys Val Ser
            595                 600                 605
```

```
Phe Ser Arg Asp Ala Pro Val Gly Glu Glu Ala Pro Ala Lys Tyr
    610                 615                 620

Val Gln Asp Asn Ile Gln Leu His Gly Gln Gln Val Ala Arg Ile Leu
625                 630                 635                 640

Leu Gln Glu Asn Gly His Ile Tyr Val Cys Gly Asp Ala Lys Asn Met
                645                 650                 655

Ala Lys Asp Val His Asp Ala Leu Val Gln Ile Ile Ser Lys Glu Val
            660                 665                 670

Gly Val Glu Lys Leu Glu Ala Met Lys Thr Leu Ala Thr Leu Lys Glu
        675                 680                 685

Glu Lys Arg Tyr Leu Gln Asp Ile Trp Ser
690                 695
```

```
<210> SEQ ID NO 3
<211> LENGTH: 24
<212> TYPE: DNA
<213> ORGANISM: Homo sapiens

<400> SEQUENCE: 3
ctcctgctcg aacatcttcc taaa                                      24

<210> SEQ ID NO 4
<211> LENGTH: 25
<212> TYPE: DNA
<213> ORGANISM: Homo sapiens

<400> SEQUENCE: 4
aatagataat ccctatcctt atgcc                                     25

<210> SEQ ID NO 5
<211> LENGTH: 23
<212> TYPE: DNA
<213> ORGANISM: Homo sapiens

<400> SEQUENCE: 5
ccctggctcc taagatatcc atc                                       23

<210> SEQ ID NO 6
<211> LENGTH: 26
<212> TYPE: DNA
<213> ORGANISM: Homo sapiens

<400> SEQUENCE: 6
cgaacaacaa attctttcca cttacc                                    26

<210> SEQ ID NO 7
<211> LENGTH: 23
<212> TYPE: DNA
<213> ORGANISM: Homo sapiens

<400> SEQUENCE: 7
caaggttggt ggaagtcgcg ttg                                       23

<210> SEQ ID NO 8
<211> LENGTH: 25
<212> TYPE: DNA
<213> ORGANISM: Homo sapiens

<400> SEQUENCE: 8
atgccttgaa gtgatgagga ggttt                                     25
```

<210> SEQ ID NO 9
<211> LENGTH: 24
<212> TYPE: DNA
<213> ORGANISM: Homo sapiens

<400> SEQUENCE: 9
ttcctacaac atagagagaa actc  24

<210> SEQ ID NO 10
<211> LENGTH: 24
<212> TYPE: DNA
<213> ORGANISM: Homo sapiens

<400> SEQUENCE: 10
ttgcacaagg gcatcatgta catc  24

<210> SEQ ID NO 11
<211> LENGTH: 25
<212> TYPE: DNA
<213> ORGANISM: Homo sapiens

<400> SEQUENCE: 11
aaacctcctc atcacttcaa ggcat  25

<210> SEQ ID NO 12
<211> LENGTH: 23
<212> TYPE: DNA
<213> ORGANISM: Homo sapiens

<400> SEQUENCE: 12
cttgcacacg aatatggtct ggg  23

<210> SEQ ID NO 13
<211> LENGTH: 23
<212> TYPE: DNA
<213> ORGANISM: Homo sapiens

<400> SEQUENCE: 13
tggcatcacc tgcatccttg agg  23

<210> SEQ ID NO 14
<211> LENGTH: 25
<212> TYPE: DNA
<213> ORGANISM: Homo sapiens

<400> SEQUENCE: 14
gatgtacctg taaatattct ggggg  25

<210> SEQ ID NO 15
<211> LENGTH: 24
<212> TYPE: DNA
<213> ORGANISM: Homo sapiens

<400> SEQUENCE: 15
aatccacggc tcaaccacaa gttc  24

<210> SEQ ID NO 16
<211> LENGTH: 25
<212> TYPE: DNA
<213> ORGANISM: Homo sapiens

<400> SEQUENCE: 16
ctcgaaatta accctcacta aaggg  25

<210> SEQ ID NO 17
<211> LENGTH: 23
<212> TYPE: DNA
<213> ORGANISM: Homo sapiens

<400> SEQUENCE: 17
aacccatacc gcaggtgagc aaa                                                  23

<210> SEQ ID NO 18
<211> LENGTH: 29
<212> TYPE: DNA
<213> ORGANISM: Homo sapiens

<400> SEQUENCE: 18
tttagtactt tcagtcaaaa aagcttaat                                            29

<210> SEQ ID NO 19
<211> LENGTH: 25
<212> TYPE: DNA
<213> ORGANISM: Homo sapiens

<400> SEQUENCE: 19
ataaacgact tcaagagctt ggagc                                                25

<210> SEQ ID NO 20
<211> LENGTH: 25
<212> TYPE: DNA
<213> ORGANISM: Homo sapiens

<400> SEQUENCE: 20
aggtttggca ctagtaaagc tgact                                                25

<210> SEQ ID NO 21
<211> LENGTH: 698
<212> TYPE: PRT
<213> ORGANISM: Homo sapiens

<400> SEQUENCE: 21

Met Arg Arg Phe Leu Leu Tyr Ala Thr Gln Gln Gly Gln Ala Lys
 1               5                  10                  15

Ala Ile Ala Glu Glu Met Cys Glu Gln Ala Val Val His Gly Phe Ser
            20                  25                  30

Ala Asp Leu His Cys Ile Ser Glu Ser Asp Lys Tyr Asp Leu Lys Thr
        35                  40                  45

Glu Thr Ala Pro Leu Val Val Val Ser Thr Thr Gly Thr Gly Asp
    50                  55                  60

Pro Pro Asp Thr Ala Arg Lys Phe Val Lys Glu Ile Gln Asn Gln Thr
65                  70                  75                  80

Leu Pro Val Asp Phe Phe Ala His Leu Arg Tyr Gly Leu Leu Gly Leu
                85                  90                  95

Gly Asp Ser Glu Tyr Thr Tyr Phe Cys Asn Gly Gly Lys Ile Ile Asp
            100                 105                 110

Lys Arg Leu Gln Glu Leu Gly Ala Arg His Phe Tyr Asp Thr Gly His
        115                 120                 125

Ala Asp Asp Cys Val Gly Leu Glu Leu Val Val Glu Pro Trp Ile Ala
    130                 135                 140

Gly Leu Trp Pro Ala Leu Arg Lys His Phe Arg Ser Ser Arg Gly Gln
145                 150                 155                 160

-continued

| | | | | | | | | | | | |
|---|---|---|---|---|---|---|---|---|---|---|---|
|Glu|Glu|Ile|Ser|Gly|Ala|Leu|Pro|Val|Ala|Ser|Pro|Ala|Ser|Leu|Arg|
| | | | |165| | | |170| | | |175| | |

Glu Glu Ile Ser Gly Ala Leu Pro Val Ala Ser Pro Ala Ser Leu Arg
                165                 170                 175

Thr Asp Leu Val Lys Ser Glu Leu Leu His Ile Glu Ser Gln Val Glu
            180                 185                 190

Leu Leu Arg Phe Asp Asp Ser Gly Arg Lys Asp Ser Glu Val Leu Lys
        195                 200                 205

Gln Asn Ala Val Asn Ser Asn Gln Ser Asn Val Val Ile Glu Asp Phe
210                 215                 220

Glu Ser Ser Leu Thr Arg Ser Val Pro Leu Ser Gln Ala Ser Leu
225                 230                 235                 240

Asn Ile Pro Gly Leu Pro Pro Glu Tyr Leu Gln Val His Leu Gln Glu
                245                 250                 255

Ser Leu Gly Gln Glu Glu Ser Gln Val Ser Val Thr Ser Ala Asp Pro
            260                 265                 270

Val Phe Gln Val Pro Ile Ser Lys Ala Val Gln Leu Thr Thr Asn Asp
        275                 280                 285

Ala Ile Lys Thr Thr Leu Leu Val Glu Leu Asp Ile Ser Asn Thr Asp
290                 295                 300

Phe Ser Tyr Gln Pro Gly Asp Ala Phe Ser Val Ile Cys Pro Asn Ser
305                 310                 315                 320

Asp Ser Glu Val Gln Ser Leu Leu Gln Arg Leu Gln Leu Glu Asp Lys
            325                 330                 335

Arg Glu His Cys Val Leu Leu Lys Ile Lys Ala Asp Thr Lys Lys Lys
            340                 345                 350

Gly Ala Thr Leu Pro Gln His Ile Pro Ala Gly Cys Ser Leu Gln Phe
            355                 360                 365

Ile Phe Thr Trp Cys Leu Glu Ile Arg Ala Ile Pro Lys Lys Ala Phe
        370                 375                 380

Leu Arg Ala Leu Val Asp Tyr Thr Ser Asp Ser Ala Glu Lys Arg Arg
385                 390                 395                 400

Leu Gln Glu Leu Cys Ser Lys Gln Gly Ala Ala Asp Tyr Ser Arg Phe
                405                 410                 415

Val Arg Asp Ala Cys Ala Cys Leu Leu Asp Leu Leu Ala Phe Pro
            420                 425                 430

Ser Cys Gln Pro Pro Leu Ser Leu Leu Glu His Leu Pro Lys Leu
        435                 440                 445

Gln Pro Arg Pro Tyr Ser Cys Ala Ser Ser Ser Leu Phe His Pro Gly
    450                 455                 460

Lys Leu His Phe Val Phe Asn Ile Val Glu Phe Leu Ser Thr Ala Thr
465                 470                 475                 480

Thr Glu Val Leu Arg Lys Gly Val Cys Thr Gly Trp Leu Ala Leu Leu
                485                 490                 495

Val Ala Ser Val Leu Gln Pro Asn Ile His Ala Ser His Glu Asp Ser
            500                 505                 510

Gly Lys Ala Leu Ala Pro Lys Ile Ser Ile Ser Pro Arg Thr Thr Asn
    515                 520                 525

Ser Phe His Leu Pro Asp Asp Pro Ser Ile Pro Ile Ile Met Val Gly
    530                 535                 540

Pro Gly Thr Gly Ile Ala Pro Phe Ile Gly Phe Leu Gln His Arg Glu
545                 550                 555                 560

Lys Leu Gln Glu Gln His Pro Asp Gly Asn Phe Gly Ala Met Trp Leu
                565                 570                 575

Phe Phe Gly Cys Arg His Lys Asp Arg Asp Tyr Leu Phe Arg Lys Glu

-continued

```
                580                 585                 590
Leu Arg His Phe Leu Lys His Gly Ile Leu Thr His Leu Lys Val Ser
            595                 600                 605

Phe Ser Arg Asp Ala Pro Val Gly Glu Glu Ala Pro Ala Lys Tyr
        610                 615                 620

Val Gln Asp Asn Ile Gln Leu His Gly Gln Gln Val Ala Arg Ile Leu
625                 630                 635                 640

Leu Gln Glu Asn Gly His Ile Tyr Val Cys Gly Asp Ala Lys Asn Met
                645                 650                 655

Ala Lys Asp Val His Asp Ala Leu Val Gln Ile Ile Ser Lys Glu Val
            660                 665                 670

Gly Val Glu Lys Leu Glu Ala Met Lys Thr Leu Ala Thr Leu Lys Glu
            675                 680                 685

Glu Lys Arg Tyr Leu Gln Asp Ile Trp Ser
        690                 695

<210> SEQ ID NO 22
<211> LENGTH: 682
<212> TYPE: PRT
<213> ORGANISM: Caenorhabditis elegans

<400> SEQUENCE: 22

Met Thr Asp Phe Leu Ile Ala Phe Gly Ser Gln Thr Gly Gln Ala Glu
1               5                   10                  15

Thr Ile Ala Lys Ser Leu Lys Glu Lys Ala Glu Leu Ile Gly Leu Thr
            20                  25                  30

Pro Arg Leu His Ala Leu Asp Glu Asn Glu Lys Lys Phe Asn Leu Asn
        35                  40                  45

Glu Glu Lys Leu Cys Ala Ile Val Val Ser Ser Thr Gly Asp Gly Asp
    50                  55                  60

Ala Pro Asp Asn Cys Ala Arg Phe Val Arg Arg Ile Asn Arg Asn Ser
65                  70                  75                  80

Leu Glu Asn Glu Tyr Leu Lys Asn Leu Asp Tyr Val Leu Leu Gly Leu
                85                  90                  95

Gly Asp Ser Asn Tyr Ser Ser Tyr Gln Thr Ile Pro Arg Lys Ile Asp
            100                 105                 110

Lys Gln Leu Thr Ala Leu Gly Ala Asn Arg Leu Phe Asp Arg Ala Glu
        115                 120                 125

Ala Asp Asp Gln Val Gly Leu Glu Leu Glu Val Glu Pro Trp Ile Glu
130                 135                 140

Lys Phe Phe Ala Thr Leu Ala Ser Arg Phe Asp Ile Ser Ala Asp Lys
145                 150                 155                 160

Met Asn Ala Ile Thr Glu Ser Ser Asn Leu Lys Leu Asn Gln Val Lys
                165                 170                 175

Thr Glu Glu Glu Lys Lys Ala Leu Leu Gln Lys Arg Ile Glu Asp Glu
            180                 185                 190

Glu Ser Asp Asp Glu Gly Arg Gly Arg Val Ile Gly Ile Asp Met Leu
        195                 200                 205

Ile Pro Glu His Tyr Asp Tyr Pro Glu Ile Ser Leu Leu Lys Gly Ser
    210                 215                 220

Gln Thr Leu Ser Asn Asp Glu Asn Leu Arg Val Pro Ile Ala Pro Gln
225                 230                 235                 240

Pro Phe Ile Val Ser Ser Val Ser Asn Arg Lys Leu Pro Glu Asp Thr
                245                 250                 255
```

```
Lys Leu Glu Trp Gln Asn Leu Cys Lys Met Pro Gly Val Val Thr Lys
            260                 265                 270

Pro Phe Glu Val Leu Val Ser Ala Glu Phe Val Thr Asp Pro Phe
        275                 280                 285

Ser Lys Lys Ile Lys Thr Lys Arg Met Ile Thr Val Asp Phe Gly Asp
    290                 295                 300

His Ala Ala Glu Leu Gln Tyr Glu Pro Gly Asp Ala Ile Tyr Phe Cys
305                 310                 315                 320

Val Pro Asn Pro Ala Leu Glu Val Asn Phe Ile Leu Lys Arg Cys Gly
                325                 330                 335

Val Leu Asp Ile Ala Asp Gln Gln Cys Glu Leu Ser Ile Asn Pro Lys
            340                 345                 350

Thr Glu Lys Ile Asn Ala Gln Ile Pro Gly His Val His Lys Ile Thr
        355                 360                 365

Thr Leu Arg His Met Phe Thr Thr Cys Leu Asp Ile Arg Arg Ala Pro
    370                 375                 380

Gly Arg Pro Leu Ile Arg Val Leu Ala Glu Ser Thr Ser Asp Pro Asn
385                 390                 395                 400

Glu Lys Arg Arg Leu Leu Glu Leu Cys Ser Ala Gln Gly Met Lys Asp
                405                 410                 415

Phe Thr Asp Phe Val Arg Thr Pro Gly Leu Ser Leu Ala Asp Met Leu
            420                 425                 430

Phe Ala Phe Pro Asn Val Lys Pro Pro Val Asp Arg Leu Ile Glu Leu
        435                 440                 445

Leu Pro Arg Leu Ile Pro Arg Pro Tyr Ser Met Ser Ser Tyr Glu Asn
    450                 455                 460

Arg Lys Ala Arg Leu Ile Tyr Ser Glu Met Glu Phe Pro Ala Thr Asp
465                 470                 475                 480

Gly Arg Arg His Ser Arg Lys Gly Leu Ala Thr Asp Trp Leu Asn Ser
                485                 490                 495

Leu Arg Ile Gly Asp Lys Val Gln Val Leu Gly Lys Glu Pro Ala Arg
            500                 505                 510

Phe Arg Leu Pro Pro Leu Gly Met Thr Lys Asn Ser Ala Gly Lys Leu
        515                 520                 525

Pro Leu Leu Met Val Gly Pro Gly Thr Gly Val Ser Val Phe Leu Ser
    530                 535                 540

Phe Leu His Phe Leu Arg Lys Leu Lys Gln Asp Ser Pro Ser Asp Phe
545                 550                 555                 560

Val Asp Val Pro Arg Val Leu Phe Phe Gly Cys Arg Asp Ser Ser Val
                565                 570                 575

Asp Ala Ile Tyr Met Ser Glu Leu Glu Met Phe Val Ser Glu Gly Ile
            580                 585                 590

Leu Thr Asp Leu Ile Ile Cys Glu Ser Glu Gln Lys Gly Glu Arg Val
    595                 600                 605

Gln Asp Gly Leu Arg Lys Tyr Leu Asp Lys Val Leu Pro Phe Leu Thr
610                 615                 620

Ala Ser Thr Glu Ser Lys Ile Phe Ile Cys Gly Asp Ala Lys Gly Met
625                 630                 635                 640

Ser Lys Asp Val Trp Gln Cys Phe Ser Asp Ile Val Ala Ser Asp Gln
                645                 650                 655

Gly Ile Pro Asp Leu Glu Ala Lys Lys Lys Leu Met Asp Leu Lys Lys
            660                 665                 670

Ser Asp Gln Tyr Ile Glu Asp Val Trp Gly
```

-continued

```
            675                 680

<210> SEQ ID NO 23
<211> LENGTH: 677
<212> TYPE: PRT
<213> ORGANISM: Homo sapiens

<400> SEQUENCE: 23

Met Gly Asp Ser His Val Asp Thr Ser Ser Thr Val Ser Glu Ala Val
  1               5                  10                  15

Ala Glu Glu Val Ser Leu Phe Ser Met Thr Asp Met Ile Leu Phe Ser
                 20                  25                  30

Leu Ile Val Gly Leu Leu Thr Tyr Trp Phe Leu Phe Arg Lys Lys Lys
             35                  40                  45

Glu Glu Val Pro Glu Phe Thr Lys Ile Gln Thr Leu Thr Ser Ser Val
         50                  55                  60

Arg Glu Ser Ser Phe Val Glu Lys Met Lys Lys Thr Gly Arg Asn Ile
 65                  70                  75                  80

Ile Val Phe Tyr Gly Ser Gln Thr Gly Thr Ala Glu Glu Phe Ala Asn
                 85                  90                  95

Arg Leu Ser Lys Asp Ala His Arg Tyr Gly Met Arg Gly Met Ser Ala
                100                 105                 110

Asp Pro Glu Glu Tyr Asp Leu Ala Asp Leu Ser Ser Leu Pro Glu Ile
            115                 120                 125

Asp Asn Ala Leu Val Val Phe Cys Met Ala Thr Tyr Gly Glu Gly Asp
        130                 135                 140

Pro Thr Asp Asn Ala Gln Asp Phe Tyr Asp Trp Leu Gln Glu Thr Asp
145                 150                 155                 160

Val Asp Leu Ser Gly Val Lys Phe Ala Val Phe Gly Leu Gly Asn Lys
                165                 170                 175

Thr Tyr Glu His Phe Asn Ala Met Gly Lys Tyr Val Asp Lys Arg Leu
                180                 185                 190

Glu Gln Leu Gly Ala Gln Arg Ile Phe Glu Leu Gly Leu Gly Asp Asp
            195                 200                 205

Asp Gly Asn Leu Glu Glu Asp Phe Ile Thr Trp Arg Glu Gln Phe Trp
        210                 215                 220

Pro Ala Val Cys Glu His Phe Gly Val Glu Ala Thr Gly Glu Glu Ser
225                 230                 235                 240

Ser Ile Arg Gln Tyr Glu Leu Val Val His Thr Asp Ile Asp Ala Ala
                245                 250                 255

Lys Val Tyr Met Gly Glu Met Gly Arg Leu Lys Ser Tyr Glu Asn Gln
                260                 265                 270

Lys Pro Pro Phe Asp Ala Lys Asn Pro Phe Leu Ala Ala Val Thr Thr
            275                 280                 285

Asn Arg Lys Leu Asn Gln Gly Thr Glu Arg His Leu Met His Leu Glu
        290                 295                 300

Leu Asp Ile Ser Asp Ser Lys Ile Arg Tyr Glu Ser Gly Asp His Val
305                 310                 315                 320

Ala Val Tyr Pro Ala Asn Asp Ser Ala Leu Val Asn Gln Leu Gly Lys
                325                 330                 335

Ile Leu Gly Ala Asp Leu Asp Val Val Met Ser Leu Asn Asn Leu Asp
                340                 345                 350

Glu Glu Ser Asn Lys Lys His Pro Phe Pro Cys Pro Thr Ser Tyr Arg
            355                 360                 365
```

```
Thr Ala Leu Thr Tyr Tyr Leu Asp Ile Thr Asn Pro Pro Arg Thr Asn
    370                 375                 380

Val Leu Tyr Glu Leu Ala Gln Tyr Ala Ser Glu Pro Ser Glu Gln Glu
385                 390                 395                 400

Leu Leu Arg Lys Met Ala Ser Ser Gly Glu Gly Lys Glu Leu Tyr
                405                 410                 415

Leu Ser Trp Val Val Glu Ala Arg Arg His Ile Leu Ala Ile Leu Gln
            420                 425                 430

Asp Cys Pro Ser Leu Arg Pro Pro Ile Asp His Leu Cys Glu Leu Leu
        435                 440                 445

Pro Arg Leu Gln Ala Arg Tyr Tyr Ser Ile Ala Ser Ser Lys Val
    450                 455                 460

His Pro Asn Ser Val His Ile Cys Ala Val Val Glu Tyr Glu Thr
465                 470                 475                 480

Lys Ala Gly Arg Ile Asn Lys Gly Val Ala Thr Asn Trp Leu Arg Ala
                485                 490                 495

Lys Glu Pro Val Gly Glu Asn Gly Gly Arg Ala Leu Val Pro Met Phe
            500                 505                 510

Val Arg Lys Ser Gln Phe Arg Leu Pro Phe Lys Ala Thr Thr Pro Val
    515                 520                 525

Ile Met Val Gly Pro Gly Thr Gly Val Ala Pro Phe Ile Gly Phe Ile
530                 535                 540

Gln Glu Arg Ala Trp Leu Arg Gln Gln Gly Lys Glu Val Gly Glu Thr
545                 550                 555                 560

Leu Leu Tyr Tyr Gly Cys Arg Arg Ser Asp Glu Asp Tyr Leu Tyr Arg
                565                 570                 575

Glu Glu Leu Ala Gln Phe His Arg Asp Gly Ala Leu Thr Gln Leu Asn
            580                 585                 590

Val Ala Phe Ser Arg Glu Gln Ser His Lys Val Tyr Val Gln His Leu
    595                 600                 605

Leu Lys Gln Asp Arg Glu His Leu Trp Lys Leu Ile Glu Gly Gly Ala
610                 615                 620

His Ile Tyr Val Cys Gly Asp Ala Arg Asn Met Ala Arg Asp Val Gln
625                 630                 635                 640

Asn Thr Phe Tyr Asp Ile Val Ala Glu Leu Gly Ala Met Glu His Ala
                645                 650                 655

Gln Ala Val Asp Tyr Ile Lys Lys Leu Met Thr Lys Gly Arg Tyr Ser
            660                 665                 670

Leu Asp Val Trp Ser
        675

<210> SEQ ID NO 24
<211> LENGTH: 3259
<212> TYPE: DNA
<213> ORGANISM: Homo sapiens

<400> SEQUENCE: 24
caaggttggt ggaagtcgcg ttgtgcaggt tcgtgcccgg ctggcgcggc gtggtttcac      60
tgttacatgc cttgaagtga tgaggaggtt tctgttacta tatgctacac agcagggaca     120
ggcaaaggcc atcgcagaag aaatgtgtga gcaagctgtg gtacatggat ttctgcagga     180
tcttcactgt attagtgaat ccgataagta tgacctaaaa accgaaacag ctcctcttgt     240
tgttgtggtt tctaccacgg gcaccggaga cccacccgac acagcccgca agtttgttaa     300
ggaaatacag aaccaaacac tgccggttga tttctttgct cacctgcggt atgggttact     360
```

```
gggtctcggt gattcagaat acacctactt ttgcaatggg gggaagataa ttgataaacg    420
acttcaagag cttggagccc ggcatttcta tgacactgga catgcagatg actgtgtagg    480
tttagaactt gtggttgagc cgtggattgc tggactctgg ccagccctca gaaagcattt    540
taggtcaagc agaggacaag aggagataag tggcgcactc ccggtggcat cacctgcatc    600
cttgaggaca gaccttgtga agtcagagct gctacacatt gaatctcaag tcgagcttct    660
gagattcgat gattcaggaa gaaaggattc tgaggttttg aagcaaaatg cagtgaacag    720
caaccaatcc aatgttgtaa ttgaagactt tgagtcctca cttacccgtt cggtaccccc    780
actctcacaa gcctctctga atattcctgg tttaccccca gaatatttac aggtacatct    840
gcaggagtct cttggccagg aggaaagcca agtatctgtg acttcagcag atccagtttt    900
tcaagtgcca atttcaaagg cagttcaact tactacgaat gatgccataa aaccactct    960 gctggtagaa ttggacattt caaatacaga cttttcctat cagcctggag atgccttcag    1020
cgtgatctgc cctaacagtg attctgaggt acaaagccta ctccaaagac tgcagcttga    1080
agataaaaga gagcactgcg tccttttgaa aataaaggca gacacaaaga gaaaggagc    1140 taccttaccc cagcatatac ctgcgggatg ttctctccag ttcattttta cctggtgtct    1200
tgaaatccga gcaattccta aaaaggcatt tttgcgagcc cttgtggact ataccagtga    1260
cagtgctgaa aagcgcaggc tacaggagct gtgcagtaaa caaggggcag ccgattatag    1320
ccgctttgta cgagatgcct gtgcctgctt gttggatctc ctcctcgctt tcccttcttg    1380
ccagccacca ctcagtctcc tgctcgaaca tcttcctaaa cttcaaccca gaccatattc    1440
gtgtgcaagc tcaagtttat ttcacccagg aaagctccat tttgtcttca acattgtgga    1500
atttctgtct actgccacaa cagaggttct gcggaaggga gtatgtacag gctggctggc    1560
cttgttggtt gcttcagttc ttcagccaaa catacatgca tcccatgaag acagcgggaa    1620
agccctggct cctaagatat ccatctctcc tcgaacaaca aattctttcc acttaccaga    1680
tgacccctca atccccatca taatggtggg tccaggaacc ggcatagccc cgtttattgg    1740
gttcctacaa catagagaga aactccaaga acaacaccca gatggaaatt ttggagcaat    1800
gtggttgttt tttggctgca ggcataagga tagggattat ctattcagaa aagagctcag    1860
acatttcctt aagcatggga tcttaactca tctaaaggtt tccttctcaa gagatgctcc    1920
tgttggggag gaggaagccc cagcaaagta tgtacaagac aacatccagc ttcatggcca    1980
gcaggtggcg agaatcctcc tccaggagaa cggccatatt tatgtgtgtg gagatgcaaa    2040
gaatatggcc aaggatgtac atgatgccct tgtgcaaata ataagcaaag aggttggagt    2100
tgaaaaacta gaagcaatga aaaccctggc cactttaaaa gaagaaaaac gctaccttca    2160
ggatatttgg tcataaaacc agaaattaaa gaaagaggat taagcttttt tgactgaaag    2220
tactaaaagt cagctttact agtgccaaac ctttaaattt tcaaaagaaa atttttcttc    2280
aacatttctt gaaggacatg gagtggagat tggatcattt aacaatataa caaaacttcc    2340
tgatttgatt ttacgtatct tctatctacg cccttcctgt gcctgtgact ctccccaaat    2400
tgccctgttg ccttgagctc ttctgagcta aaggcagcct tcagtcccta tcagcgcctc    2460
ctttacttcc cagagaactt cacagagact ctgtccttcc atgcaaaggc ttcctgaaat    2520
aggggagact gactgagtag ctcattcttg tgacttacag tgccaacatt taaaaaagta    2580
tgaaaatgat ttatttttat atgatgtata cccataaaga atgctcatat taatgtactt    2640
aaattacaca tgtagagcat atctgttata tgtttatgta actatcaaat ggttatttgt    2700
```

```
tactaaagct atatttctga taaaaaatat tttaggataa ttgcctacag agggatttat    2760
ttttatgatg ctgggaaata tgaaatgtat tttaaaattt cactctgggc atatggattt    2820
atctatcacc attactttt ttaagtcac aatttcagaa ttttgggaca tttgcattca     2880
atttacaggt accagtacgt acatatttta atagaaagat acaaccttt tattttcact    2940 ccttttattt ctgctgcttg gcacattttt gagttttccc acattatttg tctccatgat   3000
accactcaag cagtgtgctg gacctaaaat actgacttta gttagtatcc ttggattttt   3060
agattcccca gtgtctaatt ccctgttata atttgcacaa acaaaacaaa atgttatgat   3120
aatctttctc cactgttcta atatatattg tatttttatt tgatagcttg ggatttaaaa   3180
catctctgtt gaaggcttt gatccttttg agaaataaag atctgaaaga aatggcataa   3240
tcttaaaaaa aaaaaaaa                                                 3259
```

<210> SEQ ID NO 25
<211> LENGTH: 18
<212> TYPE: PRT
<213> ORGANISM: Homo sapiens

<400> SEQUENCE: 25

Gly Ala Met Trp Leu Phe Phe Gly Cys Arg His Lys Asp Arg Asp Tyr
1               5                   10                  15

Leu Phe

<210> SEQ ID NO 26
<211> LENGTH: 18
<212> TYPE: PRT
<213> ORGANISM: Homo sapiens

<400> SEQUENCE: 26

Gly Glu Thr Leu Leu Tyr Tyr Gly Cys Arg Arg Ser Asp Glu Asp Tyr
1               5                   10                  15

Leu Tyr

<210> SEQ ID NO 27
<211> LENGTH: 18
<212> TYPE: PRT
<213> ORGANISM: Oryctolagus cuniculus

<400> SEQUENCE: 27

Gly Glu Thr Leu Leu Tyr Tyr Gly Cys Arg Arg Ala Ala Glu Asp Tyr
1               5                   10                  15

Leu Tyr

<210> SEQ ID NO 28
<211> LENGTH: 18
<212> TYPE: PRT
<213> ORGANISM: Drosophila melanogaster

<400> SEQUENCE: 28

Gly Glu Ser Ile Leu Tyr Phe Gly Cys Arg Lys Arg Ser Glu Asp Tyr
1               5                   10                  15

Ile Tyr

<210> SEQ ID NO 29
<211> LENGTH: 18
<212> TYPE: PRT
<213> ORGANISM: Vigna radiata

<400> SEQUENCE:

```
Gly Pro Ala Leu Leu Phe Phe Gly Cys Arg Asn Arg Gln Met Asp Phe
 1               5                  10                  15

Ile Tyr

<210> SEQ ID NO 30
<211> LENGTH: 18
<212> TYPE: PRT
<213> ORGANISM: Aspergillus niger

<400> SEQUENCE: 30

Gly Pro Thr Val Leu Phe Phe Gly Cys Arg Lys Ser Asp Glu Asp Phe
 1               5                  10                  15

Leu Tyr

<210> SEQ ID NO 31
<211> LENGTH: 18
<212> TYPE: PRT
<213> ORGANISM: Homo sapiens

<400> SEQUENCE: 31

Cys Pro Met Val Leu Val Phe Gly Cys Arg Gln Ser Lys Ile Asp His
 1               5                  10                  15

Ile Tyr

<210> SEQ ID NO 32
<211> LENGTH: 18
<212> TYPE: PRT
<213> ORGANISM: Homo sapiens

<400> SEQUENCE: 32

Gly Arg Met Thr Leu Val Phe Gly Cys Arg Arg Pro Asp Glu Asp His
 1               5                  10                  15

Ile Tyr

<210> SEQ ID NO 33
<211> LENGTH: 18
<212> TYPE: PRT
<213> ORGANISM: Homo sapiens

<400> SEQUENCE: 33

Thr Pro Met Thr Leu Val Phe Gly Cys Arg Cys Ser Gln Leu Asp His
 1               5                  10                  15

Leu Tyr

<210> SEQ ID NO 34
<211> LENGTH: 18
<212> TYPE: PRT
<213> ORGANISM: Oryctolagus cuniculus

<400> SEQUENCE: 34

Gly Arg Met Thr Leu Val Phe Gly Cys Arg His Pro Glu Glu Asp His
 1               5                  10                  15

Leu Tyr

<210> SEQ ID NO 35
<211> LENGTH: 18
<212> TYPE: PRT
<213> ORGANISM: Gallus gallus

<400> SEQUENCE: 35
```

-continued

Gly Asp Met Ile Leu Leu Phe Gly Cys Arg His Pro Asp Met Asp His
1               5                   10                  15

Ile Tyr

<210> SEQ ID NO 36
<211> LENGTH: 18
<212> TYPE: PRT
<213> ORGANISM: Escherichia coli

<400> SEQUENCE: 36

Gly Lys Asn Trp Leu Phe Phe Gly Asn Pro His Phe Thr Glu Asp Phe
1               5                   10                  15

Leu Tyr

<210> SEQ ID NO 37
<211> LENGTH: 18
<212> TYPE: PRT
<213> ORGANISM: Saccharomyces cerevisiae

<400> SEQUENCE: 37

Gly Glu Val Phe Leu Tyr Leu Gly Ser Arg His Lys Arg Glu Glu Tyr
1               5                   10                  15

Leu Tyr

<210> SEQ ID NO 38
<211> LENGTH: 18
<212> TYPE: PRT
<213> ORGANISM: Thiocapsa roseopersicina

<400> SEQUENCE: 38

Gly Arg Asn Trp Leu Ile Phe Gly Asn Arg His Phe His Arg Asp Phe
1               5                   10                  15

Leu Tyr

<210> SEQ ID NO 39
<211> LENGTH: 19
<212> TYPE: PRT
<213> ORGANISM: Pisum sativum

<400> SEQUENCE: 39

Gly Leu Ala Trp Leu Phe Leu Gly Val Ala Asn Val Asp Ser Leu Leu
1               5                   10                  15

Tyr Asp Asp

<210> SEQ ID NO 40
<211> LENGTH: 18
<212> TYPE: PRT
<213> ORGANISM: Spinacia oleracea

<400> SEQUENCE: 40

Gly Leu Ala Trp Leu Phe Leu Gly Val Pro Thr Ser Ser Ser Leu Leu
1               5                   10                  15

Tyr Lys

<210> SEQ ID NO 41
<211> LENGTH: 2097
<212> TYPE: DNA
<213> ORGANISM: Homo sapiens

<400> SEQUENCE: 41
atgaggaggt ttctgttact atatgctaca cagcagggac aggcaaaggc catcgcagaa      60

```
gaaatatgtg agcaagctgt ggtacatgga ttttctgcag atcttcactg tattagtgaa    120
tccgataagt atgacctaaa aaccgaaaca gctcctcttg ttgttgtggt ttctaccacg    180
ggcaccggag acccacccga cacagcccgc aagtttgtta aggaaataca gaaccaaaca    240
ctgccggttg atttctttgc tcacctgcgg tatgggttac tgggtctcgg tgattcagaa    300
tacacctact tttgcaatgg ggggaagata attgataaac gacttcaaga gcttggagcc    360
cggcatttct atgacactgg acatgcagat gactgtgtag gtttagaact tgtggttgag    420
ccgtggattg ctggactctg gccagccctc agaaagcatt ttaggtcaag cagaggacaa    480
gaggagataa gtggcgcact cccggtggca tcacctgcat ccttgaggac agaccttgtg    540
aagtcagagc tgctacacat tgaatctcaa gtcgagcttc tgagattcga tgattcagga    600
agaaaggatt ctgaggtttt gaagcaaaat gcagtgaaca gcaaccaatc caatgttgta    660
attgaagact ttgagtcctc acttacccgt tcggtacccc cactctcaca gcctctctg     720 aatattcctg gtttaccccc agaatattta caggtacatc tgcaggagtc tcttggccag    780
gaggaaagcc aagtatctgt gacttcagca gatccagttt ttcaagtgcc aatttcaaag    840
gcagttcaac ttactacgaa tgatgccata aaaaccactc tgctggtaga attggacatt    900
tcaaatacag acttttccta tcagcctgga gatgccttca gcgtgatctg ccctaacagt    960
gattctgagg tacaaagcct actccaaaga ctgcagcttg aagataaaag agagcactgc   1020
gtccttttga aaataaaggc agacacaaag aagaaaggag ctaccttacc ccagcatata   1080
cctgcgggat gttctctcca gttcattttt acctggtgtc ttgaaatccg agcaattcct   1140
aaaaaggcat ttttgcgagc ccttgtggac tataccagtg acagtgctga aaagcgcagg   1200
ctacaggagc tgtgcagtaa acaaggggca gccgattata gccgctttgt acgagatgcc   1260
tgtgcctgct tgttggatct cctcctcgct ttcccttctt gccagccacc actcagtctc   1320
ctgctcgaac atcttcctaa acttcaaccc agaccatatt cgtgtgcaag ctcaagttta   1380
tttcacccag gaaagctcca ttttgtcttc aacattgtgg aatttctgtc tactgccaca   1440
acagaggttc tgcggaaggg agtatgtaca ggctggctgg ccttgttggt tgcttcagtt   1500
cttcagccaa acatacatgc atcccatgaa gacagcggga agccctggc tcctaagata    1560 tccatctctc ctcgaacaac aaattctttc cacttaccag atgaccctc aatccccatc    1620 ataatggtgg gtccaggaac cggcatagcc ccgtttattg ggttcctaca acatagagag   1680
aaactccaag aacaacaccc cagatggaaat tttggagcaa tgtggttgtt ttttggctgc   1740
aggcataagg atagggatta tctattcaga aaagagctca gacatttcct taagcatggg   1800
atcttaactc atctaaaggt ttccttctca agagatgctc ctgttgggga ggaggaagcc   1860
ccagcaaagt atgtacaaga caacatccag cttcatggcc agcaggtggc gagaatcctc   1920
ctccaggaga acggccatat ttatgtgtgt ggagatgcaa agaatatggc caaggatgta   1980
catgatgccc ttgtgcaaat aataagcaaa gaggttggag ttgaaaaact agaagcaatg   2040
aaaaccctgg ccactttaaa agaagaaaaa cgctaccttc aggatatttg gtcataa      2097
```

<210> SEQ ID NO 42
<211> LENGTH: 698
<212> TYPE: PRT
<213> ORGANISM: Homo sapiens

<400> SEQUENCE: 42

Met Arg Arg Phe Leu Leu Leu Tyr Ala Thr Gln Gln Gly Gln Ala Lys
 1               5                  10                  15

```
Ala Ile Ala Glu Glu Ile Cys Glu Gln Ala Val Val His Gly Phe Ser
         20                  25                  30
Ala Asp Leu His Cys Ile Ser Glu Ser Asp Lys Tyr Asp Leu Lys Thr
             35                  40                  45
Glu Thr Ala Pro Leu Val Val Val Ser Thr Thr Gly Thr Gly Asp
         50                  55                  60
Pro Pro Asp Thr Ala Arg Lys Phe Val Lys Glu Ile Gln Asn Gln Thr
 65                  70                  75                  80
Leu Pro Val Asp Phe Phe Ala His Leu Arg Tyr Gly Leu Leu Gly Leu
                 85                  90                  95
Gly Asp Ser Glu Tyr Thr Tyr Phe Cys Asn Gly Gly Lys Ile Ile Asp
             100                 105                 110
Lys Arg Leu Gln Glu Leu Gly Ala Arg His Phe Tyr Asp Thr Gly His
             115                 120                 125
Ala Asp Asp Cys Val Gly Leu Glu Leu Val Val Glu Pro Trp Ile Ala
         130                 135                 140
Gly Leu Trp Pro Ala Leu Arg Lys His Phe Arg Ser Ser Arg Gly Gln
145                 150                 155                 160
Glu Glu Ile Ser Gly Ala Leu Pro Val Ala Ser Pro Ala Ser Leu Arg
                 165                 170                 175
Thr Asp Leu Val Lys Ser Glu Leu Leu His Ile Glu Ser Gln Val Glu
             180                 185                 190
Leu Leu Arg Phe Asp Asp Ser Gly Arg Lys Asp Ser Glu Val Leu Lys
             195                 200                 205
Gln Asn Ala Val Asn Ser Asn Gln Ser Asn Val Val Ile Glu Asp Phe
         210                 215                 220
Glu Ser Ser Leu Thr Arg Ser Val Pro Pro Leu Ser Gln Ala Ser Leu
225                 230                 235                 240
Asn Ile Pro Gly Leu Pro Pro Glu Tyr Leu Gln Val His Leu Gln Glu
                 245                 250                 255
Ser Leu Gly Gln Glu Glu Ser Gln Val Ser Val Thr Ser Ala Asp Pro
             260                 265                 270
Val Phe Gln Val Pro Ile Ser Lys Ala Val Gln Leu Thr Thr Asn Asp
             275                 280                 285
Ala Ile Lys Thr Thr Leu Leu Val Glu Leu Asp Ile Ser Asn Thr Asp
         290                 295                 300
Phe Ser Tyr Gln Pro Gly Asp Ala Phe Ser Val Ile Cys Pro Asn Ser
305                 310                 315                 320
Asp Ser Glu Val Gln Ser Leu Leu Gln Arg Leu Gln Leu Glu Asp Lys
             325                 330                 335
Arg Glu His Cys Val Leu Leu Lys Ile Lys Ala Asp Thr Lys Lys Lys
             340                 345                 350
Gly Ala Thr Leu Pro Gln His Ile Pro Ala Gly Cys Ser Leu Gln Phe
             355                 360                 365
Ile Phe Thr Trp Cys Leu Glu Ile Arg Ala Ile Pro Lys Lys Ala Phe
         370                 375                 380
Leu Arg Ala Leu Val Asp Tyr Thr Ser Asp Ser Ala Glu Lys Arg Arg
385                 390                 395                 400
Leu Gln Glu Leu Cys Ser Lys Gln Gly Ala Ala Asp Tyr Ser Arg Phe
                 405                 410                 415
Val Arg Asp Ala Cys Ala Cys Leu Leu Asp Leu Leu Leu Ala Phe Pro
         420                 425                 430
```

| | | | | | | | | | | | |
|---|---|---|---|---|---|---|---|---|---|---|---|
|Ser|Cys|Gln|Pro|Pro|Leu|Ser|Leu|Leu|Leu|Glu|His|Leu|Pro|Lys|Leu|
| |435| | | |440| | | |445| | |

| Gln | Pro | Arg | Pro | Tyr | Ser | Cys | Ala | Ser | Ser | Ser | Leu | Phe | His | Pro | Gly |
|---|---|---|---|---|---|---|---|---|---|---|---|---|---|---|---|
| | | 450 | | | | 455 | | | | 460 | | | | | |

Lys Leu His Phe Val Phe Asn Ile Val Glu Phe Leu Ser Thr Ala Thr
465                 470                 475                 480

Thr Glu Val Leu Arg Lys Gly Val Cys Thr Gly Trp Leu Ala Leu Leu
                485                 490                 495

Val Ala Ser Val Leu Gln Pro Asn Ile His Ala Ser His Glu Asp Ser
            500                 505                 510

Gly Lys Ala Leu Ala Pro Lys Ile Ser Ile Ser Pro Arg Thr Thr Asn
            515                 520                 525

Ser Phe His Leu Pro Asp Asp Pro Ser Ile Pro Ile Ile Met Val Gly
530                 535                 540

Pro Gly Thr Gly Ile Ala Pro Phe Ile Gly Phe Leu Gln His Arg Glu
545                 550                 555                 560

Lys Leu Gln Glu Gln His Pro Asp Gly Asn Phe Gly Ala Met Trp Leu
                565                 570                 575

Phe Phe Gly Cys Arg His Lys Asp Arg Asp Tyr Leu Phe Arg Lys Glu
            580                 585                 590

Leu Arg His Phe Leu Lys His Gly Ile Leu Thr His Leu Lys Val Ser
            595                 600                 605

Phe Ser Arg Asp Ala Pro Val Gly Glu Glu Ala Pro Ala Lys Tyr
610                 615                 620

Val Gln Asp Asn Ile Gln Leu His Gly Gln Gln Val Ala Arg Ile Leu
625                 630                 635                 640

Leu Gln Glu Asn Gly His Ile Tyr Val Cys Gly Asp Ala Lys Asn Met
                645                 650                 655

Ala Lys Asp Val His Asp Ala Leu Val Gln Ile Ile Ser Lys Glu Val
            660                 665                 670

Gly Val Glu Lys Leu Glu Ala Met Lys Thr Leu Ala Thr Leu Lys Glu
            675                 680                 685

Glu Lys Arg Tyr Leu Gln Asp Ile Trp Ser
690                 695

<210> SEQ ID NO 43
<211> LENGTH: 2097
<212> TYPE: DNA
<213> ORGANISM: Homo sapiens

<400> SEQUENCE: 43

```
atgaggaggt tctgttact atatgctaca cagcagggac aggcaaaggc catcgcagaa        60
gaaatgtgtg agcaagctgt ggtacatgga ttttctgcag atcttcacta tattagtgaa      120
tccgataagt atgacctaaa aaccgaaaca gctcctcttg ttgttgtggt ttctaccacg      180
ggcaccggag acccacccga cacagcccgc aagtttgtta ggaaatacta gaaccaaaca      240
ctgccggttg atttctttgc tcacctgcgg tatgggttac tgggtctcgg tgattcagaa      300
tacacctact tttgcaatgg ggggaagata attgataaac gacttcaaga gcttggagcc      360
cggcatttct atgacactgg acatgcagat gactgtgtag gtttagaact tgtggttgag      420
ccgtggattg ctggactctg gccagccctc agaaagcatt ttaggtcaag cagaggacaa      480
gaggagataa gtggcgcact cccggtggca tcacctgcat ccttgaggac agaccttgtg      540
aagtcagagc tgctacacat tgaatctcaa gtcgagcttc tgagattcga tgattcagga      600
```

```
agaaaggatt ctgaggtttt gaagcaaaat gcagtgaaca gcaaccaatc caatgttgta      660
attgaagact ttgagtcctc acttacccgt tcggtacccc cactctcaca agcctctctg      720
aatattcctg gtttaccccc agaatattta caggtacatc tgcaggagtc tcttggccag      780
gaggaaagcc aagtatctgt gacttcagca gatccagttt ttcaagtgcc aatttcaaag      840
gcagttcaac ttactacgaa tgatgccata aaaaccactc tgctggtaga attggacatt      900
tcaaatacag acttttccta tcagcctgga gatgccttca gcgtgatctg ccctaacagt      960
gattctgagg tacaaagcct actccaaaga ctgcagcttg aagataaaag agagcactgc     1020
gtccttttga aaataaaggc agacacaaag aagaaaggag ctaccttacc ccagcatata     1080
cctgcgggat gttctctcca gttcattttt acctggtgtc ttgaaatccg agcaattcct     1140
aaaaaggcat ttttgcgagc ccttgtggac tataccagtg acagtgctga aaagcgcagg     1200
ctacaggagc tgtgcagtaa acaaggggca gccgattata gccgctttgt acgagatgcc     1260
tgtgcctgct gtttggatct cctcctcgct ttcccttctt gccagccacc actcagtctc     1320
ctgctcgaac atcttcctaa acttcaaccc agaccatatt cgtgtgcaag ctcaagttta     1380
tttcacccag gaaagctcca tttttgtcttc aacattgtgg aatttctgtc tactgccaca     1440
acagaggttc tgcggaaggg agtatgtaca ggctggctgg ccttgttggt tgcttcagtt     1500
cttcagccaa acatacatgc atcccatgaa gacagcggga aagccctggc tcctaagata     1560
tccatctctc ctcgaacaac aaattctttc cacttaccag atgacccctc aatccccatc     1620
ataatggtgg gtccaggaac cggcatagcc ccgtttattg ggttcctaca acatagagag     1680
aaactccaag aacaacaccc agatggaaat tttggagcaa tgtggttgtt ttttggctgc     1740
aggcataagg ataggggatta tctattcaga aaagagctca gacatttcct taagcatggg     1800
atcttaactc atctaaaggt ttccttctca agagatgctc ctgttgggga ggaggaagcc     1860
ccagcaaagt atgtacaaga caacatccag cttcatggcc agcaggtggc gagaatcctc     1920
ctccaggaga acggccatat ttatgtgtgt ggagatgcaa agaatatggc caaggatgta     1980
catgatgccc ttgtgcaaat aataagcaaa gaggttggag ttgaaaaact agaagcaatg     2040
aaaaccctgg ccactttaaa agaagaaaaa cgctaccttc aggatatttg gtcataa       2097
```

<210> SEQ ID NO 44
<211> LENGTH: 698
<212> TYPE: PRT
<213> ORGANISM: Homo sapiens

<400> SEQUENCE: 44

```
Met Arg Arg Phe Leu Leu Leu Tyr Ala Thr Gln Gln Gly Gln Ala Lys
 1               5                  10                  15

Ala Ile Ala Glu Glu Met Cys Glu Gln Ala Val Val His Gly Phe Ser
                20                  25                  30

Ala Asp Leu His Thr Ile Ser Glu Ser Asp Lys Tyr Asp Leu Lys Thr
            35                  40                  45

Glu Thr Ala Pro Leu Val Val Val Ser Thr Thr Gly Thr Gly Asp
        50                  55                  60

Pro Pro Asp Thr Ala Arg Lys Phe Val Lys Glu Ile Gln Asn Gln Thr
65                  70                  75                  80

Leu Pro Val Asp Phe Phe Ala His Leu Arg Tyr Gly Leu Leu Gly Leu
                85                  90                  95

Gly Asp Ser Glu Tyr Thr Tyr Phe Cys Asn Gly Gly Lys Ile Ile Asp
            100                 105                 110
```

-continued

```
Lys Arg Leu Gln Glu Leu Gly Ala Arg His Phe Tyr Asp Thr Gly His
        115                 120                 125
Ala Asp Asp Cys Val Gly Leu Glu Leu Val Val Glu Pro Trp Ile Ala
    130                 135                 140
Gly Leu Trp Pro Ala Leu Arg Lys His Phe Arg Ser Ser Arg Gly Gln
145                 150                 155                 160
Glu Glu Ile Ser Gly Ala Leu Pro Val Ala Ser Pro Ala Ser Leu Arg
                165                 170                 175
Thr Asp Leu Val Lys Ser Glu Leu Leu His Ile Glu Ser Gln Val Glu
            180                 185                 190
Leu Leu Arg Phe Asp Asp Ser Gly Arg Lys Asp Ser Glu Val Leu Lys
        195                 200                 205
Gln Asn Ala Val Asn Ser Asn Gln Ser Asn Val Ile Glu Asp Phe
    210                 215                 220
Glu Ser Ser Leu Thr Arg Ser Val Pro Pro Leu Ser Gln Ala Ser Leu
225                 230                 235                 240
Asn Ile Pro Gly Leu Pro Pro Glu Tyr Leu Gln Val His Leu Gln Glu
                245                 250                 255
Ser Leu Gly Gln Glu Glu Ser Gln Val Ser Val Thr Ser Ala Asp Pro
            260                 265                 270
Val Phe Gln Val Pro Ile Ser Lys Ala Val Gln Leu Thr Thr Asn Asp
        275                 280                 285
Ala Ile Lys Thr Thr Leu Leu Val Glu Leu Asp Ile Ser Asn Thr Asp
    290                 295                 300
Phe Ser Tyr Gln Pro Gly Asp Ala Phe Ser Val Ile Cys Pro Asn Ser
305                 310                 315                 320
Asp Ser Glu Val Gln Ser Leu Leu Gln Arg Leu Gln Leu Glu Asp Lys
                325                 330                 335
Arg Glu His Cys Val Leu Leu Lys Ile Lys Ala Asp Thr Lys Lys Lys
            340                 345                 350
Gly Ala Thr Leu Pro Gln His Ile Pro Ala Gly Cys Ser Leu Gln Phe
        355                 360                 365
Ile Phe Thr Trp Cys Leu Glu Ile Arg Ala Ile Pro Lys Lys Ala Phe
    370                 375                 380
Leu Arg Ala Leu Val Asp Tyr Thr Ser Asp Ser Ala Glu Lys Arg Arg
385                 390                 395                 400
Leu Gln Glu Leu Cys Ser Lys Gln Gly Ala Ala Asp Tyr Ser Arg Phe
                405                 410                 415
Val Arg Asp Ala Cys Ala Cys Leu Leu Asp Leu Leu Leu Ala Phe Pro
            420                 425                 430
Ser Cys Gln Pro Pro Leu Ser Leu Leu Leu Glu His Leu Pro Lys Leu
        435                 440                 445
Gln Pro Arg Pro Tyr Ser Cys Ala Ser Ser Ser Leu Phe His Pro Gly
    450                 455                 460
Lys Leu His Phe Val Phe Asn Ile Val Glu Phe Leu Ser Thr Ala Thr
465                 470                 475                 480
Thr Glu Val Leu Arg Lys Gly Val Cys Thr Gly Trp Leu Ala Leu Leu
                485                 490                 495
Val Ala Ser Val Leu Gln Pro Asn Ile His Ala Ser His Glu Asp Ser
            500                 505                 510
Gly Lys Ala Leu Ala Pro Lys Ile Ser Ile Ser Pro Arg Thr Thr Asn
        515                 520                 525
Ser Phe His Leu Pro Asp Asp Pro Ser Ile Pro Ile Ile Met Val Gly
```

```
                530             535             540
Pro Gly Thr Gly Ile Ala Pro Phe Ile Gly Phe Leu Gln His Arg Glu
545                 550                 555                 560

Lys Leu Gln Glu Gln His Pro Asp Gly Asn Phe Gly Ala Met Trp Leu
                565                 570                 575

Phe Phe Gly Cys Arg His Lys Asp Arg Asp Tyr Leu Phe Arg Lys Glu
            580                 585                 590

Leu Arg His Phe Leu Lys His Gly Ile Leu Thr His Leu Lys Val Ser
        595                 600                 605

Phe Ser Arg Asp Ala Pro Val Gly Glu Glu Ala Pro Ala Lys Tyr
    610                 615                 620

Val Gln Asp Asn Ile Gln Leu His Gly Gln Gln Val Ala Arg Ile Leu
625                 630                 635                 640

Leu Gln Glu Asn Gly His Ile Tyr Val Cys Gly Asp Ala Lys Asn Met
                645                 650                 655

Ala Lys Asp Val His Asp Ala Leu Val Gln Ile Ile Ser Lys Glu Val
            660                 665                 670

Gly Val Glu Lys Leu Glu Ala Met Lys Thr Leu Ala Thr Leu Lys Glu
        675                 680                 685

Glu Lys Arg Tyr Leu Gln Asp Ile Trp Ser
    690                 695

<210> SEQ ID NO 45
<211> LENGTH: 2094
<212> TYPE: DNA
<213> ORGANISM: Homo sapiens

<400> SEQUENCE: 45
atgaggaggt tctgttact  atatgctaca cagcagggac aggcaaaggc catcgcagaa      60
gaaatgtgtg agcaagctgt ggtacatgga ttttctgcag atcttcactg tattagtgaa     120
tccgataagt atgacctaaa aaccgaaaca gctcctcttg ttgttgtggt ttctaccacg     180
ggcaccggag acccacccga cacagcccgc aagtttgtta aggaaataca gaaccaaaca     240
ctgccggttg atttctttgc tcacctgcgg tatgggttac tgggtctcgg tgattcagaa     300
tacacctact tttgcaatgg ggggaagata attgataaac gacttcaaga gcttggagcc     360
cggcatttct atgacactgg acatgcagat gactgtgtag gtttagaact tgtggttgag     420
ccgtggattg ctggactctg gccagccctc agaaagcatt ttaggtcaag cagaggacaa     480
gaggagataa gtggcgcact cccggtggca tcacctgcat ccttgaggac agaccttgtg     540
aagtcagagc tgctacacat tgaatctcaa gtcgagcttc tgagattcga tgattcagga     600
agaaaggatt ctgaggtttt gaagcaaaat gcagtgaaca gcaaccaatc caatgttgta     660
attgaagact ttgagtcctc acttacccgt tcggtacccc cactctcaca gcctctctg      720 aatattcctg gtttaccccc agaatattta caggtacatc tgcaggagtc tcttggccag     780
gaggaaagcc aagtatctgt gacttcagca gatccagttt ttcaagtgcc aatttcaaag     840
gcagttcaac ttactacgaa tgatgccata aaaaccactc tgctggtaga attggacatt     900
tcaaatacag acttttccta tcagcctgga gatgccttca gcgtgatctg ccctaacagt     960
gattctgagg tacaaagcct actccaagac ctgcagcttg aagataaaag agagcactgc    1020
gtccttttga aaataaaggc agacacaaag aagaaggag  ctaccttacc ccagcatata    1080
cctgcgggat gttctctcca gttcatttt  acctggtgtc ttgaaatccg agcaattcct    1140
aaaaaggcat ttttgcgagc ccttgtggac tataccagtg acagtgctga aaagcgcagg    1200
```

```
ctacaggagc tgtgcagtaa acaaggggca gccgattata gccgctttgt acgagatgcc   1260
tgtgcctgct tgttggatct cctcctcgct ttcccttctt gccagccacc actcagtctc   1320
ctgctcgaac atcttcctaa acttcaaccc agaccatatt cgtgtgcaag ctcaagttta   1380
tttcacccag gaaagctcca ttttgtcttc aacattgtgg aatttctgtc tactgccaca   1440
acagaggttc tgcggaaggg agtatgtaca ggctggctgg ccttgttggt tgcttcagtt   1500
cttcagccaa acatacatgc atcccatgaa gacagcggga aagccctggc tcctaagata   1560
tccatctctc ctcgaacaac aaattctttc cacttaccag atgacccctc aatccccatc   1620
ataatggtgg gtccaggaac cggcatagcc ccgtttattg ggttcctaca acatagagag   1680
aaactccaag aacaacaccc agatggaaat tttggagcaa tgtggttttt tggctgcagg   1740
cataaggata gggattatct attcagaaaa gagctcagac atttccttaa gcatgggatc   1800
ttaactcatc taaggtttc cttctcaaga gatgctcctg ttggggagga ggaagcccca   1860
gcaaagtatg tacaagacaa catccagctt catggccagc aggtggcgag aatcctcctc   1920
caggagaacg gccatattta tgtgtgtgga gatgcaaaga atatggccaa ggatgtacat   1980
gatgcccttg tgcaaataat aagcaaagag gttggagttg aaaaactaga agcaatgaaa   2040
accctggcca cttaaaaaga gaaaaacgc taccttcagg atatttggtc ataa         2094
```

<210> SEQ ID NO 46
<211> LENGTH: 697
<212> TYPE: PRT
<213> ORGANISM: Homo sapiens

<400> SEQUENCE: 46

```
Met Arg Arg Phe Leu Leu Leu Tyr Ala Thr Gln Gln Gly Gln Ala Lys
 1               5                  10                  15

Ala Ile Ala Glu Glu Met Cys Glu Gln Ala Val Val His Gly Phe Ser
                20                  25                  30

Ala Asp Leu His Cys Ile Ser Glu Ser Asp Lys Tyr Asp Leu Lys Thr
            35                  40                  45

Glu Thr Ala Pro Leu Val Val Val Ser Thr Gly Thr Gly Asp
        50                  55                  60

Pro Pro Asp Thr Ala Arg Lys Phe Val Lys Glu Ile Gln Asn Gln Thr
65                  70                  75                  80

Leu Pro Val Asp Phe Phe Ala His Leu Arg Tyr Gly Leu Gly Leu
                85                  90                  95

Gly Asp Ser Glu Tyr Thr Tyr Phe Cys Asn Gly Gly Lys Ile Ile Asp
            100                 105                 110

Lys Arg Leu Gln Glu Leu Gly Ala Arg His Phe Tyr Asp Thr Gly His
        115                 120                 125

Ala Asp Asp Cys Val Gly Leu Glu Leu Val Val Glu Pro Trp Ile Ala
    130                 135                 140

Gly Leu Trp Pro Ala Leu Arg Lys His Phe Arg Ser Ser Arg Gly Gln
145                 150                 155                 160

Glu Glu Ile Ser Gly Ala Leu Pro Val Ala Ser Pro Ala Ser Leu Arg
                165                 170                 175

Thr Asp Leu Val Lys Ser Glu Leu Leu His Ile Glu Ser Gln Val Glu
            180                 185                 190

Leu Leu Arg Phe Asp Asp Ser Gly Arg Lys Asp Ser Glu Val Leu Lys
        195                 200                 205

Gln Asn Ala Val Asn Ser Asn Gln Ser Asn Val Val Ile Glu Asp Phe
```

-continued

```
            210                 215                 220
Glu Ser Ser Leu Thr Arg Ser Val Pro Pro Leu Ser Gln Ala Ser Leu
225                 230                 235                 240

Asn Ile Pro Gly Leu Pro Pro Glu Tyr Leu Gln Val His Leu Gln Glu
                245                 250                 255

Ser Leu Gly Gln Glu Glu Ser Gln Val Ser Val Thr Ser Ala Asp Pro
            260                 265                 270

Val Phe Gln Val Pro Ile Ser Lys Ala Val Gln Leu Thr Thr Asn Asp
        275                 280                 285

Ala Ile Lys Thr Thr Leu Leu Val Glu Leu Asp Ile Ser Asn Thr Asp
290                 295                 300

Phe Ser Tyr Gln Pro Gly Asp Ala Phe Ser Val Ile Cys Pro Asn Ser
305                 310                 315                 320

Asp Ser Glu Val Gln Ser Leu Leu Gln Arg Leu Gln Leu Glu Asp Lys
            325                 330                 335

Arg Glu His Cys Val Leu Leu Lys Ile Lys Ala Asp Thr Lys Lys Lys
                340                 345                 350

Gly Ala Thr Leu Pro Gln His Ile Pro Ala Gly Cys Ser Leu Gln Phe
            355                 360                 365

Ile Phe Thr Trp Cys Leu Glu Ile Arg Ala Ile Pro Lys Lys Ala Phe
        370                 375                 380

Leu Arg Ala Leu Val Asp Tyr Thr Ser Asp Ser Ala Glu Lys Arg Arg
385                 390                 395                 400

Leu Gln Glu Leu Cys Ser Lys Gln Gly Ala Ala Asp Tyr Ser Arg Phe
                405                 410                 415

Val Arg Asp Ala Cys Ala Cys Leu Leu Asp Leu Leu Leu Ala Phe Pro
            420                 425                 430

Ser Cys Gln Pro Pro Leu Ser Leu Leu Leu Glu His Leu Pro Lys Leu
        435                 440                 445

Gln Pro Arg Pro Tyr Ser Cys Ala Ser Ser Ser Leu Phe His Pro Gly
    450                 455                 460

Lys Leu His Phe Val Phe Asn Ile Val Glu Phe Leu Ser Thr Ala Thr
465                 470                 475                 480

Thr Glu Val Leu Arg Lys Gly Val Cys Thr Gly Trp Leu Ala Leu Leu
                485                 490                 495

Val Ala Ser Val Leu Gln Pro Asn Ile His Ala Ser His Glu Asp Ser
            500                 505                 510

Gly Lys Ala Leu Ala Pro Lys Ile Ser Ile Ser Pro Arg Thr Thr Asn
        515                 520                 525

Ser Phe His Leu Pro Asp Asp Pro Ser Ile Pro Ile Ile Met Val Gly
    530                 535                 540

Pro Gly Thr Gly Ile Ala Pro Phe Ile Gly Phe Leu Gln His Arg Glu
545                 550                 555                 560

Lys Leu Gln Glu Gln His Pro Asp Gly Asn Phe Gly Ala Met Trp Phe
                565                 570                 575

Phe Gly Cys Arg His Lys Asp Arg Asp Tyr Leu Phe Arg Lys Glu Leu
            580                 585                 590

Arg His Phe Leu Lys His Gly Ile Leu Thr His Leu Lys Val Ser Phe
        595                 600                 605

Ser Arg Asp Ala Pro Val Gly Glu Glu Ala Pro Ala Lys Tyr Val
    610                 615                 620

Gln Asp Asn Ile Gln Leu His Gly Gln Gln Val Ala Arg Ile Leu Leu
625                 630                 635                 640
```

```
Gln Glu Asn Gly His Ile Tyr Val Cys Gly Asp Ala Lys Asn Met Ala
            645                 650                 655

Lys Asp Val His Asp Ala Leu Val Gln Ile Ile Ser Lys Glu Val Gly
        660                 665                 670

Val Glu Lys Leu Glu Ala Met Lys Thr Leu Ala Thr Leu Lys Glu Glu
    675                 680                 685

Lys Arg Tyr Leu Gln Asp Ile Trp Ser
    690                 695

<210> SEQ ID NO 47
<211> LENGTH: 2093
<212> TYPE: DNA
<213> ORGANISM: Homo sapiens

<400> SEQUENCE: 47
atgaggaggt ttctgttact atatgctaca cagcagggac aggcaaaggc catcgcagaa      60
gaaatgtgtg agcaagctgt ggtacatgga ttttctgcag atcttcactg tattagtgaa     120
tccgataagt atgacctaaa aaccgaaaca gctcctcttg ttgttgtggt ttctaccacg     180
ggcaccggag acccacccga cacagcccgc aagtttgtta aggaaataca gaaccaaaca     240
ctgccggttg atttctttgc tcacctgcgg tatgggttac tgggtctcgg tgattcagaa     300
tacacctact tttgcaatgg ggggaagata attgataaac gacttcaaga gcttggagcc     360
cggcatttct atgacactgg acatgcagat gactgtgtag gtttagaact tgtggttgag     420
ccgtggattg ctggactctg gccagccctc agaaagcatt ttaggtcaag cagaggacaa     480
gaggagataa gtggcgcact cccggtggca tcacctgcat ccttgaggac agaccttgtg     540
aagtcagagc tgctacacat tgaatctcaa gtcgagcttc tgagattcga tgattcagga     600
agaaaggatt ctgaggtttt gaagcaaaat gcagtgaaca gcaaccaatc caatgttgta     660
attgaagact ttgagtcctc acttacccgt tcggtacccc cactctcaca gcctctctg      720 aatattcctg gtttaccccc agaatattta caggtacatc tgcaggagtc tcttggccag     780
gaggaaagcc aagtatctgt gacttcagca gatccagttt ttcaagtgcc aatttcaaag     840
gcagttcaac ttactacgaa tgatgccata aaaaccactc tgctggtaga attggacatt     900
tcaaatacag acttttccta tcagcctgga gatgccttca gcgtgatctg ccctaacagt     960
gattctgagg tacaaagcct actccaaaga ctgcagcttg aagataaaag agagcactgc    1020
gtccttttga aaataaaggc agacacaaag aagaaaggag ctaccttacc ccagcatata    1080
cctgcgggat gttctctcca gttcattttt acctggtgtc ttgaaatccg agcaattcct    1140
aaaaaggcat ttttgcgagc ccttgtggac tataccagtg acagtgctga aaagcgcagg    1200
ctacaggagc tgtgcagtaa caagggca gccgattata gccgctttgt acgagatgcc    1260
tgtgcctgct gttggatct cctcctcgct ttcccttctt gccagccacc actcagtctc    1320
ctgctcgaac atcttcctaa acttcaaccc agaccatatt cgtgtgcaag ctcaagttta    1380
tttcacccag gaaagctcca tttttgtcttc aacattgtgg aatttctgtc tactgccaca    1440
acagaggttc tgcggaaggg agtatgtaca ggctggctgg ccttgttggt tgcttcagtt    1500
cttcagccaa acatacatgc atcccatgaa gacagcggga aagccctggc tcctaagata    1560
tccatctctc ctcgaacaac aaattctttc cacttaccag atgacccctc aatccccatc    1620
ataatggtgg gtccaggaac cggcatagcc ccgtttattg ggttcctaca acatagaaac    1680
tccaagaaca cacccagat ggaaattttg gagcaatgtg gttgtttttt ggctgcaggc    1740
```

-continued

```
ataaggatag ggattatcta ttcagaaaag agctcagaca tttccttaag catgggatct    1800
taactcatct aaaggtttcc ttctcaagag atgctcctgt tggggaggag gaagccccag    1860
caaagtatgt acaagacaac atccagcttc atggccagca ggtggcgaga atcctcctcc    1920
aggagaacgg ccatatttat gtgtgtggag atgcaaagaa tatggccaag gatgtacatg    1980
atgcccttgt gcaaataata agcaaagagg ttggagttga aaaactagaa gcaatgaaaa    2040
ccctggccac tttaaaagaa gaaaacgct accttcagga tatttggtca taa            2093
```

<210> SEQ ID NO 48
<211> LENGTH: 689
<212> TYPE: PRT
<213> ORGANISM: Homo sapiens

<400> SEQUENCE: 48

```
Arg Arg Phe Leu Leu Leu Tyr Ala Thr Gln Gln Gly Gln Ala Lys Ala
  1               5                  10                  15

Ile Ala Glu Glu Met Cys Glu Gln Ala Val Val His Gly Phe Ser Ala
                 20                  25                  30

Asp Leu His Cys Ile Ser Glu Ser Asp Lys Tyr Asp Leu Lys Thr Glu
             35                  40                  45

Thr Ala Pro Leu Val Val Val Ser Thr Thr Gly Thr Gly Asp Pro
         50                  55                  60

Pro Asp Thr Ala Arg Lys Phe Val Lys Glu Ile Gln Asn Gln Thr Leu
 65                  70                  75                  80

Pro Val Asp Phe Phe Ala His Leu Arg Tyr Gly Leu Leu Gly Leu Gly
                 85                  90                  95

Asp Ser Glu Tyr Thr Tyr Phe Cys Asn Gly Gly Lys Ile Ile Asp Lys
                100                 105                 110

Arg Leu Gln Glu Leu Gly Ala Arg His Phe Tyr Asp Thr Gly His Ala
            115                 120                 125

Asp Asp Cys Val Gly Leu Glu Leu Val Val Glu Pro Trp Ile Ala Gly
        130                 135                 140

Leu Trp Pro Ala Leu Arg Lys His Phe Arg Ser Ser Arg Gly Gln Glu
145                 150                 155                 160

Glu Ile Ser Gly Ala Leu Pro Val Ala Ser Pro Ala Ser Leu Arg Thr
                165                 170                 175

Asp Leu Val Lys Ser Glu Leu Leu His Ile Glu Ser Gln Val Glu Leu
            180                 185                 190

Leu Arg Phe Asp Asp Ser Gly Arg Lys Asp Ser Glu Val Leu Lys Gln
        195                 200                 205

Asn Ala Val Asn Ser Asn Gln Ser Asn Val Val Ile Glu Asp Phe Glu
    210                 215                 220

Ser Ser Leu Thr Arg Ser Val Pro Pro Leu Ser Gln Ala Ser Leu Asn
225                 230                 235                 240

Ile Pro Gly Leu Pro Pro Glu Tyr Leu Gln Val His Leu Gln Glu Ser
                245                 250                 255

Leu Gly Gln Glu Glu Ser Gln Val Ser Val Thr Ser Ala Asp Pro Val
            260                 265                 270

Phe Gln Val Pro Ile Ser Lys Ala Val Gln Leu Thr Thr Asn Asp Ala
        275                 280                 285

Ile Lys Thr Thr Leu Leu Val Glu Leu Asp Ile Ser Asn Thr Asp Phe
    290                 295                 300

Ser Tyr Gln Pro Gly Asp Ala Phe Ser Val Ile Cys Pro Asn Ser Asp
305                 310                 315                 320
```

```
Ser Glu Val Gln Ser Leu Leu Gln Arg Leu Gln Leu Glu Asp Lys Arg
            325                 330                 335

Glu His Cys Val Leu Leu Lys Ile Lys Ala Asp Thr Lys Lys Lys Gly
        340                 345                 350

Ala Thr Leu Pro Gln His Ile Pro Ala Gly Cys Ser Leu Gln Phe Ile
            355                 360                 365

Phe Thr Trp Cys Leu Glu Ile Arg Ala Ile Pro Lys Lys Ala Phe Leu
        370                 375                 380

Arg Ala Leu Val Asp Tyr Thr Ser Asp Ser Ala Glu Lys Arg Arg Leu
385                 390                 395                 400

Gln Glu Leu Cys Ser Lys Gln Gly Ala Ala Asp Tyr Ser Arg Phe Val
            405                 410                 415

Arg Asp Ala Cys Ala Cys Leu Leu Asp Leu Leu Ala Phe Pro Ser
            420                 425                 430

Cys Gln Pro Pro Leu Ser Leu Leu Glu His Leu Pro Lys Leu Gln
            435                 440                 445

Pro Arg Pro Tyr Ser Cys Ala Ser Ser Ser Leu Phe His Pro Gly Lys
        450                 455                 460

Leu His Phe Val Phe Asn Ile Val Glu Phe Leu Ser Thr Ala Thr Thr
465                 470                 475                 480

Glu Val Leu Arg Lys Gly Val Cys Thr Gly Trp Leu Ala Leu Leu Val
            485                 490                 495

Ala Ser Val Leu Gln Pro Asn Ile His Ala Ser His Glu Asp Ser Gly
            500                 505                 510

Lys Ala Leu Ala Pro Lys Ile Ser Ile Ser Pro Arg Thr Thr Asn Ser
            515                 520                 525

Phe His Leu Pro Asp Asp Pro Ser Ile Pro Ile Ile Met Val Gly Pro
        530                 535                 540

Gly Thr Gly Ile Ala Pro Phe Ile Gly Phe Leu Gln His Arg Asn Ser
545                 550                 555                 560

Lys Asn Asn Thr Gln Met Glu Ile Leu Glu Gln Cys Gly Cys Phe Leu
            565                 570                 575

Ala Ala Gly Ile Arg Ile Gly Ile Ile Tyr Ser Glu Lys Ser Ser Asp
            580                 585                 590

Ile Ser Leu Ser Met Gly Ser Leu Ile Arg Phe Pro Ser Gln Glu Met
            595                 600                 605

Leu Leu Leu Gly Arg Arg Lys Pro Gln Gln Ser Met Tyr Lys Thr Thr
            610                 615                 620

Ser Ser Phe Met Ala Ser Arg Trp Arg Glu Ser Ser Arg Arg Thr
625                 630                 635                 640

Ala Ile Phe Met Cys Val Glu Met Gln Arg Ile Trp Pro Arg Met Tyr
            645                 650                 655

Met Met Pro Leu Cys Lys Ala Lys Arg Leu Glu Leu Lys Asn Lys Gln
            660                 665                 670

Lys Pro Trp Pro Leu Lys Lys Lys Asn Ala Thr Phe Arg Ile Phe Gly
        675                 680                 685

His

<210> SEQ ID NO 49
<211> LENGTH: 23
<212> TYPE: DNA
<213> ORGANISM: Homo sapiens

<400> SEQUENCE: 49
```

```
gcaaaggcca tcgcagaaga cat                                            23

<210> SEQ ID NO 50
<211> LENGTH: 26
<212> TYPE: DNA
<213> ORGANISM: Homo sapiens

<400> SEQUENCE: 50
gtgaagatct gcagaaaatc catgta                                         26

<210> SEQ ID NO 51
<211> LENGTH: 2187
<212> TYPE: DNA
<213> ORGANISM: Homo sapiens

<400> SEQUENCE: 51
gccatggtga acgaagccag aggaaacagc agcctcaacc cctgcttgga gggcagtgcc    60
agcagtggca gtgagagctc aaagatagt tcgagatgtt ccaccccggg cctggaccct    120
gagcggcatg agagactccg ggagaagatg aggcggcgat tggaatctgg tgacaagtgg   180 ttctcccctgg aattcttccc tcctcgaact gctgagggag ctgtcaatct catctcaagg   240
tttgaccgga tggcagcagg tggcccctc tacatagacg tgacctggca cccagcaggt    300
gaccctggct cagacaagga gacctcctcc atgatgatcg ccagcaccgc cgtgaactac   360
tgtggcctgg agaccatcct gcacatgacc tgctgccgtc agcgcctgga ggagatcacg   420
ggccatctgc acaaagctaa gcagctgggc ctgaagaaca tcatggcgct gcggggagac   480
ccaataggtg accagtggga agaggaggag ggaggcttca actacgcagt ggacctggtg   540
aagcacatcc gaagtgagtt tggtgactac tttgacatct gtgtggcagg ttaccccaaa   600
ggccaccccg aagcagggag ctttgaggct gacctgaagc acttgaagga aaggtgtct    660 gcgggagccg atttcatcat cacgcagctt ttctttgagg ctgacacatt cttccgcttt   720
gtgaaggcat gcaccgacat gggcatcact gccccatcg tccccgggat ctttcccatc    780
cagggctacc actcccttcg gcagcttgtg aagctgtcca agctggaggt gccacaggag   840
atcaaggacg tgattgagcc aatcaaagac aacgatgctg ccatccgcaa ctatggcatc   900
gagctggccg tgagcctgtg ccaggagctt ctggccagtg gcttggtgcc aggcctccac   960
ttctacaccc tcaaccgcga gatggctacc acagaggtgc tgaagcgcct ggggatgtgg   1020
actgaggacc ccaggcgtcc cctaccctgg gctctcagtg cccaccccaa cgccgagag    1080 gaagatgtac gtcccatctt ctgggcctcc agaccaaaga gttacatcta ccgtacccag   1140 gagtgggacac agttccctaa cggccgctgg ggcaattcct cttcccctgc ctttggggag   1200
ctgaaggact actacctctt ctacctgaag agcaagtccc caaggagga gctgctgaag   1260 atgtgggggg aggagctgac cagtgaagca agtgtctttg aagtctttgt tctttacctc   1320
tcgggagaac caaaccggaa tggtcacaaa gtgacttgcc tgccctggaa cgatgagccc   1380
ctggcggctg agaccagcct gctgaaggag gagctgctgc gggtgaaccg ccagggcatc   1440
ctcaccatca actcacagcc caacatcaac gggaagccgt cctccgaccc catcgtgggc   1500
tggggcccca gcgggggcta tgtcttccag aaggcctact agagtttttt cacttcccgc   1560
gagacagcgg aagcacttct gcaagtgctg aagaagtacg agctccgggt taattaccac   1620
cttgtcaatg tgaagggtga aaacatcacc aatgccctg aactgcagcc gaatgctgtc   1680
acttggggca tcttccctgg gcgagagatc atccagccca ccgtagtgga tcccgtcagc   1740
```

```
ttcatgttct ggaaggacga ggcctttgcc ctgtggattg agcggtgggg aaagctgtat    1800
gaggaggagt ccccgtcccg caccatcatc cagtacatcc acgacaacta cttcctggtc    1860
aacctggtgg acaatgactt cccactggac aactgcctct ggcaggtggt ggaagacaca    1920
ttggagcttc tcaacaggcc cacccagaat gcgagagaaa cggaggctcc atgaccctgc    1980
gtcctgacgc cctgcgttgg agccactcct gtcccgcctt cctcctccac agtgctgctt    2040
ctcttgggaa ctccactctc cttcgtgtct ctcccacccc ggcctccact ccccacctg    2100 acaatggcag ctagactgga gtgaggcttc caggctcttc ctggacctga gtcggcccca    2160
catgggaacc tagtactctc tgctcta                                        2187
```

<210> SEQ ID NO 52
<211> LENGTH: 20
<212> TYPE: PRT
<213> ORGANISM: Homo sapiens

<400> SEQUENCE: 52

Phe Leu Leu Leu Tyr Ala Thr Gln Gln Gly Gln Ala Lys Ala Ile Ala
 1               5                  10                  15

Glu Glu Met Cys
        20

<210> SEQ ID NO 53
<211> LENGTH: 23
<212> TYPE: PRT
<213> ORGANISM: Homo sapiens

<400> SEQUENCE: 53

Val Val Val Val Ser Thr Thr Gly Thr Gly Asp Pro Pro Asp Thr Ala
 1               5                  10                  15

Arg Lys Phe Val Lys Glu Ile
        20

<210> SEQ ID NO 54
<211> LENGTH: 29
<212> TYPE: PRT
<213> ORGANISM: Homo sapiens

<400> SEQUENCE: 54

Ala His Leu Arg Tyr Gly Leu Leu Gly Leu Gly Asp Ser Glu Tyr Thr
 1               5                  10                  15

Tyr Phe Cys Asn Gly Gly Lys Ile Ile Asp Lys Arg Leu
        20                  25

<210> SEQ ID NO 55
<211> LENGTH: 19
<212> TYPE: PRT
<213> ORGANISM: Homo sapiens

<400> SEQUENCE: 55

Leu Gln Pro Arg Pro Tyr Ser Cys Ala Ser Ser Leu Phe His Pro
 1               5                  10                  15

Gly Lys Leu

<210> SEQ ID NO 56
<211> LENGTH: 14
<212> TYPE: PRT
<213> ORGANISM: Homo sapiens

<400> SEQUENCE: 56

-continued

```
Phe Val Phe Asn Ile Val Glu Phe Leu Ser Thr Ala Thr Thr
 1               5                  10
```

<210> SEQ ID NO 57
<211> LENGTH: 17
<212> TYPE: PRT
<213> ORGANISM: Homo sapiens

<400> SEQUENCE: 57

```
Leu Arg Lys Gly Val Cys Thr Gly Trp Leu Ala Leu Leu Val Ala Ser
 1               5                  10                  15
Val
```

<210> SEQ ID NO 58
<211> LENGTH: 22
<212> TYPE: PRT
<213> ORGANISM: Homo sapiens

<400> SEQUENCE: 58

```
Ile Pro Ile Ile Met Val Gly Pro Gly Thr Gly Ile Ala Pro Phe Ile
 1               5                  10                  15
Gly Phe Leu Gln His Arg
            20
```

<210> SEQ ID NO 59
<211> LENGTH: 6
<212> TYPE: PRT
<213> ORGANISM: Homo sapiens

<400> SEQUENCE: 59

```
Ser Phe Ser Arg Asp Ala
 1               5
```

<210> SEQ ID NO 60
<211> LENGTH: 41
<212> TYPE: PRT
<213> ORGANISM: Homo sapiens

<400> SEQUENCE: 60

```
Ala Pro Ala Lys Tyr Val Gln Asp Asn Ile Gln Leu His Gly Gln Gln
 1               5                  10                  15
Val Ala Arg Ile Leu Leu Gln Glu Asn Gly His Ile Tyr Val Cys Gly
            20                  25                  30
Asp Ala Lys Asn Met Ala Lys Asp Val
            35                  40
```

<210> SEQ ID NO 61
<211> LENGTH: 9
<212> TYPE: PRT
<213> ORGANISM: Homo sapiens

<400> SEQUENCE: 61

```
Lys Arg Tyr Leu Gln Asp Ile Trp Ser
 1               5
```